(12) United States Patent
Stocker et al.

(10) Patent No.: US 7,173,025 B1
(45) Date of Patent: Feb. 6, 2007

(54) AMINOHETEROCYCLIC DERIVATIVES AS ANTITHROMBOTIC OR ANTICOAGULANT AGENTS

(75) Inventors: Andrew Stocker, Cheshire (GB); John Preston, Cheshire (GB); Michael James Smithers, Cheshire (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/117,436

(22) PCT Filed: Jan. 31, 1997

(86) PCT No.: PCT/GB97/00284

§ 371 (c)(1),
(2), (4) Date: Aug. 2, 1998

(87) PCT Pub. No.: WO97/28129

PCT Pub. Date: Aug. 7, 1997

(30) Foreign Application Priority Data

Feb. 2, 1996 (GB) .............................. 9602166

(51) Int. Cl.
*A61K 31/55* (2006.01)
*A61K 31/495* (2006.01)
*C07D 401/00* (2006.01)
*C07D 223/00* (2006.01)

(52) U.S. Cl. .................. 514/218; 514/252.18; 544/360; 540/484

(58) Field of Classification Search ............. 546/278.7, 546/278.4; 514/255, 422, 252.18, 218; 544/360; 540/484
See application file for complete search history.

(56) References Cited

U.S. PATENT DOCUMENTS

| | | | |
|---|---|---|---|
| 4,167,567 A | 9/1979 | McCall | |
| 5,332,822 A | 7/1994 | Misra | |
| 5,371,091 A | 12/1994 | Misra et al. | |
| 5,411,971 A | 5/1995 | Emonds-Alt et al. | |
| 5,606,065 A | 2/1997 | Emonds-Alt et al. | |
| 5,856,326 A | 1/1999 | Anthony et al. | |

FOREIGN PATENT DOCUMENTS

| | | |
|---|---|---|
| AU | 10177/92 | 7/1992 |
| DE | 42 43 858 A1 | 6/1994 |
| DE | 43 06 506 A1 | 9/1994 |
| EP | 0 233 051 | 8/1987 |
| EP | 0 244 115 | 11/1987 |
| EP | 0 308 337 | 3/1989 |
| EP | 0 359 389 | 3/1990 |
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 576 941 A1 | 1/1994 |
| EP | 0691959 | * 1/1996 |
| GB | 1 449 100 | 9/1976 |
| WO | WO 92/18478 | 10/1992 |
| WO | WO 93/06085 | 4/1993 |
| WO | WO 94/20467 | 9/1994 |
| WO | WO 94/20468 | 9/1994 |
| WO | WO 96/10022 | 4/1996 |
| WO | WO 96/26196 | 8/1996 |
| WO | WO 96/30343 | 10/1996 |
| WO | WO 97/096802 | 2/1997 |
| WO | WO 97/28128 | 8/1997 |
| WO | WO 97/28129 | 8/1997 |
| WO | WO 97/30971 | 8/1997 |
| WO | WO 98/06705 | 2/1998 |

OTHER PUBLICATIONS

Thomae et al., Arzneim. –Forsch., Synthesis and N–benzylaminocarboxylic acids and their deriviatives, vol. 23(2a), pp. 290–295, 1973.*

Budavari: Merck Index, Vol 11 Ed., 1989, See Monograph Nos. 804 and 2807.

Cattel et al: "Drug design based on biosynthetic studies: synthesis, biological activity, and kinetics of new inhibitors of 2,3–oxidosualene cyclase and squalene epoxidase.", Steroids., vol 53, no 3–5, 1989, pp. 363–391, XP000611661.

Sartori et al., "Synthesis and analgesic activities of urea derivatives of α–amino–N–pyridyl benzene propanamide", Eur J. Med Chem (1994), 431–439.

Tabacik et al: "Squalene expoxidase, oxido–squalene cyclase and cholesterol biosynthesis in normal and tumoral mucosa of the human gastrointestinal tract. Evidence of post–HMGCoA regulation.", Biochim. Biophys. Acta, vol 666, No. 3, 1982, pp. 433–441, XP000610864.

(Continued)

*Primary Examiner*—Alan L. Rotman
*Assistant Examiner*—Binta Robinson
(74) *Attorney, Agent, or Firm*—Morgan, Lewis & Bockius LLP

(57) ABSTRACT

Compounds of formula (I), wherein $G^1$ is CH or N; $G^2$ is CH or N; $R^1$ is a variety of optional substituents; $L^1$ is (1–4C) alkylene; $T^1$ is CH or N; $R^2$ and $R^3$ are independently hydrogen or (1–4C)alkyl or are joined to form a ring; $X^1$ and $X^2$ represent various linking groups; Ar is phenylene or certain heteroaryl rings and Q represents a variety of aromatic or heterocyclic rings systems, and pharmaceutically acceptable salts thereof are described as useful antithrombotic and anticoagulant agents, and are selective Factor Xa inhibitors. Processes for their preparation and pharmaceutical compositions containing them are also described.

(I)

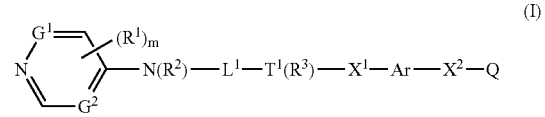

14 Claims, No Drawings

OTHER PUBLICATIONS

Wallis, "Inhibitors of Coagulation Factor Xa: From Macromolecular Beginnings to Small Molecules", Current Opinion in Therapeutic Patents, Aug., 1993, pp. 1173–1179.

R.B. Wallis, "Inhibitors of Coagulation Factor Xa: From Macromolecular Beginnings to Small Molecules", Current Opinion in Therapeutic Patents, London, pp. 1173–1179, (1993).

S. Budavari et al., "The Merck Index, 12 Edition", Merck Research Laboratories, Whitehouse Station, N.J., pp. 131, 132 and 476, (1996).

C. Kettner et al., "The Selective Inhibition of Thrombin by Peptides of Boroarginine", The Journal of Biological Chemistry, vol. 265, No. 30, pp. 18289–18297, (1990).

Gerard M.T. Vogel et al., "Comparison of Two Experimental Thrombosis Models in Rats Effects of Four Glycosaminogylcans", Thrombosis Research, vol. 54, No. 5, pp. 399–410, (1989).

J.R. Smith et al., "Fibrin, Red Cell and Platelet Interactions in an Experimental Model of Thrombosis", Br. J. Pharmac., vol. 77, pp. 29–38, (1982).

P.E. Cross et al., "Preparation of N–[(heterocyclylmethoxy)phenyl] sulfamides and analogs as antiarrhythmics", Chemical Abstracts, Abstract No. 231211, vol. 113, (1989).

A. Vigroux et al., "Cyclization–Activated Prodrugs: N–(Substituted 2–hydroxyphenyl and 2–hydroxypropyl)carbamates Based on Ring–Opened Derivatives of Active Benzoxazolones and Oxazolidinones as Mutual Prodrugs of Acetaminophen", J. Med. Chem., Vol 38, pp. 3983–3994, (1995).

P.A. Chambers et al., "Preparation of arylpyridine compounds for treating leukotriene–related diseases", Chemical Abstracts, Abstract No. 139113, vol. 119, (1993).

H. Harry Szmant et al., "Concerning the Variable Character of the Sulfone Group", J. Amer. Chem. Soc., vol. 78, pp. 3400–3403, (1956).

* cited by examiner

AMINOHETEROCYCLIC DERIVATIVES AS ANTITHROMBOTIC OR ANTICOAGULANT AGENTS

The invention relates to aminoheterocyclic derivatives and pharmaceutically-acceptable salts thereof, which possess antithrombotic and anticoagulant properties and are accordingly useful in methods of treatment of the human or animal body. The invention also relates to processes for the preparation of said aminoheterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, Current Opinion in Therapeutic Patents, 1993, 1173–1179. Thus it is known that two proteins, one known as antistasin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenyl or amidinonaphthyl group.

It is the object of the present invention to provide a new class of agent which lacks the amidino group previously believed to be an essential feature for a Factor Xa inhibitor.

We have now found that certain amino-substituted heterocyclic derivatives possess Factor Xa inhibitory activity and in particular also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic events associated with coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, disseminated intravascular coagulation, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

According to one aspect of the invention there is provided an aminoheterocyclic derivative of the formula I

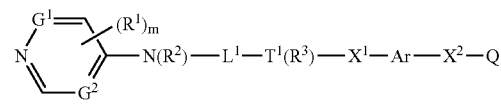

wherein
  $G^1$ is CH or N;
  $G^2$ is CH or N;
  m is 1 or 2;
  $R^1$ is hydrogen, halogeno, trifluoromethyl, trifluoromethoxy, cyano, amino, hydroxy, nitro, (1–4C)alkyl, (1–4C)alkoxy, (1–4C)alkylamino or di-(1–4C)alkylamino;
  $L^1$ is (1–4C)alkylene, (3–6C)cycloalkane-1,2-diyl or (1–3C)alkylene-carbonyl,
  $T^1$ is CH or N,
  $R^2$ is hydrogen or (1–4C)alkyl and $R^3$ is hydrogen or (1–4C)alkyl, or $R^2$ and $R^3$ together form a (1–4C)alkylene or methylenecarbonyl group,
  and wherein 1 or 2 methylene groups within $L^1$ or the ring formed when $R^2$ and $R^3$ are linked optionally bear 1 or 2 substituents selected from carboxy, carbamoyl, (1–4C)alkyl, (1–4C)alkoxycarbonyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl, 4-(1–4C)alkylpiperazin-1-ylcarbonyl, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, pyrrolidin-1-ylcarbonyl-(1–4C)alkyl, piperidino-(1–4C)alkyl, morpholino-(1–4C)alkyl, piperazin-1-yl-(1–4C)alkyl and 4-(1–4C)alkylpiperazin-1-yl-(1–4C)alkyl, and wherein any heterocyclic group in said substituent optionally bears 1 or 2 (1–4C)alkyl substituents, provided that, when $T^1$ is N, $L^1$ is not optionally substituted methylene and $R^2$ and $R^3$ together do not form an optionally substituted methylene group;
  $X^1$ is a group of the formula SO, $SO_2$, $C(R^4)_2$, CO, $C(R^4)_2O$, $C(R^4)_2S$, $C(R^4)_2SO$, $C(R^4)_2SO_2$, $COC(R^4)_2$, $SOC(R^4)_2$ or $SO_2C(R^4)_2$ when $T^1$ is CH or N, or, in addition, $X^1$ is a group of the formula O, S, $OC(R^4)_2$ or $SC(R^4)_2$ when $T^1$ is CH, and wherein each $R^4$ is independently hydrogen or (1–4C)alkyl;
  Ar is phenylene, or a 5- or 6-membered monocyclic heteroaryl ring containing up to 3 heteroatoms selected from nitrogen, oxygen and sulphur, and wherein said phenylene or heteroaryl ring is optionally substituted with 1 or 2 substituents selected from halogeno, trifluoromethyl, trifluoromethoxy, cyano, nitro, (1–4C)alkyl, (2–4C)alkenyl and (2–4C)alkynyl, from the substituent $Y^1$ which is selected from hydroxy, amino, (1–4C)alkoxy, (2–4C)alkenyloxy, (2–4C)alkynyloxy, (1–4C)alkylamino, di-(1–4C)alkylamino, pyrrolidin-1-yl, piperidino, morpholino, thiamorpholino, 1-oxothiamorpholino, 1,1-dioxothiamorpholino, piperazin-1-yl, 4-(1–4C)alkylpiperazin-1-yl, (1–4C)

alkylthio, (1–4C)alkylsulphinyl, (1–4C)alkylsulfonyl, (2–4C)alkanoylamino, benzamido, (1–4C)alkanesulphonamido and benzenesulphonamido, from the substituent $Y^2$ which is selected from carboxy, carbamoyl, (1–4C)alkoxycarbonyl, N-(1–4C)alkylcarbamoyl, N,N-di-(1–4C)alkylcarbamoyl, pyrrolidin-1-ylcarbonyl, piperidinocarbonyl, morpholinocarbonyl, thiamorpholinocarbonyl, 1-oxothiamorpholinocarbonyl, 1,1-dioxothiamorpholinocarbonyl, piperazin-1-ylcarbonyl, 4-(1–4C)alkylpiperazin-1-ylcarbonyl, (1–4C)alkanesulphonamidocarbonyl, benzenesulphonamidocarbonyl and benzylsulphonamidocarbonyl, from a substituent of the formula —$L^2$—$Y^1$ wherein $L^2$ is (1–4C)alkylene and $Y^1$ has any of the meanings defined immediately hereinbefore, from a substituent of the formula —$L^2$—$Y^2$ wherein $L^2$ is (1–4C)alkylene and $Y^2$ has any of the meanings defined immediately hereinbefore, from a substituent of the formula —$X^3$—$L^2$—$Y^2$ wherein $X^3$ is a group of the formula $CON(R^5)$, $CON(L^2$—$Y^2)$, $C(R^5)_2O$, O, $N(R^5)$ or $N(L^2$—$Y^2)$, $L^2$ is (1–4C)alkylene, $Y^2$ has any of the meanings defined immediately hereinbefore and each $R^5$ is independently hydrogen or (1–4C)alkyl, and from a substituent of the formula —$X^3$—$L^3$—$Y^1$ wherein $X^3$ is a group of the formula $CON(R^5)$, $CON(L^3$—$Y^1)$, $C(R^5)_2O$, O, $N(R^5)$ or $N(L^3$—$Y^1)$, $L^3$ is (2–4C)alkylene, $Y^1$ has any of the meanings defined immediately hereinbefore and each $R^5$ is independently hydrogen or (1–4C)alkyl, and wherein any heterocyclic group in said substituent optionally bears 1 or 2 substituents selected from carboxy, carbamoyl, (1–4C)alkyl, (1–4C)alkoxycarbonyl, N-(1–4C)alkylcarbonyl and N,N-di-(1–4C)alkylcarbamoyl, and wherein any phenyl group in said substituent optionally bears 1 or 2 substituents selected from halogeno, trifluoromethyl, cyano, (1–4C)alkyl, (2–4C)alkenyl, (2–4C)alkynyl, (1–4C)alkoxy, (2–4C)alkenyloxy and (2–4C)alkynyloxy;

$X^2$ is a group of the formula S, SO, $SO_2$, $C(R^6)_2$, CO, $N(R^7)SO_2$, $N(R^7)CO$, $C(R^6)_2S$, $C(R^6)_2SO$, $C(R^6)_2SO_2$, $C(R^6)_2$—$C(R^6)_2$ or $C(R^6)_2CO$, or, in addition, $X^2$ is a group of the formula O, $SO_2N(R^7)$, $CON(R^7)$ or $C(R^6)_2O$ when Q is other than phenyl-(2–4C)alkenyl or phenyl-(2–4C)alkynyl and wherein each $R^6$ is independently hydrogen or (1–4C)alkyl and $R^7$ is hydrogen, (1–4C)alkyl or a group of the formula —$X^4$—Q wherein $X^4$ is $SO_2$ or CO and Q has any of the meanings defined immediately hereinafter; and Q is phenyl, naphthyl, phenyl-(1–4C)alkyl, phenyl-(2–4C)alkenyl, phenyl-(2–4C)alkynyl or a heterocyclic moiety containing up to 4 heteroatoms selected from nitrogen, oxygen and sulphur, and Q optionally bears 1, 2 or 3 substituents selected from halogeno, trifluoromethyl, trifluoromethoxy, cyano, hydroxy, amino, nitro, trifluoromethanesulphonyl, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, phenyl, heteroaryl, phenoxy, phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group in a heteroaryl-containing substituent comprises a 5- or 6-membered monocyclic heteroaryl ring containing up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halogeno, trifluoromethyl, cyano, hydroxy, amino, nitro, carboxy, carbamoyl, (1–4C)alkyl, (1–4C)alkoxy, (1–4C)alkylamino, di-(1–4C)alkylamino, (1–4C)alkoxycarbonyl, N-(1–4C)alkylcarbamoyl, N,N-di-(1–4C)alkylcarbamoyl and (2–4C)alkanoylamino;

or a pharmaceutically-acceptable salt thereof;

provided that when $X^1$ is CO and Ar is phenylene which optionally bears 1 or 2 substituents selected from halogeno, trifluoromethyl, (1–4C)alkyl and (1–4C)alkoxy then $X^2$ is not $N(R^7)SO_2$, $N(R^7)CO$, $C(R^6)_2S$, $C(R^6)_2SO$, $C(R^6)_2SO_2$, $C(R^6)_2$—$C(R^6)_2$, $C(R^6)_2CO$ or $C(R^6)_2O$.

In this specification the term "alkyl" includes both straight and branched chain alkyl groups but references to individual alkyl groups such as "propyl" are specific for the straight chain version only. An analogous convention applies to other generic terms.

It is to be understood that certain aminoheterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or b) resolution of a racemic form.

Suitable values for the generic terms referred to above include those set out below.

When m is 2, each $R^1$ is independently selected from the list of substituents defined hereinbefore.

A suitable value for $R^1$ when it is a halogeno group or for a halogeno substituent on Ar, on a phenyl group within any substituent on Ar, on Q or on a phenyl- or heteroaryl-containing substituent on Q is, for example, fluoro, chloro, bromo or iodo.

A suitable value for $R^1$ when it is a (1–4C)alkyl group or for a (1–4C)alkyl substituent on Ar, on a heterocyclic or phenyl group within any substituent on Ar, on Q or on a phenyl- or heteroaryl-containing substituent on Q is, for example, methyl, ethyl, propyl, isopropyl, butyl, isobutyl, sec-butyl or tert-butyl.

A suitable value for $R^1$ when it is a (1–4C)alkoxy group or for a (1–4C)alkoxy substituent on Ar, on a phenyl group within any substituent on Ar, on Q or on a phenyl- or heteroaryl-containing substituent on Q is, for example, methoxy, ethoxy, propoxy, isopropoxy or butoxy.

A suitable value for $R^1$ when it is a (1–4C)alkylamino group or for a (1–4C)alkyl amino substituent on Ar, on Q or on a phenyl- or heteroaryl-containing substituent on Q is, for example, methylamino, ethylamino or propylamino.

A suitable value for $R^1$ when it is di-(1–4C)alkylamino or for a di-(1–4C)alkylamino substituent on Ar, on Q or on a phenyl- or heteroaryl-containing substituent on Q is, for example, dimethylamino, N-ethyl-N-methylamino or diethylamino.

A suitable value for $R^2$, $R^3$, $R^4$, $R^5$, $R^6$ or $R^7$ when it is (1–4C)alkyl is, for example, methyl, ethyl, propyl, isopropyl, butyl or sec-butyl.

A suitable value for a (1–4C)alkylene group formed by $R^2$ and $R^3$ together is, for example, methylene, ethylene, trimethylene or tetramethylene.

A suitable value for $L^1$ when it is (1–4C)alkylene is, for example, methylene, ethylene, trimethylene or tetramethylene; when it is (3–6C)cycloalkane-1,2-diyl is, for example, cyclopropane-1,2-diyl, cyclobutane-1,2-diyl, cyclopentane-1,2-diyl or cyclohexane-1,2-diyl; and when it is (1–3C) alkylene-carbonyl is, for example, methylenecarbonyl, ethylenecarbonyl or trimethylenecarbonyl.

A suitable value for a substituent which may be present on 1 or 2 methylene groups within $L^1$ or the ring formed when $R^2$ and $R^3$ are linked is, for example, as follows:

for (1–4C)alkyl: methyl, ethyl and propyl;
for (1–4C)alkoxycarbonyl: methoxycarbonyl, ethoxycarbonyl, propoxycarbonyl and tert-butoxycarbonyl;
for N-(1–4C)alkylcarbamoyl: N-methylcarbamoyl, N-ethylcarbamoyl and N-propylcarbamoyl;
for N,N-di-[(1–4C)alkyl]carbamoyl: N,N-dimethylcarbamoyl, N-ethyl-N-methylcarbamoyl and N,N-diethylcarbamoyl;
for 4-(1–4C)alkylpiperazin-1-ylcarbonyl: 4-methylpiperazin-1-ylcarbonyl and 4-ethylpiperazin-1-ylcarbonyl;
for hydroxy-(1–4C)alkyl: hydroxymethyl, 1-hydroxyethyl, 2-hydroxyethyl and 3-hydroxypropyl;
for (1–4C)alkoxy-(1–4C)alkyl: methoxymethyl, ethoxymethyl, 1-methoxymethyl, 2-methoxyethyl, 2-ethoxyethyl and 3-methoxypropyl;
for carboxy-(1–4C)alkyl: carboxymethyl, 1-carboxyethyl, 2-carboxyethyl and 3-carboxypropyl;
for (1–4C)alkoxycarbonyl-(1–4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;
for carbamoyl-(1–4C)alkyl: carbamoylmethyl, 1-carbamoylethyl, 2-carbamoylethyl and 3-carbamoylpropyl;
for N-(1–4C)alkylcarbamoyl-(1–4C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl) ethyl, 2-(N-ethylcarbamoyl)ethyl and 3-(N-methylcarbamoyl)propyl;
for N,N-di-[(1–4C)alkyl]carbamoyl-(1–4C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl) ethyl, 2-(N,N-diethylcarbamoyl)ethyl and 3-(N,N-dimethylcarbamoyl)propyl;
for pyrrolidin-1-ylcarbonyl-(1–4C)alkyl: pyrrolidin-1-ylcarbonylmethyl, 1-(pyrrolidin-1-ylcarbonyl)ethyl and 2-(pyrrolidin-1-ylcarbonyl)ethyl;
for piperidinocarbonyl-(1–4C)alkyl: piperidinocarbonylmethyl, 1-(piperidinocarbonyl)ethyl and 2-(piperidinocarbonyl)ethyl;
for morpholinocarbonyl-(1–4C)alkyl: morpholinocarbonylmethyl, 1-(morpholinocarbonyl) ethyl and 2-(morpholinocarbonyl)ethyl;
for piperazin-1-ylcarbonyl-(1–4C)alkyl: piperazin-1-ylcarbonylmethyl, 1-(piperazin-1-ylcarbonyl)ethyl and 2-(piperazin-1-ylcarbonyl)ethyl;
for 4-(1–4C)alkylpiperazin-1-ylcarbonyl-(1–4C)alkyl: 4-methylpiperazin-1-ylcarbonylmethyl, 4-ethylpiperazin-1-ylcarbonylmethyl, 2-(4-methylpiperazin-1-ylcarbonyl) ethyl and 2-(4-ethylpiperazin-1-ylcarbonyl)ethyl.

For suitable value for a (1–4C)alkyl group which may be present on a heterocyclic group in a substituent on $L^1$ or the ring formed when $R^2$ and $R^3$ are linked is, for example, methyl, ethyl or propyl.

A suitable value for Ar when it is phenylene is, for example, 1,2-, 1,3- or 1,4-phenylene.

A suitable value for Ar when it is a 5- or 6-membered monocyclic heteroaryl ring containing up to 3 heteroatoms selected from nitrogen, oxygen and sulphur is, for example, furandiyl, thiophenediyl, pyridinediyl, pyrazinediyl, pyrimidinediyl, pyridazinediyl, pyrrolediyl, pyrazolediyl, imidazolediyl, oxazolediyl, isoxazolediyl, thiazolediyl, isothiazolediyl, 1,2,3-triazolediyl, 1,2,4-triazolediyl, oxadiazolediyl, furazandiyl, thiadiazolediyl and 1,3,5-triazinediyl which may be attached through any available position including through any available nitrogen atom. Convenient values for Ar include 2,4- or 2,5-furandiyl, 2,4- or 2,5-thiophenediyl, 2,4-, 2,5-, 2,6- or 3,5-pyridinediyl, 2,4-, 2,5- or 4,6-pyrimidinediyl, 1,4-, 2,4-, 2,5-, 4,1- or 5,2-imidazolediyl, 2,4- or 2,5-oxazolediyl, 2,4- or 2,5-thiazolediyl, 2,5-oxadiazolediyl, 2,5-thiadiazolediyl and 1,3,5-triazine-2,4-diyl.

A suitable value for $L^2$ when it is (1–4C)alkylene is, for example, methylene, ethylene, trimethylene or tetramethylene; and for $L^3$ when it is (2–4C)alkylene is, for example, ethylene, trimethylene or tetramethylene.

Suitable values for substituents which may be present on Ar, on a heterocyclic or phenyl group within a substituent on Ar, on Q or on a phenyl- or heteroaryl-containing substituent on Q include, for example:

for (2–4C)alkenyl: vinyl and allyl;
for (2–4C)alkynyl: ethynyl and prop-2-ynyl;
for (2–4C)alkenyloxy: vinyloxy and allyloxy;
for (2–4C)alkynyloxy: ethynyloxy and prop-2-ynyloxy;
for 4-(1–4C)alkylpiperazin-1-yl: 4-methylpiperazin-1-yl and 4-ethylpiperazin-1-yl;
for (1–4C)alkylthio: methylthio, ethylthio and propylthio;
for (1–4C)alkylsulphinyl: methylsulphinyl, ethylsulphinyl and propylsulphinyl;
for (1–4C)alkylsulphonyl: methylsulphonyl, ethylsulphonyl and propylsulphonyl;
for (2–4C)alkanoylamino: acetamido, propionamido and butyramido;
for (1–4C)alkanesulphonamido: methanesulphonamido and ethanesulphonamido;
for (1–4C)alkoxycarbonyl: methoxycarbonyl, ethoxycarbonyl, propoxycarbonyl and tert-butoxycarbonyl;
for N-(1–4C)alkylcarbamoyl: N-methylcarbamoyl, N-ethylcarbamoyl and N-propylcarbamoyl;
for N,N-di-[(1–4C)alkyl]carbamoyl: N,N-dimethylcarbamoyl, N-ethyl-N-methylcarbamoyl and N,N-diethylcarbamoyl;
for 4-(1–4C)alkylpiperazin-1-ylcarbonyl: 4-methylpiperazin-1-ylcarbonyl and 4-ethylpiperazin-1-ylcarbonyl;

for (1–4C)alkanesulphonamidocarbonyl: methanesulphonamidocarbonyl and ethanesulphonamidocarbonyl;

for (2–4C)alkanoyl: acetyl, propionyl and butyryl;

for hydroxy-(1–4C)alkyl: hydroxymethyl, 1-hydroxyethyl, 2-hydroxyethyl and 3-hydroxypropyl;

for (1–4C)alkoxy-(1–4C)alkyl: methoxymethyl, ethoxymethyl, 1-methoxymethyl, 2-methoxyethyl, 2-ethoxyethyl and 3-methoxypropyl;

for carboxy-(1–4C)alkyl: carboxymethyl, 1-carboxyethyl, 2-carboxyethyl and 3-carboxypropyl;

for (1–4C)alkoxycarbonyl-(1–4C)alkyl: methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;

for carbamoyl-(1–4C)alkyl: carbamoylmethyl, 1-carbamoylethyl, 2-carbamoylethyl and 3-carbamoylpropyl;

for N-(1–4C)alkylcarbamoyl-(1–4C)alkyl: N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl;

for N,N-di-[(1–4C)alkyl]carbamoyl-(1–4C)alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;

For the avoidance of doubt it is stated that a suitable heterocyclic group in a substituent which may be present on Ar includes, for example, pyrrolidin-1-yl, piperidino, morpholino, piperazin-1-yl and 4-(1–4C)alkylpiperazin-1-yl whether directly attached or attached by way of a linking group as in, for example, pyrrolidin-1-ylcarbonyl.

A suitable value for Q when it is naphthyl is, for example, 1-naphthyl or 2-naphthyl; when it is phenyl-(1–4C)alkyl is, for example, benzyl, phenethyl and 3-phenylpropyl; when it is phenyl-(2–4C)alkenyl is, for example, styryl, cinnamyl or 3-phenylprop-2-enyl; and when it is phenyl-(2–4C)alkynyl is, for example, 2-phenylethynyl, 3-phenylprop-2-ynyl and 3-phenylprop-1-ynyl.

A suitable value for Q when it is a heterocyclic moiety containing up to 4 heteroatoms selected from nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate $X^2$ group such as, for example, $SO_2$, $C(R^6)_2$ or CO, through any available nitrogen atom and which may bear up to three substituents including a substituent on any available nitrogen atom.

A suitable value for the heteroaryl substituent on Q or the heteroaryl group in a heteroaryl-containing substituent on Q which comprises a 5- or 6-membered monocyclic heteroaryl ring containing up to 3 heteroatoms selected from oxygen, nitrogen and sulphur is, for example, furyl, thienyl, pyridyl, pyrazinyl, pyrimidinyl, pyridazinyl, pyrrolyl, imidazolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including through any available nitrogen atom.

For the avoidance of any doubt it is to be understood that, in the portion of the structure of formula I which has the formula $—N(R^2)—L^1—T^1(R^3)—X^1—$, it is the N atom which is attached to $L^1$ and it is the $T^1$ group which is attached to $X^1$ i.e. neither of the $R^2$ and $R^3$ groups are attached to $L^1$.

It is further to be understood that, within the structure of formula I, when $R^2$ and $R^3$ together form a methylenecarbonyl group, it is the methylene group thereof which is attached to the N atom and the carbonyl group thereof which is attached to $T^1$. Similarly when $L^1$ is a (1–3C)alkylenecarbonyl group, for example a methylenecarbonyl group, it is the methylene group thereof which is attached to the N atom and the carbonyl group thereof which is attached to $T^1$.

It is also to be understood that, within the structure of formula I, when $X^1$ is, for example, a group of the formula $C(R^4)_2O$, it is the C atom which is attached to $T^1$ and the O atom which is attached to Ar. Likewise, when $X^2$ is, for example, a group of the formula $N(R^7)SO_2$, it is the N atom which is attached to Ar and the $SO_2$ group which is attached to Q. Likewise, when $X^3$ is, for example, a group of the formula $CON(R^5)$, it is the CO group which is attached to Ar and the N atom which is attached to $L^2$ or $L^3$ as appropriate. Likewise when $X^3$ is, for example a group of the formula $CON(L^2—Y^2)$, it is the $L^2$ group which is attached to the N atom of the CON group.

A suitable pharmaceutically-acceptable salt of an aminoheterocyclic derivative of the invention is, for example, an acid-addition salt of an aminoheterocyclic derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of an aminoheterocyclic derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, aminoheterocyclic derivatives of the formula I, or pharmaceutically-acceptable salts thereof, wherein, unless otherwise stated, each of $G^1$, $G^2$, m, $R^1$, $R^2$, $R^3$, $L^1$, $T^1$, $X^1$, Ar, $X^2$ and Q has any of the meanings defined hereinbefore or in this section concerning particular compounds of the invention:

(a) each of $G^1$ and $G^2$ is CH;
(b) $G^1$ is CH and $G^2$ is N, or $G^1$ is N and $G^2$ is CH;
(c) m is 1 and $R^1$ is hydrogen;
(d) $L^1$ is (1–4C)alkylene, $T^1$ is CH or N, and $R^2$ and $R^3$ together form a (1–4C)alkylene group, and wherein 1 or 2 methylene groups within $L^1$ and the ring formed when $R^2$ and $R^3$ are linked optionally bears 1 or 2 (1–4C)alkyl substituents, provided that, when $T^1$ is N, $L^1$ is not optionally substituted methylene and $R^2$ and $R^3$ together do not form an optionally substituted methylene group;

(e) $L^1$ is ethylene, $T^1$ is CH, and $R^2$ and $R^3$ together form a methylene or ethylene group;

(f) $L^1$ is ethylene, $T^1$ is N, and $R^2$ and $R^3$ together form an ethylene group;

(ff) $L^1$ is ethylene, $T^1$ is N, and $R^2$ and $R^3$ together form an ethylene or propylene group;

(g) $L^1$ is ethylene, $T^1$ is CH or N, and $R^2$ and $R^3$ together form an ethylene group;

(h) when $T^1$ is CH or N, $X^1$ is a group of the formula $SO_2$, $CH_2$, CO, $CH_2O$, $CH_2S$, $CH_2SO_2$, $COCH_2$ or $SO_2CH_2$, or, when $T^1$ is CH, $X^1$ is, in addition, a group of the formula O, S, $OCH_2$ or $SCH_2$;

(i) when $T^1$ is CH or N, $X^1$ is a group of the formula $CH_2$, CO or $CH_2O$, or, when $T^1$ is CH, $X^1$ is, in addition, a group of the formula O;

(j) Ar is 1,3-phenylene or 1,4-phenylene which is optionally substituted with 1 or 2 substituents selected from halogeno, trifluoromethyl, cyano, (1–4C)alkyl, hydroxy, amino, (1–4C)alkoxy, (1–4C)alkylamino, di-(1–4C)alkylamino, (1–4C)alkylthio, (1–4C)alkylsulphinyl, (1–4C)alkylsulphonyl, (2–4C)alkanoylamino, carboxy, carbamoyl, (1–4C)alkoxycarbonyl, N-(1–4C)alkylcarbamoyl, N,N-di-(1–4C)alkylcarbamoyl, pyrrolidin-1-ylcarbonyl, piperidinocarbonyl, morpholinocarbonyl, thiamorpholinocarbonyl, 1-oxothiamorpholinocarbonyl, 1,1-dioxothiamorpholinocarbonyl, piperazin-1-ylcarbonyl and 4-(1–4C)alkylpiperazin-1-ylcarbonyl;

(k) Ar is 1,3-phenylene or 1,4-phenylene which is optionally substituted with a substituent of the formula —$L^2$—$Y^1$ or of the formula —$L^2$—$Y^2$ wherein $L^2$ is (1–4C)alkylene, $Y^1$ is selected from hydroxy, amino, (1–4C)alkoxy, (1–4C)alkylamino, di-(1–4C)alkylamino, pyrrolidin-1-yl, piperidino, morpholino, piperazin-1-yl, 4-(1–4C)alkylpiperazin-1-yl, (1–4C)alkylthio, (1–4C)alkylsulphinyl, (1–4C)alkylsulphonyl and (2–4C)alkanoylamino, and $Y^2$ is selected from carboxy, carbamoyl, (1–4C)alkoxycarbonyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl and 4-(1–4C)alkylpiperazin-1-ylcarbonyl;

(l) Ar is 1,3-phenylene or 1,4-phenylene which is optionally substituted with a substituent of the formula —$X^3$—$L^2$—$Y^2$ wherein $X^3$ is a group of the formula CONH, CON(Me), $CH_2O$ or O, $L^2$ is methylene, ethylene or trimethylene and $Y^2$ is selected from carboxy, carbamoyl, (1–4C)alkoxycarbonyl, N-(1–4C)alkylcarbamoyl, N,N-di-(1–4C)alkylcarbamoyl, pyrrolidin-1-ylcarbonyl, piperidinocarbonyl, morpholinocarbonyl, piperazin-1-ylcarbonyl and 4-(1–4C)alkylpiperazin-1-yl;

(m) Ar is 1,3-phenylene or 1,4-phenylene which is optionally substituted with a substituent of the formula —$X^3$—$L^3$—$Y^1$ wherein $X^3$ is a group of the formula CONH, $CH_2O$, O or NH, $L^3$ is ethylene or trimethylene and $Y^1$ is hydroxy, amino, (1–4C)alkoxy, (1–4C)alkylamino, di-(1–4C)alkylamino, pyrrolidin-1-yl, piperidino, morpholino, piperazin-1-yl, 4-(1–4C)alkylpiperazin-1-yl, (1–4C)alkylthio, (1–4C)alkylsulphinyl, (1–4C)alkylsulphonyl and (2–4C)alkanoylamino;

(n) $X^2$ is a group of the formula $SO_2$, $CH_2$, CO, $NHSO_2$, $N(R^7)SO_2$, NHCO, $N(R^7)CO$, $CH_2SO_2$, $CH_2CH_2$ or $CH_2CO$ wherein $R^7$ is (1–4C)alkyl or a group of the formula —$X^4$—Q wherein $X^4$ is $SO_2$ and Q has any of the meanings defined hereinafter in this section of particular compounds of the invention;

(nn) $X^2$ is a group of the formula S;

(o) $X^2$ is a group of the formula $SO_2$ or $NHSO_2$;

(p) $X^2$ is a group of the formula $SO_2$;

(q) $X^2$ is a group of the formula $NHSO_2$;

(r) Q is phenyl, naphthyl or phenyl-(1–4C)alkyl which optionally bears 1, 2 or 3 substituents selected from hydroxy, halogeno, cyano, trifluoromethyl, (1–4C)alkyl, (1–4C)alkoxy, phenyl, phenoxy, phenylthio, phenylsulphinyl, phenylsulphonyl, benzyl and benzoyl, and wherein the phenyl substituent or the phenyl group in a phenyl-containing substituent optionally bears 1 or 2 substituents selected from halogeno, (1–4C)alkyl and (1–4C)alkoxy;

(s) Q is phenyl which bears a phenyl substituent and optionally bears 1 or 2 substituents selected from hydroxy, halogeno, cyano, trifluoromethyl, (1–4C)alkyl and (1–4C)alkoxy, and wherein the phenyl substituent optionally bears up to 3 substituents selected from halogeno, trifluoromethyl, cyano, (1–4C)alkyl and (1–4C)alkoxy;

(t) Q is phenyl-(1–4C)alkyl, phenyl-(2–4C)alkenyl or phenyl-(2–4C)alkynyl which optionally bears 1, 2 or 3 substituents selected from halogeno, cyano, trifluoromethyl, (1–4C)alkyl and (1–4C)alkoxy;

(u) Q is phenyl-(2–4C)alkenyl which optionally bears 1, 2 or 3 substituents selected from halogeno, cyano, trifluoromethyl, (1–4C)alkyl and (1–4C)alkoxy;

(v) Q is phenyl or phenyl-(1–4C)alkyl which bears 1 substituent selected from heteroaryl, heteroaryloxy, heteroarylthio, heteroarylsulphinyl and heteroarylsulphonyl, wherein the heteroaryl substituent or the heteroaryl group in a heteroaryl-containing substituent comprises a 5- or 6-membered monocyclic heteroaryl ring containing up to 3 heteroatoms selected from nitrogen, oxygen and sulphur, and wherein said heteroaryl or heteroaryl-containing substituent optionally bears 1 or 2 substituents selected from halogeno, (1–4C)alkyl and (1–4C)alkoxy;

(w) Q is phenyl which bears 1 substituent selected from heteroaryl, heteroaryloxy, heteroarylthio and heteroarylsulphonyl, wherein the heteroaryl substituent or the heteroaryl group in a heteroaryl-containing substituent is selected from thienyl, pyridyl, pyrimidinyl, pyrazolyl, oxazolyl, thiazolyl, 1,2,3-triazolyl and 1,2,4-triazolyl, and wherein said heteroaryl or heteroaryl-containing substituent optionally bears 1 or 2 substituents selected from halogeno and (1–4C)alkyl;

(x) Q is naphthyl which optionally bears 1 or 2 substituents selected from hydroxy, halogeno, cyano, trifluoromethyl, (1–4C)alkyl and (1–4C)alkoxy;

(y) Q is a heterocyclic moiety containing up to 2 heteroatoms selected from benzofuranyl, quinolyl, tetrahydroquinolyl, isoquinolyl, quinoxalinyl, quinazolinyl, cinnolinyl, indolyl, benzimidazolyl, indazolyl, benzoxazolyl and benzothiazolyl, and Q optionally bears 1 or 2 substituents selected from halogeno, cyano, trifluoromethyl, (1–4C)alkyl and (1–4C)alkoxy;

(z) Q is a heterocyclic moiety containing up to 2 heteroatoms selected from benzofuranyl, quinolyl, tetrahydroquinolyl, isoquinolyl, quinoxalinyl, quinazolinyl, cinnolinyl, indolyl, benzimidazolyl, indazolyl, benzoxazolyl, benzothiazolyl, dibenzofuranyl and dibenzothienyl, and Q optionally bears 1 or 2 substituents selected from halogeno, cyano, trifluoromethyl, (1–4C)alkyl and (1–4C)alkoxy;

(aa) Q is a heterocyclic moiety containing up to 4 heteroatoms selected from furyl, thienyl, pyridyl, pyrimidinyl, pyrrolyl, pyrrolidinyl, imidazolyl, pyrazolyl, oxazolyl, isoxazolyl, thiazolyl, isothiazolyl, 1,2,3-triazolyl, 1,2,4-triazolyl, oxadiazolyl, thiadiazolyl and tetrazolyl, and Q optionally bears 1 or 2 substituents selected from halogeno, cyano, carboxy, carbamoyl, (1–4C)alkoxycarbonyl, (1–4C)alkyl, (1–4C)alkoxy, N-(1–4C)alkylcarbamoyl and N,N-di-(1–4C)alkylcarbamoyl;

(bb) Q is a heterocyclic moiety containing up to 2 heteroatoms selected from thienyl, pyridyl, pyrimidinyl, imidazolyl, pyrazolyl, oxazolyl and thiazolyl, and Q optionally bears 1 or 2 substituents selected from halogeno, (1–4C)alkyl, (1–4C)alkoxy, phenyl, heteroaryl, phenoxy, phenylthio, phenylsulphinyl, phenylsulphonyl, heteroaryloxy, heteroarylthio, heteroarylsulphinyl, heteroarylsulphonyl, benzyl and benzoyl, wherein the heteroaryl substituent or the heteroaryl group in a heteroaryl-containing substituent is selected from thienyl, pyridyl, pyrimidinyl, pyrazolyl, oxazolyl and thiazolyl, and wherein said phenyl, phenyl-containing, heteroaryl or heteroaryl-containing substituent optionally bears 1 or 2 substituents selected from halogeno, (1–4C)alkyl and (1–4C)alkoxy; or (cc) Q is a heterocyclic moiety containing up to 2 heteroatoms selected from thienyl, pyridyl, oxazolyl and thiazolyl, and Q bears a substituent selected from phenyl, thienyl, pyridyl, pyrimidinyl, oxazolyl and thiazolyl, which substituent optionally bears 1 or 2 substituents selected from halogeno, (1–4C)alkyl and (1–4C)alkoxy, and Q optionally bears a further substituent selected from halogeno and (1–4C)alkyl; or a pharmaceutically-acceptable salt thereof; provided that when $X^1$ is CO and Ar is phenylene which optionally bears 1 or 2 substituents selected from halogeno, trifluoromethyl, (1–4C)alkyl and (1–4C)alkoxy then $X^2$ is not $N(R^7)SO_2$, $N(R^7)CO$, $C(R^6)_2S$, $C(R^6)_2SO$, $C(R^6)_2SO_2$, $C(R^6)_2$—$C(R^6)_2$, $C(R^6)_2CO$ or $C(R^6)_2O$.

A particular compound of the invention is an aminoheterocyclic derivative of the formula I
wherein each of $G^1$ and $G^2$ is CH, $G^1$ is CH and G is N, or $G^1$ is N and $G^2$ is CH;

m is 1 and $R^1$ is hydrogen;

$L^1$ is ethylene, $T^1$ is CH or N, and $R^2$ and $R^3$ are independently hydrogen or together form a methylene, ethylene or propylene group;

when $T^1$ is CH or N, $X^1$ is a group of the formula $CH_2$, CO, $CH_2O$ or $SO_2$, or, when $T^1$ is CH, $X^1$ is, in addition, a group of the formula O;

Ar is 1,2-phenylene, 1,3-phenylene, 1,4-phenylene or pyridyl group which is optionally substituted with 1 or 2 substituents selected from fluoro, chloro, bromo, trifluoromethyl, cyano, methyl, hydroxy, amino, methoxy, methylamino, dimethylamino, methylthio, methylsulphinyl, methylsulphonyl, acetamido, carboxy, carbamoyl, methoxycarbonyl, ethoxycarbonyl, N-methylcarbamoyl, N,N-dimethylcarbamoyl, 2-(ethylthio)ethylaminocarbonyl, pyrrolidin-1-ylcarbonyl, piperidinocarbonyl, morpholinocarbonyl, piperazin-1-ylcarbonyl and 4-methylpiperazin-1-ylcarbonyl;

X is a group of the formula S, $SO_2$, CONH, $NHSO_2$ or $N(R^7)SO_2$ wherein $R^7$ is methyl or a group of the formula —$SO_2Q$ wherein Q has any of the meanings defined immediately hereinafter, and Q is phenyl, styryl, 1,2,3,4-tetrahydroisoquinolinyl, indolyl, 4-biphenylyl or 2-naphthyl which optionally bears 1 or 2 substituents selected from fluoro, chloro, bromo, trifluoromethyl, 4-chlorophenoxy, methyl and methoxy;

or a pharmaceutically-acceptable salt thereof;

provided that when $X^1$ is CO and Ar is 1,2-, 1,3- or 1,4-phenylene which optionally bears 1 or 2 substituents selected from fluoro, chloro, bromo, trifluoromethyl, methyl and methoxy then $X^2$ is not $NHSO_2$ or $N(R^7)SO_2$ wherein $R^7$ is methyl or a group of the formula —$SO_2$—Q wherein Q has any of the meanings defined immediately hereinbefore.

A preferred compound of the invention is an aminoheterocyclic derivative of the formula I
wherein each of $G^1$ and $G^2$ is CH, $G^1$ is CH and $G^2$ is N, or $G^1$ is N and $G^2$ is CH;

m is 1 and $R^1$ is hydrogen;

$L^1$ is ethylene, $T^1$ is CH or N, and $R^2$ and $R^3$ together form an ethylene group;

when $T^1$ is CH or N, $X^1$ is a group of the formula $CH_2$, CO or $CH_2O$, or, when $T^1$ is CH, $X^1$ is, in addition, a group of the formula O;

Ar is 1,3-phenylene or 1,4-phenylene which is optionally substituted with 1 or 2 substituents selected from fluoro, chloro, bromo, trifluoromethyl, cyano, methyl, hydroxy, amino, methoxy, methylamino, dimethylamino, methylthio, methylsulphinyl, methylsulphonyl, acetamido, carboxy, carbamoyl, methoxycarbonyl, ethoxycarbonyl, N-methylcarbamoyl, N,N-dimethylcarbamoyl, pyrrolidin-1-ylcarbonyl, piperidinocarbonyl, morpholinocarbonyl, piperazin-1-ylcarbonyl and 4-methylpiperazin-1-ylcarbonyl;

$X^2$ is a group of the formula $SO_2$, $NHSO_2$ or $N(R^7)SO_2$ wherein $R^7$ is methyl or a group of the formula —$SO_2Q$ wherein Q has any of the meanings defined immediately hereinafter; and Q is phenyl, styryl, 4-biphenylyl or 2-naphthyl which optionally bears 1 or 2 substituents selected from fluoro, chloro, bromo, trifluoromethyl, methyl and methoxy;

or a pharmaceutically-acceptable salt thereof;

provided that when $X^1$ is CO and Ar is 1,3- or 1,4-phenylene which optionally bears 1 or 2 substituents selected from fluoro, chloro, bromo, trifluoromethyl, methyl and methoxy then $X^2$ is not $NHSO_2$ or $N(R^7)SO_2$ wherein $R^7$ is methyl or a group of the formula —$SO_2$—Q wherein Q has any of the meanings defined immediately hereinbefore.

A further preferred compound of the invention is an aminoheterocyclic derivative of the formula I
wherein each of $G^1$ and $G^2$ is CH, $G^1$ is CH and $G^2$ is N, or $G^1$ is N and $G^2$ is CH;

m is 1 and $R^1$ is hydrogen;

$L^1$ is ethylene, $T^1$ is N, and $R^2$ and $R^3$ together form an ethylene or propylene group;

$X^1$ is a group of the formula CO;

Ar is 1,4-phenylene, 2-carboxy-1,4-phenylene or 2-piperidinocarbonyl-1,4-phenylene (with the $X^1$ group in the 1-position and the $X^2$ group in the 4-position);

$X^2$ is a group of the formula $SO_2$; and Q is 2-naphthyl, styryl or 4-biphenylyl which optionally bears 1 or 2 substituents selected from fluoro, chloro and bromo;

or a pharmaceutically-acceptable salt thereof.

A particularly preferred compound of the invention is an aminoheterocyclic derivative of the formula I
wherein each of $G^1$ and $G^2$ is CH;
m is 1 and $R^1$ is hydrogen;
$L^1$ is ethylene, $T^1$ is N, and $R^2$ and $R^3$ together form an ethylene group;
$X^1$ is a group of the formula CO;
Ar is 1,4-phenylene, 2-carboxy-1,4-phenylene or 2-piperidinocarbonyl-1,4-phenylene (with the $X^1$ group in the 1-position and the $X^2$ group in the 4-position);
$X^2$ is a group of the formula $SO_2$; and Q is 2-naphthyl, styryl or 4-biphenylyl which optionally bears 1 or 2 substituents selected from fluoro, chloro and bromo;
or a pharmaceutically-acceptable salt thereof.

Specific compounds of the invention include the following aminoheterocyclic derivative of the formula I:

1-[4-(6-chloronaphth-2-ylsulphonyl)benzoyl]-4-(4-pyridyl)piperazine,
1-[4-(6-bromonaphth-2-ylsulphonyl)benzoyl]-4-(4-pyridyl)piperazine,
1-[4-(2-naphthylsulphonyl)benzoyl]-4-(4-pyridyl)piperazine,
1-{4-[(E)-4-chlorostyrlsulphonyl]benzoyl}-4-(4-pyridyl)piperazine,
1-[4-(4'-bromo-4-biphenylylsulphonyl)benzoyl]-4-(4-pyridyl)piperazine,
1-[4-(4'-chloro-4-biphenylylsulphonyl)benzoyl]-4-(4-pyridyl)piperazine,
1-[4-(4-biphenylylsulphonyl)benzoyl]-4-(4-pyridyl)piperazine,
5-(6-chloronaphth-2-ylsulphonyl)-2-[4-(4-pyridyl)piperazin-1-ylcarbonyl]benzoic acid,
5-(2-naphthylsulphonyl)-2-[4-(4-pyridyl)piperazin-1-ylcarbonyl]benzoic acid,
5-(4'-bromo-4-biphenylylsulphonyl)-2-[4-(4-pyridyl)piperazin-1-ylcarbonyl]benzoic acid,
5-[(E)-4-chlorostyrrylsulphonyl]-2-[4-(4-pyridyl)piperazin-1-ylcarbonyl]benzoic acid,
1-{5-(6-bromonaphth-2-ylsulphonyl)-2-[4-(4-pyridyl)piperazin-1-ylcarbonyl]benzoyl}-piperidine,
1-{5-(6-chloronaphth-2-ylsulphonyl)-2-[4-(4-pyridyl)piperazin-1-ylcarbonyl]benzoyl}-piperidine,
1-{5-(4'-bromo-4-biphenylylsulphonyl)-2-[4-(4-pyridyl)piperazin-1-ylcarbonyl]benzoyl}-piperidine,
1-{5-[(E)-4-chlorostyrylsulphonyl]-2-[4-(4-pyridyl)piperazin-ylcarbonyl]benzoyl}-piperidine,
4'-bromo-N-{4-[1-(4-pyridyl)piperidin-4-yloxy]phenyl}-4-biphenylylsulphonamide,
4-chloro-N-{4-[1-(4-pyridyl)piperidin-4-yloxy]phenyl}-(E)-styrylsulphonamide,
5-bromo-N-{4-[1-(4-pyridyl)piperidin-4-yloxy]phenyl }-2-naphthalenesulphonamide,
N-{4-[1-(4-pyridyl)piperidin-4-yloxy]phenyl}-4-toluenesulphonamide,
N-{4-[1-(4-pyridyl)piperidin-4-yloxy]phenyl}-N-(4-tolylsulphonyl)-4-toluenesulphonamide,
4-chloro-N-methyl-N-{4-[1-(4-pyridyl)piperidin-4-yloxy]phenyl}-(E)-styrylsulphonamide,
4'-bromo-N-methyl-N-{4-[1-(4-pyridyl)piperidin-4-yloxy]phenyl}-4-biphenylylsulphonamide,
4'-bromo-N-{4-[1-(4-pyridyl)piperidin-4-ylmethoxy]phenyl}-4-biphenylylsulphonamide,
6-bromo-N-{4-[1-(4-pyridyl)piperidin-4-ylmethoxy]phenyl}-2-naphthalenesulphonamide,
4-chloro-N-{4-[1-(4-pyridyl)piperidin-4-ylmethoxy]phenyl}-(E)-styrylsulphonamide,
4'-bromo-N-(4'-bromo-4-biphenylylsulphonyl)-N-{4-[1-(4-pyridyl)piperidin-4-ylmethoxy]phenyl}-4-biphenylylsulphonamide,
6-bromo-N-(6-bromonaphth-2-ylsulphonyl)-N-{4-[1-(4-pyridyl)piperidin-4-ylmethoxy]phenyl}-2-naphthalenesulphonamide,
6-bromo-N-{3-[1-(4-pyridyl)piperidin-4-yloxy]phenyl}-2-naphthalenesulphonamide,
4-[4-chlorophenylsulphonyl)phenoxy]-1-(4-(pyridyl)piperidine,
5-(6-bromonaphth-2-ylsulphonyl)-2-[4-(4-pyridyl)piperazin-1-ylcarbonyl]benzoic acid,
4-(6-bromonaphth-2-ylsulphonyl)-2-[4-(4-pyridyl)piperazin-1-ylcarbonyl]benzoic acid,
1-[4-(4-(4-chlorophenoxy)phenylaminocarbonyl)benzyl]-4-(4-pyridyl)piperazine,
6-bromo-N-{2-[1-(4-pyridyl)piperidin-4-ylmethoxy]phenyl}-2-naphthalenesulphonamide,
4-chloro-N-{3-[1-(4-pyridyl)piperidin-4-yloxy]phenyl}-(E)-styrylsulphonamide,
4-[4-(6-bromonaphth-2-ylsulphonyl)phenoxy]-1-(4-pyridyl)piperidine,
4-[4-(6-bromonaphth-2-ylsulphonyl)benzoyl]-1-(4-pyridyl)piperidine,
4-[4-(6-bromonaphth-2-ylthio)benzoyl]-1-(4-pyridyl)piperidine,
1-[4-(6-bromonaphth-2-ylsulphonyl)phenylsulphonyl]-1-(4-pyridyl)piperazine,
6-(bromo-2-(4-(2-pyrimidin-4-yl)aminoethylaminocarbonyl)phenylsulphonyl)naphthalene,
1-[4-(6-bromonaphth-2-ylthio)benzoyl]-4-(4-pyridyl)piperazine,
1-[4-(6-bromonaphth-2-ylsulphonyl)benzoyl]-4-(4-pyridyl)piperazine,
1-[4-(6-bromonaphth-2-ylsulphonyl)benzoyl]-4-(4-pyrimidinyl)-piperazine,
1-[4-(6-bromonaphth-2-ylsulphonyl)benzoyl]-4-(4-pyridazinyl)piperazine,
1-[4-(6-bromonaphth-2-ylsulphonyl-2-trifluoromethylbenzoyl]-4-(4-pyridyl)piperazine,
1-[4-(6-bromonaphth-2-ylthio)-2-trifluoromethylbenzoyl]-4-(4-pyridyl)piperazine,
1-[4-(6-bromonaphth-2-ylthio)-2-carboxybenzoyl]-4-(4-pyridyl)piperazine
1-[5-(6-bromonaphth-2-ylthio)-2-carboxybenzoyl]-4-(4-pyridyl)piperazine,
1-[5-(6-bromonaphth-2-ylsulphonyl)-2-methoxycarbonylbenzoyl]-4-(4-pyridyl)piperazine,
1-[4-(6-bromonaphth-2-ylsulphonyl)-2-methoxycarbonylbenzoyl]-4-(4-pyridyl)piperazine,
1-[4-(6-bromonaphth-2-ylsulphonyl)-2-(2-(ethylthio)-ethylaminocarbonyl)benzoyl]-4-(4-pyridyl)piperazine,
1-[5-(6-bromonaphth-2-ylsulphonyl)-2-(2-ethylthio)ethylaminocarbonyl)benzoyl]-4-(4-pyridyl)piperazine,
1-[4-(6-bromonaphth-2-ylsulphonyl)-2-(piperidin-1-ylcarbonyl)-4-(4-pyridyl)piperazine,
1-[4-(6-bromonaphth-2-ylsulphonyl)-2-(piperidin-1-ylcarbonyl]-4-(4-pyridyl)piperazine,
1-[4-(4-(3-chlorophenyl)piperazin-1-ylsulphonyl)benzoyl]-4-(4-pyridyl)piperazine,
1-[4-(6-chloro-1,2,3,4-tetrahydroisoquinolin-2-ylsulphonylbenzoyl]-4-(4-pyridyl)piperazine,
1-(4-pyridyl)-(5-(6-methoxyindol-2-ylcarbonylamino)pyrid-2-yloxy)pyrrolidine, 1-[4-(6-bromonaphth-2-ylsulphonyl)benzoyl]-4-(2-methylpyrid-4-yl)piperazine, 1-[4-(6-bromonaphth-2-ylsulphonyl)benzoyl]-4-(4-pyridyl)hexahydro-1,4-diazepine, or a pharmaceutically-acceptable salt thereof.

An aminoheterocyclic derivative of the formula I, or pharmaceutically-acceptable salt thereof, may be prepared by any process known to be applicable to the preparation of structurally-related compounds. Such procedures are provided as a further feature of the invention and are illustrated by the following representative processes in which, unless otherwise stated $G^1$, $G^2$, m, $R^1$, $R^2$, $L^1$, $T^1$, $R^3$, $X^1$, Ar, $X^2$ and Q have any of the meanings defined hereinbefore, provided that when there is an amino, alkylamino, hydroxy or carboxy group in $R^1$, $L^1$, $R^2$, $R^3$, Ar or Q then any such group is protected by a conventional protecting group as necessary which may be removed when so desired by conventional means.

Necessary starting materials may be obtained by standard procedures of organic chemistry.

(a) For the production of those compounds of the formula I wherein $T^1$ is N and $X^1$ is CO, the reaction, conveniently in the presence of a suitable base, of an amine of the formula II

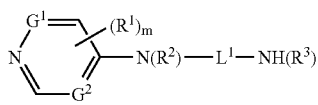

II with an acid of the formula III $HO_2C$—Ar—$X^2$—Q     III or a reactive derivative thereof.

A suitable reactive derivative of an acid of the formula III is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated ketone such as 1,1'-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

An analogous procedure may be employed for the preparation of those compounds of the formula I wherein $T^1$ is N and $X^1$ is a group of the formula $COC(R^4)_2$.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl. group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed. for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) For the production of those compounds of the formula I wherein $T^1$ is CH and $X^1$ is O or $C(R^4)_2O$, the reaction, conveniently in the presence of a suitable coupling agent, of a compound of the formula IV

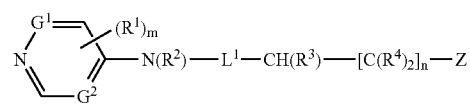

IV wherein n is 0 or 1 and Z is a displaceable group, with a phenolic compound the formula V HO—Ar—$X^2$—Q     V A suitable value for the displaceable group Z is, for example, a halogeno or sulphonyloxy group, for example a fluoro, chloro, bromo, mesyloxy or 4-tolylsulphonyloxy group.

A suitable reagent for the coupling reaction when Z is a halogeno or sulphonyloxy group is, for example, a suitable base, for example, an alkali or alkaline earth metal carbonate, hydroxide or hydride, for example sodium carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,N-dimethylformamide, N,N-dimethylacetamide, dimethylsulphoxide, acetone, 1,2-dimethoxyethane or tetrahydrofuran, and at a temperature in the range, for example, −10° to 150° C., conveniently at or near ambient temperature.

A suitable reagent for the coupling reaction of the alcohol of the formula IV wherein Z is a hydroxy group is, for example, the reagent obtained when said alcohol is reacted with a di-(1–4C)alkyl azodicarboxylate in the presence of a triarylphosphine or tri-(1–4C)alkylphosphine, for example with diethyl azodicarboxylate in the presence of triphenylphosphine or tributylphosphine. The reaction is preferably performed in a suitable inert solvent or diluent, for example acetone, 1,2-dimethoxyethane or tetrahydrofuran, and at a temperature in the range, for example, 10 to 80° C., conveniently at or near ambient temperature.

An analogous procedure may be employed for the preparation of those compounds of the formula I wherein $T^1$ is CH and $X^1$ is a group of the formula S or $C(R^4)_2S$.

(c) For the production of those compounds of the formula I wherein $T^1$ is N and $X^1$ is $CH(R^4)$, the reductive amination of a keto compound of the formula VI

$R^4$—CO—Ar—$X^2$—Q    VI with an amine of the formula VII

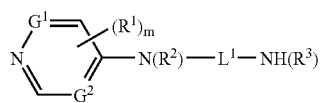

VII

Any reducing agent known in the art for promoting a reductive amination reaction may be employed. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride. The reaction is performed at a temperature in the range, for example, 10° to 80° C., conveniently at or near ambient temperature.

(d) For the production of those compounds of the formula I wherein $X^2$ is a group of the formula $N(R^7)SO_2$, the reaction, conveniently in the presence of a suitable base as defined hereinbefore, of an amine of the formula VIII

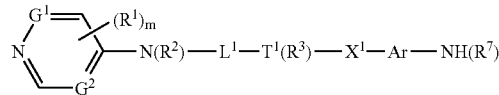

VIII with a compound of the formula IX

Z—$SO_2$—Q    IX wherein Z is a displaceable group as defined hereinbefore.

The reaction is conveniently performed in a suitable inert solvent or diluent as defined hereinbefore and at a temperature in the range, for example, 0° to 150° C., conveniently at or near ambient temperature.

An analogous procedure may be employed for those compounds of the formula I wherein $X^2$ is a group of the formula $N(R^7)CO$.

(e) For the production of those compounds of the formula I wherein $X^2$ is a group of the formula $N(R^7)SO_2$, the reaction, conveniently in the presence of a suitable base as defined hereinbefore, of a sulphonamide of the formula X

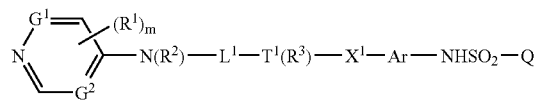

X with a compound of the formula XI $R^7$—Z    XI wherein Z is a displaceable group as defined hereinbefore.

The reaction is conveniently performed in a suitable inert solvent or diluent as defined hereinbefore and at a temperature in the range, for example, 0° to 150° C., conveniently at or near ambient temperature.

An analogous procedure may be employed for those compounds of the formula I wherein $X^2$ is a group of the formula $N(R^7)CO$.

(f) For the production of those compounds of the formula I wherein $X^2$ is a group of the formula $SO_2N(R^7)$ the reaction, conveniently in the presence of a suitable base as defined hereinbefore, of a compound of the formula XII

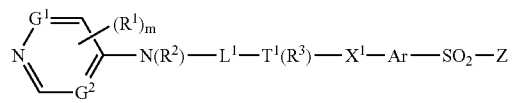

XII wherein Z is a displaceable group as defined hereinbefore, with an amine of the formula XIII $(R^7)NH$—Q    XIII The reaction is conveniently performed in a suitable inert solvent or diluent as defined hereinbefore and at a temperature in the range, for example, 0° to 150° C., conveniently at or near ambient temperature.

An analogous procedure may be employed for the preparation of those compounds of the formula I wherein $X^2$ is a group of the formula $CON(R^7)$.

(g) For the production of those compounds of the formula I wherein $T^1$ is CH and $X^1$ is a group of the formula $OC(R^4)_2$, the reaction conveniently in the presence of a suitable coupling agent as defined hereinbefore, of an alcohol of the formula XIV

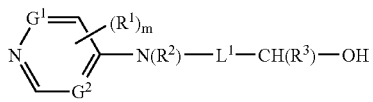   XIV with a compound of the formula XV

Z—C(R$^4$)$_2$—Ar—X$^2$—Q   XV wherein Z is a displaceable group as defined hereinbefore.

The reaction is conveniently performed in a suitable inert solvent or diluent as defined hereinbefore and at a temperature in the range, for example, 0° to 150° C., conveniently at or near ambient temperature.

An analogous procedure may be employed for the preparation of those compounds of the formula I wherein T$^1$ is CH and X$^1$ is a group of the formula SC(R$^4$)$_2$.

(h) For the production of those compounds of the formula I wherein X$^2$ is a group of the formula C(R$^6$)$_2$S, the reaction, conveniently in the presence of a suitable base as defined hereinbefore, of a compound of the formula XVI

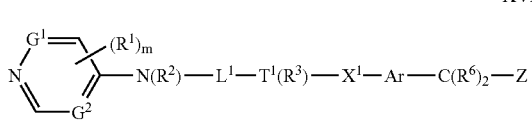   XVI wherein Z is a displaceable group as defined hereinbefore with a thiol of the formula XVII

HS—Q   XVII

The reaction is conveniently performed in a suitable inert solvent or diluent as defined hereinbefore and at a temperature in the range, for example, 0° to 150° C., conveniently at or near ambient temperature.

(i) For the production of those compounds of the formula I wherein L$^1$, R$^2$, R$^3$, Ar or Q bears a carboxy or carboxy-containing group, the hydrolysis of a compound of the formula I wherein L$^1$, R$^2$, R$^3$, Ar or Q bears a (1–4C) alkoxycarbonyl group.

The hydrolysis reaction may conveniently be carried out in a conventional manner using, for example, acidic or basic catalysis. A suitable acid for the acidic hydrolysis of an ester group is, for example, an inorganic acid such as hydrochloric or sulphuric acid. A suitable base for the basic hydrolysis of an ester group is, for example, an alkali or alkaline earth metal hydroxide such as sodium hydroxide or potassium hydroxide.

The reaction is conveniently performed in a suitable solvent or diluent such as an alcohol, for example methanol or ethanol, and at a temperature in the range, for example 0° to 120° C., conveniently in the range of 15° to 60° C.

(j) For the production of those compounds of the formula I wherein L$^1$, R$^2$, R$^3$, Ar or Q bears a carbamoyl, N-alkylcarbamoyl, N,N-dialkylcarbamoyl or other aminocarbonyl group for example piperidinocarbonyl or 2-(ethylthio)aminoethylaminocarbonyl, the reaction of a compound of the formula I wherein L$^1$, R$^2$, R$^3$, Ar or Q bears a carboxy group, or a reactive derivative thereof as defined hereinbefore, with ammonia, an alkylamine, dialkylamine or an appropriate amino compound.

The reaction is conveniently performed in a suitable inert solvent or diluent as defined hereinbefore and at a temperature in the range, for example, 0° to 120° C., conveniently in the range 15° to 60°.

Similarly compounds of the formula I bearing ester groups may be prepared by esterification of the corresponding carboxy compound.

(k) For the production of those compounds of the formula I wherein X$^1$ is a group of the formula SO, SO$_2$, C(R$^4$)$_2$SO, C(R$^4$)$_2$SO$_2$, SOC(R$^4$)$_2$ or SO$_2$C(R$^4$)$_2$, wherein Ar bears a (1–4C)alkylsulphinyl, (1–4C)alkylsulphonyl, 1-oxothiamorpholino or 1,1-dioxothiamorpholino group or a substituent which contains a (1–4C)alkylsulphinyl, (1–4C) alkylsulphonyl, 1-oxothiamorpholino or 1,1-dioxothiamorpholino group, wherein X$^2$ is a group of the formula SO, SO$_2$, C(R$^6$)$_2$SO or C(R$^6$)$_2$SO$_2$, or wherein Q bears a (1–4C)alkylsulphinyl, (1–4C)alkylsulphonyl, phenylsulphinyl, phenylsulphonyl, heteroarylsulphinyl or heteroarylsulphonyl group, the oxidation of the corresponding compound of the formula I which contains a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(l) The reaction of an activated derivative of a compound of the formula XVIII:

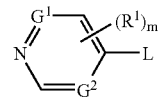   XVIII wherein L is a displaceable group as hereinbefore defined with a compound of the formula XIX:

NH(R$^2$)—L$^1$—T$^1$(R$^3$)—X$^1$—Ar—X$^2$—Q   XIX

Typically L is halo for example fluoro or chloro and the reaction is performed in a substantially inert solvent, as hereinbefore defined, at an ambient or elevated temperature, and in the presence of a suitable base for example an organic amine such as triethylamine.

The compounds of the formula II–XIX inclusive are useful intermediates in the processes for making the compounds of the formula I. In another aspect the present invention provides novel compounds and classes of compound within the generic formulae II–XIX inclusive.

The compounds of the formula II–XIX inclusive may be prepared by any process known to be applicable to the preparation of structurally related compounds, for example, where applicable, by methods related to those described hereinbefore for preparing compounds of the formula I. Particular reference may be made to the methods of the Examples described hereinafter.

Intermediates of particular interest include those of the formula XX and XXI:

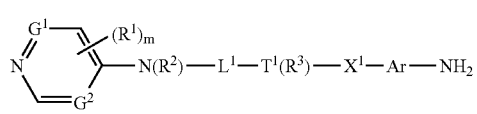

XX

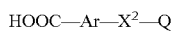

HOOC—Ar—X²—Q    XXI and active derivatives thereof, wherein $G^1$, $G^2$, $R^1$, m, $R^2$, $L^1$, $T^1$, $R^3$, $X^1$, Ar, $X^2$ and Q are as defined in relation to formula I.

When a pharmaceutically-acceptable salt of a compound of the formula I is required, it may be obtained, for example, by reaction of said compound with a suitable acid or base using a conventional procedure.

When an optically active form of a compound of the formula I is required. it may be obtained, for example, by carrying out one of the aforesaid procedures using an optically active starting material or by resolution of a racemic form of said compound using a conventional procedure.

As stated previously, the compounds of the formula I are inhibitors of the enzyme Factor Xa. The effects of this inhibition may be demonstrated using one or more of the standard procedures set out hereinafter:

a) Measurement of Factor Xa Inhibition

An in vitro assay system was carried out based on the method of Kettner et al., *J. Biol. Chem.*, 1990, 265, 18289–18297, whereby various concentrations of a test compound were dissolved in DMSO and diluted in a pH7.5 buffer containing 0.5% of a polyethylene glycol (PEG 6000) and incubated at 37° C. with human Factor Xa (0.001 Units/ml, 0.3 ml) for 15 minutes. The chromogenic substrate S-2765 (KabiVitum AB, 20 μM) was added and the mixture was incubated at 37° C. for 20 minutes whilst the absorbance at 405 nm was measured. The maximum reaction velocity (Vmax) was determined and compared with that of a control sample containing no test compound. Inhibitor potency was expressed as an $IC_{50}$ value.

b) Measurement of Thrombin Inhibition

The procedure of method a) was repeated except that human thrombin (0.005 Units/ml) and the chromogenic substrate S-2238 (KabiVitum AB, 7 μM) were employed.

c) Measurement of Anticoagulant Activity

An in vitro assay whereby human, rat or rabbit venous blood was collected and added directly to a sodium citrate solution (3.2 g/100 ml, 9 parts blood to 1 part citrate solution). Blood plasma was prepared by centrifugation (1000 g, 15 minutes) and stored at 2–4° C. Conventional prothrombin time (PT) tests were carried out in the presence of various concentrations of a test compound and the concentration of test compound required to double the clotting time, hereinafter referred to as CT2, was determined. In the PT test, the test compound and blood plasma were incubated at 37° C. for 10 minutes. Tissue thromboplastin with calcium (Sigma Limited, Poole, England) was added and fibrin formation and the time required for a clot to form were determined.

d) An ex vivo Assay of Anticoagulant Activity

The test compound was administered intravenously or orally to a group of Alderley Park Wistar rats. At various times thereafter animals were anaesthetised, blood was collected and PT coagulation assays analogous to those described hereinbefore were conducted. In addition the plasma concentration of compounds is determined by comparison with the anti-Factor Xa activity of a standard compound.

e) An in vivo Measurement of Antithrombotic Activity

Thrombus formation was induced using an analogous method to that described by Vogel et al., *Thromb. Research*, 1989, 54, 399–410. A group of Alderley Park Wistar rats was anaesthetised and surgery was performed to expose the vena cava. Collateral veins were ligated and two loose sutures were located, 0.7 cm apart, round the inferior vena cava. Test compound was administered intravenously or orally. At an appropriate time thereafter tissue thromboplastin (30 μl/kg) was administered via the jugular vein and, after 10 seconds, the two sutures were tightened to induce stasis within the ligated portion of vena cave After 10 minutes the ligated tissue was excised and the thrombus therein was isolated, blotted and weighed.

f) An in vivo Measurement of Antithrombotic Activity

Using a method similar to that of Smith J R et al Br. J Pharmacol. 1982, 77: 29–38, fasted male Alderley Park rats (360–410 g) are pre-dosed at various times by oral (5 ml/kg) or subcutaneous (1 ml/kg) routes before being anaesthetised with Intraval (120 mg/kg i.p.). The left jugular vein and the right carotid artery are exposed and cannulated with a polypropylene catheters 12 cm in length. An arterio-venous shunt is completed by connecting the two catheters with a 6 cm length of tubing (i.d. 0.3 cm) which contains a 5 cm length of pre-weighed cotton. All tubes were filled with saline prior to the establishment of the circuit. Clamps are removed from the catheters and blood is allowed to flow through the polypropylene tubing for 20 mins. During this time the effect of the test compound on template bleeding time is assessed. The shunt is then closed and the thrombus which has developed on the cotton thread is removed, blotted dry and weighed. Blood samples are also taken at this point by cardiac puncture into 3.2% tri-sodium citrate, plasma is prepared by centrifugation (5 mins 20000 g) and frozen for subsequent prothrombin time and drug level determinations.

The plasma concentration of the compound is extrapolated from the standard curve and expressed in Anti-Factor Xa units. Thrombus weight is measured following dosing of vehicle or test compound. Data is expressed as % inhibition of thrombus formation in the presence of compound when compared to thrombus weight from a group of control animals.

Although the pharmacological potencies of the compounds of formula I vary with structural changes as expected, in general compounds of the formula I possess activity at the following concentrations or doses in at least one of the above tests a) to c):

test a): $IC_{50}$ (Factor Xa) in the range, for example, 0.001–25 μM;

test b): $IC_{50}$ (thrombin), for example, greater than 40 μM;

test c): CT2 (PT) in the range, for example, 0.1–50 μM.

By way of example, the compound of Example I as disclosed hereinafter has an $IC_{50}$ of 0.013 μM against Factor Xa in test a), an $IC_{50}$ of greater than 40 μM against thrombin in test b) and a CT2 (PT) of 5 μM in test c).

According to a further feature of the invention there is provided a pharmaceutical composition which comprises an aminoheterocyclic derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is an aminoheterocyclic derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided an aminoheterocyclic derivative of the formula I, or a pharmaceutically-acceptable salt thereof, for use in a method of treatment of the human or animal body by therapy.

The invention also includes the use of such an active ingredient in the production of a medicament for use in:
  (i) producing a Factor Xa inhibitory effect;
  (ii) producing an anticoagulant effect;
  (iii) producing an antithrombotic effect;
  (iv) treating a Factor Xa mediated disease or medical condition;
  (v) treating a thrombosis mediated disease or medical condition;
  (vi) treating coagulation disorders; and/or
  (vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula I will naturally vary according to the nature and severity of the medical condition, the age and sex of the animal or patient being treated and the route of administration, according to well known principles of medicine. As mentioned above, compounds of the formula I are useful in the treatment or prevention of a variety of medical disorders where anticoagulant therapy is indicated. In using a compound of the formula I for such a purpose, it will generally be administered so that a daily dose in the range, for example, 0.5 to 500 mg/kg body weight is received, given if required in divided doses. In general lower doses will be administered when a parenteral route is employed, for example a dose for intravenous administration in the range, for example, 0.5 to 50 mg/kg body weight will generally be used. For preferred and especially preferred compounds of the invention, in general, lower doses will be employed, for example a daily dose in the range, for example, 0.5 to 10 mg/kg body weight.

Although the compounds of the formula I are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

The invention will now be illustrated in the following Examples in which, unless otherwise stated:
  (i) evaporations were carried out by rotary evaporation in vacuo and work-up procedures were carried out after removal of residual solids by filtration;
  (ii) operations were carried out at room temperature, that is in the range 18–25° C. and under an atmosphere of an inert gas such as argon;
  (iii) column chromatography (by the flash procedure) and medium pressure liquid chromatography (MPLC) were generally performed on Merck Kieselgel silica (Art. 9385) or Merck Lichroprep RP-18 (Art. 9303) reversed-phase silica obtained from E. Merck, Darmstadt, Germany; alternatively high pressure liquid chromatography (HPLC) was performed on a Dynamax C-18 60 Å preparative reversed-phase column;
  (iv) yields are given for illustration only and are not necessarily the maximum attainable;
  (v) the end-products of the formula I have satisfactory microanalyses and their structures were confirmed by nuclear magnetic resonance (NMR) at 200, 250 or 300 MHz and mass spectral techniques; unless otherwise stated, $CD_3SOCD_3$ solutions of the end-products of the formula I were used for the determination of NMR spectral data, chemical shift values were measured on the delta scale; the following abbreviations have been used: s, singlet; d, doublet; t, triplet; q, quartet; m, multiplet;
  (vi) intermediates were not generally fully characterised and purity was assessed by thin layer chromatographic, infra-red (IR) or NMR analysis;
  (vii) melting points were determined using a Mettler SP62 automatic melting point apparatus or an oil-bath apparatus; melting points for the end-products of the formula I were generally determined after crystallisation from a conventional organic solvent such as ethanol, methanol, acetone, ether or hexane, alone or in admixture; and
  (viii) the following abbreviations have been used:
    DMF N,N-dimethylformamide;
    TBF tetrahydrofuran;
    DMSO dimethylsulphoxide.

EDAC 1-(3-dimethylaminopropyl)-3-ethylcarbodiimide hydrochloride
BOC tert-butyloxycarbonyl

EXAMPLE 1

1,1'-Carbonyldiimidazole (0.15 g) was added to a stirred solution of 4-(6-chloronaphth-2-ylsulphonyl)benzoic acid (0.29 g) in DMF (10 ml) which had been cooled to 0° C. and the mixture was stirred at 0° C. for 30 minutes. N-(4-Pyridyl)piperazine (0.164 g) was added, the cooling bath was removed and the mixture was stirred at ambient temperature for 16 hours. The solvent was removed by evaporation and the residue was partitioned between ethyl acetate and water. The ethyl acetate extract was washed with water and with brine, dried (MgSO4) and evaporated. The residue was triturated under diethyl ether to give 1-[4-(6-chloronaphth-2-ylsulphonyl)benzoyl]-4-(4-pyridyl)piperazine (0.085 g), m.p. 267–269° C.;

NMR Spectrum 3.25–3.5 (m, 6H), 3.6–3.9 (m, 2H), 6.75 (d, 2H), 7.65 (d, 2H), 7.77 (m, 1H), 8.0 (m, 1H), 8.05–8.25 (m, 6H), 8.3 (d, 1H), 8.6 (s,1H);

Mass Spectrum m/z 492 (M+H);

Elemental Analysis Found C, 63.1; H, 4.7; N, 8.2. C26H22ClN3O3S 2H2O requires C, 63.5; H, 4.5; N, 8.5%.

The 4-(6-chloronaphth-2-ylsulphonyl)benzoic acid used as a starting material was prepared as follows:

A solution of sodium nitrite (2.7 g) in water (5 ml) was added during 2 hours to a stirred mixture of 6-amino-2-naphthalenesulphonic acid (8.8 g), dilute aqueous hydrochloric acid (2.8% weight/volume, 20 ml) and water (15 ml) which had been cooled to 0° C. The mixture was stirred at 0° C. for 30 minutes and then poured onto a stirred suspension of cuprous chloride (3.96 g) in dilute aqueous hydrochloric acid (2.8%, 20 ml). The mixture was evaporated to give 6-chloro-2-naphthalenesulphonic acid which was used without further purification.

The material was suspended in DMF (40 ml) and cooled to 5° C. Thionyl chloride (8.6 ml) was added dropwise and the mixture was stirred at 5° C. for 3 hours. The mixture was poured onto ice and extracted with methylene chloride. The organic solution was dried (MgSO4) and evaporated. The residue was purified by column chromatography using a 20:1 mixture of hexane and ethyl acetate as eluent There was thus obtained 6-chloronaphth-2-ylsulphonyl chloride (2.49 g);

NMR Spectrum 7.45 (m, 1H), 7.8 (m, 1H), 7.85 (d, 1H), 8.05 (m, 2H), 8.2 (s,1H).

6-Chloronaphth-2-ylsulphonyl chloride (2.61 g) was added in one portion to a stirred mixture of sodium sulphite heptahydrate (4.71 g), sodium bicarbonate (1.64 g) and water (25 ml) which had been heated to 70° C. The resultant mixture was heated to that temperature for 3 hours and then allowed to cool slowly to ambient temperature. The crystalline precipitate was isolated giving sodium 6-chloronaphth-2-ylsulphinate (2.4 g) which was used without further purification.

A mixture of a portion (0.5 g) of the material so obtained, 4-fluorobenzaldehyde (0.25 g) and DMSO (10 ml) was stirred and heated to 110° C. for 5 hours. A second portion (0.5 g) of the sodium 6-chloronaphth-2-ylsulphinate was added and the mixture was heated to 110° C. for a further 10 hours. The mixture was cooled to ambient temperature and partitioned between ethyl acetate and water. The organic extract was washed with water and with brine, dried (MgSO4) and evaporated. The residue was purified by column chromatography using a 1:1 mixture of hexane and ethyl acetate as eluent. There was thus obtained 4-(6-chloronaphth-2-ylsulphonyl)benzaldehyde (0.25 g);

NMR Spectrum 7.7 (m, 1H), 8.0 (m, 1H), 8.1–8.3 (m, 7H), 8.8 (s,1H), 10.0 (s, 1H).

After repetition of the previous steps, potassium permanganate (0.4 g) was added in small portions during 1 hour to a stirred mixture of 4-(6-chloronaphth-2-ylsulphonyl)benzaldehyde (0.58 g), cetyltrimethylammonium bromide (0.056 g) and water (25 ml) which had been heated to 60° C. The mixture was heated to 60° C. for a further 2 hours. The mixture was cooled to ambient temperature and acidified by the addition of 2M aqueous hydrochloric acid. Ethyl acetate was added. The mixture was filtered through a pad of diatomaceous earth. The solid was washed thoroughly in turn with methylene chloride and with ethyl acetate. The organic solutions were combined, dried (MgSO4), and evaporated. The residue was purified by column chromatography using increasingly polar mixtures of methylene chloride and methanol as eluent. There was thus obtained 4-(6-chloronaphth-2-ylsulphonyl)benzoic acid (0.376 g);

NMR Spectrum 7.7 (m, 1H); 7.95 (m,1H); 8.1–8.2(m, 6H); 8.6 (s,1H).

EXAMPLE 2

Using an analogous procedure to that described in Example 1, N-(4-pyridyl)piperazine was reacted with 4-(2-naphthylsulphonyl)benzoic acid to give 1-[4-(2-naphthylsulphonyl)benzoyl]-4-(4-pyridyl)piperazine in 32% yield;

NMR Spectrum 3.25–3.5 (m, 6H), 3.6–3.9 (m, 2H), 6.8 (d, 2H), 7.7 (d, 2H), 7.77 (m, 1H), 7.95 (m, 1H), 8.05–8.25 (m, 8H), 8.77 (d, 1H);

Mass Spectrum m/z 457 (M+H);

Elemental Analysis Found C, 63.5; H, 5.5; N, 8.6. C26H23N3O3S 2H2O requires C, 63.5; H, 5.5; N, 8.6%.

The 4-(2-naphthylsulphonyl)benzoic acid used as a starting material was prepared from 4-fluorobenzaldehyde and sodium 2-naphthylsulphinate using analogous procedures to those described in the fourth and fifth paragraphs of the portion of Example 1 which is concerned with the preparation of starting materials. There was thus obtained 4-(2-naphthylsulphonyl)benzoic acid in 28% yield;

NMR Spectrum 7.7 (m, 1H), 7.95 (m, 1H), 8.1–8.2 (m, 8H), 8.7 (d, 1H).

EXAMPLE 3

Glacial acetic acid (0.178 g) was added to a mixture of N-(4-pyridyl)piperazine (0,121 g), 4-(6-bromonaphth-2-ylsulphonyl)benzaldehyde (0.278 g) and methylene chloride (10 ml) and the mixture was stirred at ambient temperature for 30 minutes. Sodium triacetoxyborohydride (0.236 g) was added and the mixture was stirred at ambient temperature for 16 hours. Water (50 ml) was added and the mixture was acidified by the addition of 2M aqueous hydrochloric acid. The resultant mixture was washed with diethyl ether. The aqueous phase was basified by the addition of 2M aqueous sodium hydroxide solution and extracted with methylene chloride. The resultant organic phase was dried (MgSO4), and evaporated. The residue was purified by column chromatography using increasingly polar mixtures of methylene chloride and methanol as eluent. There was thus obtained 1-[4-(6-bromonaphth-2-ylsulphonyl)benzyl]-4-(4-pyridyl)piperazine (0.127 g) as a gum;

NMR Spectrum 3.2–3.4 (m, 8H), 3.6 (s, 2H), 6.75 (d, 2H), 7.6 (d, 2H), 7.75 (m, 1H), 7.95 (m, 3H), 8.1–8.2 (m, 4H), 8.3 (d, 1H), 8.75 (s, 1H);

Mass Spectrum m/z 522 (M+H);

Elemental Analysis Found C, 58.6; H, 4.5; N, 7.8. C26H24BrN3O2S 0.15CH2Cl2 requires C, 58.7; H, 4.6; N, 7.9%.

The 4-(6-bromonaphth-2-ylsulphonyl)benzaldehyde used as a starting material was obtained as follows:

6-Bromonaphth-2-ylsulphonyl chloride was obtained in 22% yield from 6-amino-2-naphthalenesulphonic acid using an analogous procedure to that described in the first two paragraphs of the portion of Example 1 which is concerned with the preparation of starting materials except that hydrobromic acid and cuprous bromide were used in place of hydrochloric acid and cuprous chloride respectively. The material gave the following NMR signals: 7.65 (m, 1H), 7.75–8.0 (m, 3H), 8.15–8.2 (m, 2H).

6-Bromonaphth-2-ylsulphonyl chloride (9.4 g) was added in small portions over 3 hours to a stirred mixture of sodium sulphite heptahydrate (14.46 g), sodium bicarbonate (5.08 g) and water (100 ml) which had been heated to 70° C. The resultant mixture was allowed to cool slowly to ambient temperature. The crystalline precipitate was isolated giving sodium 6-bromonaphth-2-ylsulphinate (8.07 g) which was used without further purification.

A mixture of a portion (1.47 g) of the material so obtained, 4-fluorobenzaldehyde (0.72 g) and DMSO (20 ml) was stirred and heated to 110° C. for 4 hours and at 80° C. for 12 hours. The mixture was cooled to ambient temperature and partitioned between ethyl acetate and water. The organic extract was washed with water and with brine, dried (MgSO4) and evaporated. The residue was purified by column chromatography using increasingly polar mixtures of hexane and ethyl acetate as eluent. There was thus obtained 4-(6-bromonaphth-2-ylsulphonyl)benzaldehyde (0.28 g);

NMR Spectrum 7.8 (m, 1H), 8.0 (m, 1H), 8.1–8.2 (m, 6H), 8.4 (d,1H), 8.8 (s,1H),10.1 (s, 1H).

EXAMPLE 4

A solution of 4'-bromo-4-biphenylylsulphonyl chloride (0.33 g) in methylene chloride (5 ml) was added dropwise to a stirred solution of 4-[-(4-pyridyl)piperidin-4-yloxy]aniline (0.269 g) in methylene chloride (20 ml) and the mixture was stirred at ambient temperature for 16 hours. The precipitated solid was collected by filtration and triturated under methanol (5 ml). The resultant solid was washed with diethyl ether. There was thus obtained 4'-bromo-N-{4-[1-(4-pyridyl)piperidin-4-yloxy]phenyl}-4-biphenylylsulphonamide, hydrochloride salt, (0.508 g), m.p. 302–304° C.;

NMR Spectrum 1.66 (m, 2H), 1.99 (m, 2H), 3.58 (m, 2H), 3.86 (m, 2H), 4.60 (m, 1H), 6.89 (d, 2H), 7.03 (d, 2H), 7.18 (d, 2H) 7.67 (s, 4H), 7.76 (d, 2H), 7.84 (d, 2H), 8.19 (d, 2H), 10.05 (s, 1H);

Mass Spectrum m/z 564/566 (M+H);

Elemental Analysis Found C, 54.6; H, 4.7; N, 6.9; S, 5.2. C28H26BrN3O3S 1HCl 1H2O requires C, 54.3; H, 4.7; N, 6.8; S, 5.2%.

The 4-[1-(4-pyridyl)piperidin-4-yloxy]aniline used as starting material was obtained as follows:

1,1'-(Azodicarbonyl)dipiperidine (20.03 g), tributylphosphine (16.06 g) and 1-(4-pyridyl)piperidin-4-ol (Chemical Abstracts, vol. 113, abstract 231211n; European Patent Application No. 0 359 389; 9.43 g) were added in turn to a stirred solution of 4-(N-tert-butoxycarbonylamino)phenol (J. Med. Chem., 1995, 29, 3983; 11.08 g) in THF (300 ml) which was cooled to 10° C. The mixture was stirred at ambient temperature for 20 hours. The precipitate was removed by filtration and the filtrate was evaporated. The residue was purified by column chromatography using initially ethyl acetate and then increasingly polar mixtures of methylene chloride and methanol as eluent. There was thus obtained tert-butyl N-{4-[1-(4-pyridyl)piperidin-4-yloxy]phenyl}carbamate (7.38 g), m.p. 192–195° C., which was used without further purification.

A solution of a portion (4.22 g) of the material so obtained in methylene chloride (400 ml) was treated with a saturated solution of hydrogen chloride in diethyl ether (50 ml). The mixture was stirred at ambient temperature for 64 hours. The mixture was evaporated and the residue was crystallised under a mixture of diethyl ether and methanol to give the hydrochloride salt of the required starting material (2.85 g), m.p. 289–291° C. A portion (1.5 g) of the material was dissolved in water (10 ml) and a 2M aqueous sodium hydroxide solution was added until precipitation was complete. There was thus obtained 4-[1-(4-pyridyl)piperidin-4-yloxy]aniline (1.03 g), m.p. 214–215° C.;

NMR Spectrum 1.57 (m, 2H), 1.86 (m, 2H), 3.24 (m, 2H), 3.67 (m, 2H), 4.31 (m, 1H), 6.47 (d, 2H), 6.66 (d, 2H), 6.87 (d, 2H), 8.13 (d, 2H).

The 4'-bromo-4-biphenylylsulphonyl chloride used as a starting material was obtained as follows:

Chlorosulphonic acid (8.3 ml) was added dropwise to a stirred solution of 4-bromobiphenyl (23.3 g) in chloroform (200 ml) and the mixture was stirred at ambient temperature for 30 minutes. The precipitate was isolated and washed with chloroform. There was thus obtained 4'-bromo-4-biphenylylsulphonic acid (30.3 g).

Thionyl chloride (21.2 ml) was added dropwise to a stirred solution of 4'-bromo-4-biphenylylsulphonic acid (30.3 g) in DMF (120 ml) which had been cooled to 5° C. The mixture was stirred at ambient temperature for 3 hours. The mixture was poured into a mixture of ice and water (1L) and the resultant precipitate was isolated, dissolved in diethyl ether, dried (MgSO4) and re-isolated by evaporation of the solvent. There was thus obtained 4'-bromo-4-biphenylyl-sulphonyl chloride (24.1 g) [after crystallisation of the residue from a 1:1 mixture of isohexane and toluene], m.p. 125–127° C.

EXAMPLE 5

Using an analogous procedure to that described in Example 4, 4-[1-(4-pyridyl)piperidin-4-yloxy]aniline was reacted with (E)-4-chlorostyrylsulphonyl chloride. The reaction product was purified by column chromatography on a C-18 60 Å preparative reversed-phase HPLC column using 0.1% trifluoroacetic acid in aqueous acetonitrile and a gradient of 30% to 70% acetonitrile as eluent. There was thus obtained 4-chloro-N-{4-[1-(4-pyridyl)piperidin-4-yloxy]phenyl}-(E)-styrylsulphonamide, trifluoroacetate salt, as a gum in 10% yield;

NMR Spectrum 1.64 (m, 2H), 1.99 (m, 2H), 3.62 (m, 2H), 3.91 (m, 2H), 4.64 (m, 1H), 6.82–7.42 (m, 8H), 7.46 (d, 2H), 7.72 (d, 2H), 8.23 (d, 2H), 9.75 (s,1H);

Mass Spectrum m/z 470/472 (M+H).

The (E)-4-chlorostyrylsulphonyl chloride used as a starting material was obtained as follows:

Sulphuryl chloride (1.37 ml) was added dropwise to DMF (1.55 ml) which was stirred and cooled to a temperature in the range 0 to 5° C. The mixture was then stirred at ambient temperature for 30 minutes. 4-Chlorostyrene (1.2 ml) was added and the mixture was stirred and heated to 90° C. for 3.5 hours. The mixture was cooled to ambient temperature and poured onto a mixture (25 ml) of ice and water. The precipitate was isolated, washed with water and dried. There was thus obtained (E)-4-chloro-β-styrylsulphonyl chloride (1.8 g);

NMR Spectrum 6.95 (s, 2H), 7.4 (d, 2H), 7.55 (d, 2H).

EXAMPLE 6

6-Bromonaphth-2-ylsulphonyl chloride (0.1 g) was added to a mixture of 4-[1-(4-pyridyl)piperidin-4-yloxy]aniline (0.1 g), triethylamine (0.168 g) and methylene chloride (5 ml) and the mixture was stirred at ambient temperature for 16 hours. The mixture was evaporated and the residue was purified on a C-18 60 Å preparative reversed-phase HPLC column using 0.1% trifluoroacetic acid in aqueous acetonitrile and a gradient of 60% to 95% acetonitrile as eluent. There were thus obtained in turn: 6-bromo-N-{4-[1-(4-pyridyl)piperidin-4-yloxy]phenyl}-2-naphthalenesulphonamide, trifluoroacetate salt, as a gum (0.026 g);

NMR Spectrum 1.64 (m, 2H), 1.97 (m, 2H), 3.57 (m, 2H), 3.87 (m, 2H), 4.58 (m, 1H), 6.83 (d, 2H) 6.99 (d, 2H), 7.19 (d, 2H), 7.75 (q, 1H), 7.80 (q, 1H), 8.07 (d, 2H), 8.20 (d, 2H), 8.33 (d, 2H), 10.07 (s, 1H), 13.27 (broad s, 1H);

Mass Spectrum m/z 538/540 (M+H); and 6-bromo-N-{4-[1-(4-pyridyl)piperidin-4-yloxy]phenyl}-N-(6-bromonaphth-2-ylsulphonyl)-2-naphthalenesulphonamide, trifluoroacetate salt, as a waxy solid (0.031 g), m.p. 130–135° C.;

NMR Spectrum 1.67 (m, 2H), 2.07 (m, 2H), 3.62 (m, 2H), 3.94 (m, 2H), 4.76 (m, 1H), 6.99 (m, 4H), 7.22 (d, 2H), 7.86 (m, 4H), 8.06–8.27 (m, 6H), 8.45 (d, 4H);

Mass Spectrum m/z 808 (M+H).

EXAMPLE 7

Using an analogous procedure to that described in Example 4, 4-[1-(4-pyridyl)piperidin-4-yloxy]aniline was reacted with 4-toluenesulphonyl chloride to give N-{4-[1-(4-pyridyl)piperidin-4-yloxy]phenyl}-4-toluenesulphonamide, hydrochloride salt, in 54% yield, m.p. 270–272° C.;

NMR Spectrum 1.63 (m, 2H), 1.97 (m, 2H), 2.31 (s, 3H), 3.57 (m, 2H), 3.88 (m, 2H), 4.60 (m, 1H), 6.84 (d, 2H), 6.98 (d, 2H), 7.20 (d, 2H), 7.31 (d, 2H), 7.57 (d, 2H), 8.19 (d, 2H), 9.88 (s, 1H);

Mass Spectrum m/z 424 (M+H);

Elemental Analysis Found C, 57.7; H, 5.5; N, 8.7. $C_{23}H_{25}N_3O_3S$ 1HCl $H_2O$ requires; C, 57.8; H, 5.9; N, 8.8%.

EXAMPLE 8

Using an analogous procedure to that described in Example 6, N-{4-[1-(4-pyridyl)piperidin-4-yloxy]phenyl}-4-toluenesulphonamide, hydrochloride salt, was reacted with 4-toluenesulphonyl chloride. The crude reaction product was triturated under water. There was thus obtained N-{4-[1-(4-pyridyl)piperidin-4-yloxy]phenyl}-N-(4-tolylsulphonyl)-4-toluenesulphonamide in 85% yield, m.p. 196–198° C.;

NMR Spectrum 1.65 (m, 2H), 2.02 (m, 2H), 2.46 (s, 6H), 3.20 (m, 2H), 3.72 (m, 2H), 4.68 (m, 1H), 6.84 (m, 4H), 7.02 (d, 2H), 7.48 (d, 4H), 7.68 (d, 4H), 8.16 (d, 2H);

Mass Spectrum m/z 578 (M+H).

EXAMPLE 9

Sodium hydride (60% dispersion in mineral oil, 0.06 g) was added to a stirred mixture of 4'-bromo-N-{4-[1-(4-pyridyl)piperidin-4-yloxy]phenyl}-4-biphenylylsulphonamide, hydrochloride salt (0.309 g), THF (10 ml) and DMF (1 ml), and the mixture was stirred at ambient temperature for 45 minutes. Methyl iodide (0.142 g) was added and stirring was continued for 16 hours. The mixture was evaporated. The residue was triturated under water and the resultant solid was purified by column chromatography using increasingly polar mixtures of methylene chloride and methanol as eluent. There was thus obtained 4'-bromo-N-methyl-N-{4-[1-(4-pyridyl)piperidin-4-yloxy]phenyl}-4-biphenylylsulphonamide, as a foam (0.045 g);

NMR Spectrum (CDCl$_3$) 2.00 (m, 4H), 3.20 (s, 3H), 3.41 (m, 2H), 3.65 (m, 2H), 4.57 (m, 1H), 6.74 (d, 2H), 6.84 (d, 2H), 7.05 (d, 2H), 7.47 (d, 2H), 7.61 (m, 6H), 8.25 (d, 2H);

Mass Spectrum m/z 578/580 (M+H).

EXAMPLE 10

Using an analogous procedure to that described in Example 4, N-methyl-4-[1-(4-pyridyl)piperidin-4-yloxy] aniline was reacted with (E)-4-chlorostyrylsulphonyl chloride. The yellow reaction liquor was decanted from a brown gum (which was discarded) and evaporated. The resultant foam was purified by column chromatography on alumina (ICN alumina N, grade 3) using methylene chloride as eluent. There was thus obtained 4-chloro-N-methyl-N-{4-[1-(4-pyridyl)piperidin-4-yloxy]phenyl}-(E)-styrylsulphonamide, as a gum in 34% yield;

NMR Spectrum 1.63 (m, 2H), 1.97 (m, 2H), 2.25 (m, 2H), 3.19 (s, 3H), 3.68 (m, 2H), 4.62 (m, 1H), 6.80 (d, 2H), 6.96 (d, 2H), 7.25 (d, 2H) 7.26 (d, 1H), 7.36 (d, 1H), 7.47 (d, 2H), 7.76 (d, 2H), 8.12 (d, 2H);

Mass Spectrum m/z 484/486 (M+H).

The N-methyl-4-[1-(4-pyridyl)piperidin-4-yloxy]aniline used as a starting material was prepared as follows:

Acetic formic anhydride (1.5 g; pre-formed by heating acetic anhydride and 98% formic acid at 60° C. for 2 hours) was cooled to 5° C. and 4-[1-(4-pyridyl)piperidin-4-yloxy] aniline (1.0 g) was added. The mixture was stirred at ambient temperature for 16 hours and then evaporated. The residue was dissolved in water (50 ml) and the mixture was basified to pH10 by the addition of a 2M aqueous sodium hydroxide solution. The resultant mixture was extracted with methylene chloride, washed with water and with brine, dried (MgSO4) and evaporated to give N-{4-[1-(4-pyridyl) piperidin-4-yloxy]phenyl}formamide as a foam (0.72 g);

NMR Spectrum 1.63 (m, 2H), 1.96 (m, 2H), 3.22 (m, 2H), 3.67 (m, 2H), 4.56 (m, 1H), 6.82 (d, 2H), 6.94 (d, 2H), 7.48 (d, 2H), 8.12 (d, 2H), 8.20 (d, 1H), 9.96 (broad s, 1H);

Mass Spectrum m/z 298 (M+H).

The material so formed was dissolved in THF (5 ml) and added to a stirred suspension of lithium aluminium hydride (0.18 g) in THF (5 ml). The mixture was stirred at ambient temperature for 16 hours. The minimum volume of a saturated aqueous ammonium chloride solution was added to destroy the excess of reducing agent. THF (50 ml) was added. the mixture was filtered and the filtrate was evaporated to give N-methyl-4-[1-(4-pyridyl)piperidin-4-yloxy] aniline as a pale yellow solid (0.62 g), m.p. 161–164° C.;

NMR Spectrum (CDCl$_3$) 1.82 (m, 2H), 1.98 (m, 2H), 2.82 (s, 3H), 3.27 (m, 2H), 3.64 (m, 2H), 4.34 (m, 1H), 6.57 (d, 2H), 6.66 (d, 2H), 6.82 (d, 2H), 8.25 (d, 2H);

Mass Spectrum m/z 284 (M+H).

EXAMPLE 11

Using an analogous procedure to that described in Example 4, 4-[1-(4-pyridyl)piperidin-4-ylmethoxy]aniline was reacted with 4'-bromo-4-biphenylylsulphonyl chloride. The crude reaction product was washed with methylene chloride. There was thus obtained 4'-bromo-N-{4-[1-(4-pyridyl)piperidin-4-ylmethoxy]phenyl}-4-biphenylylsulphonamide, hydrochloride salt, as a white solid in 77% yield, m.p. 293–295° C.;

NMR Spectrum 1.30 (q, 2H), 1.87 (d, 2H), 2.21 (m, 1H), 3.18 (m, 2H), 3.78 (d, 2H), 4.22 (d, 2H), 6.81 (d, 2H), 7.01 (d, 2H), 7.18 (d, 2H) 7.67 (s, 4H), 7.77 (d. 2H), 7.84 (d, 2H), 8.18 (d, 2H), 10.0 (s, 1H), 13.3 (broad s, 1H);

Mass Spectrum m/z 578/580 (M+H);

Elemental Analysis Found C, 55.8; H, 4.9; N, 6.6. $C_{29}H_{28}BrN_3O_3S$ 1HCl 1.5$H_2O$ requires C, 55.8; H, 4.9; N, 6.7%.

The 4-[1-(4-pyridyl)piperidin-4-ylmethoxy]aniline used as starting material was obtained as follows:

Using an analogous procedure to that used in the first paragraph of the portion of Example 4 which is concerned with the preparation of starting materials, 1-(4-pyridyl)piperidin-4-ylmethanol (Chemical Abstracts, vol. 113, abstract 231211n; European Patent Application No. 0 359 389) was reacted with 4-(N-tert-butoxycarbonylamino)phenol. The resultant product was treated with a saturated solution of hydrogen chloride in diethyl ether using an analogous procedure to that used in the second paragraph of the portion of Example 4 which is concerned with the preparation of starting materials. There was thus obtained 4-[1-(4-pyridyl)piperidin-4-ylmethoxy]aniline in 22% yield, m.p. 210–211° C.

EXAMPLE 12

Using an analogous procedure to that described in Example 4, 4-[1-(4-pyridyl)piperidin-4-ylmethoxy]aniline was reacted with 6-bromonaphth-2-ylsulphonyl chloride. There was thus obtained 6-bromo-N-{4-[1-(4-pyridyl)piperidin-4-ylmethoxy]-phenyl}-2-naphthalenesulphonamide, hydrochloride salt, as a white solid in 76% yield, m.p. 167–169° C.;

NMR Spectrum 1.26 (m, 2H), 1.84 (d, 2H), 2.10 (m, 1H), 3.15 (m, 2H), 3.72 (d, 2H), 4.20 (d, 2H), 6.75 (d, 2H), 6.96 (d, 2H), 7.16 (d, 2H), 7.76 (m, 2H), 8.05 (d, 2H), 8.16 (d, 2H), 8.31 (d, 2H), 10.05 (s, 1H);

Mass Spectrum m/z 552/554 (M+H);

Elemental Analysis Found C, 53.7; H, 4.9; N, 7.1. $C_{27}H_{26}BrN_3O_3S$ 1HCl 1$H_2O$ requires C, 53.3; H, 5.0; N, 6.9%.

EXAMPLE 13

Using an analogous procedure to that described in Example 4, 4-[1-(4-pyridyl)piperidin-4-ylmethoxy]aniline was reacted with (E)-4-chlorostyrylsulphonyl chloride. There was thus obtained 4-chloro-N-{4-[1-(4-pyridyl)piperidin-4-ylmethoxy]phenyl}-(E)-styrylsulphonamide, hydrochloride salt, in 34% yield, m.p. 220–223° C.;

NMR Spectrum 1.30 (m, 2H), 1.88 (d, 2H), 2.13 (m, 1H), 3.14 (m, 2H), 3.79 (d, 2H), 4.22 (d, 2H), 6.84 (d, 2H), 7.10 (d, 2H), 7.15 (d, 2H), 7.17 (d, 1H), 7.32 (d, 1H), 7.43 (d, 2H), 7.68 (d, 2H), 8.17 (d, 2H), 9.69 (s, 1H);

Mass Spectrum m/z 484/486 (M+H);

Elemental Analysis Found C, 54.7; H, 5.2; N, 7.7. $C_{25}H_{26}ClN_3O_3S$ 1HCl 1.5$H_2O$ requires C, 54.9; H, 5.5; N, 7.7%.

EXAMPLE 14

Using an analogous procedure to that described in Example 6, 4'-bromo-N-{4-[1-(4-pyridyl)piperidin-4-ylmethoxy]phenyl}-4-biphenylylsulphonamide, hydrochloride salt, was reacted with 4'-bromo-4-biphenylylsulphonyl chloride. There was thus obtained 4'-bromo-N-(4'-bromo-4-biphenylylsulphonyl)-N-{4-[1-(4-pyridyl)piperidin-4-ylmethoxy]phenyl}-4-biphenylylsulphonamide in 91% yield, m.p. 136–140° C.;

NMR Spectrum 1.31 (m, 2H), 1.84 (d, 2H), 2.05 (m, 1H), 2.89 (t, 2H), 3.88 (d, 2H), 3.98 (d, 2H), 6.83 (d, 2H), 6.99 (s, 4H), 7.73 (s, 8H), 7.89 (d, 4H), 7.99 (d, 4H), 8.12 (d, 2H);

Mass Spectrum m/z 874 (M+H).

EXAMPLE 15

Using an analogous procedure to that described in Example 6, 6-bromo-N-{4-[1-(4-pyridyl)piperidin-4-ylmethoxy]phenyl}-2-naphthalenesulphonamide, hydrochloride salt, was reacted with 6-bromonaphth-2-ylsulphonyl chloride. There was thus obtained 6-bromo-N-(6-bromonaphth-2-ylsulphonyl)-N-{4-[1-(4-pyridyl)piperidin-4-ylmethoxy]phenyl}-2-naphthalenesulphonamide in 99% yield, m.p. 246–252° C.;

NMR Spectrum 1.47 (m, 2H), 1.93 (d, 2H), 2.07 (m, 1H), 2.91 (t, 2H), 3.82 (d, 2H), 3.94 (d, 2H), 6.67 (d, 2H), 6.81 (d, 2H), 6.94 (d, 2H), 7.71 (d, 2H), 7.82 (d, 2H), 7.90 (d, 2H), 7.99 (d, 2H), 8.13 (s, 2H), 8.26 (d, 2H), 8.43 (s, 2H);

Mass Spectrum m/z 822 (M+H).

EXAMPLE 16

Using an analogous procedure to that described in Example 4 except that the reaction mixture was stirred at ambient temperature for 71 hours, 3-[1-(4-pyridyl)piperidin-4-yloxy]aniline was reacted with 6-bromonaphth-2-ylsulphonyl chloride. The product was washed with methylene chloride and dried. There was thus obtained 6-bromo-N-{3-[1-(4-pyridyl)piperidin-4-yloxy]phenyl}-2-naphthalenesulphonamide, hydrochloride salt, in 77% yield, m.p. 298–300° C.;

NMR Spectrum 1.63 (m, 2H), 1.92 (m, 2H), 3.57 (m, 2H), 3.81 (m, 2H), 4.57 (m, 1H), 6.70 (m, 3H), 7.18 (m, 3H), 7.77 (m, 2H), 8.08 (m, 2H), 8.21 (d, 2H), 8.30 (s, 1H), 8.47 (s, 1H), 10.41 (s, 1H), 13.47 (broad s, 1H);

Mass Spectrum m/z 538/540 (M+H);

Elemental Analysis Found C, 53.8; H, 4.5; N, 7.2. $C_{26}H_{24}N_3O_3S$ 1HCl 0.25$H_2O$ requires: C, 53.9; H, 4.4; N, 7.25%.

The 3-[1-(4-pyridyl)piperidin-4-yloxy]aniline used as a starting material was prepared as follows:

Diethyl azodicarboxylate (3 ml) was added over 15 minutes to a stirred mixture of 1-(4-pyridyl)piperidin-4-ol (3.39 g), 3-(N-tert-butoxycarbonylamino)phenol (Chemical Abstracts, vol. 119, abstract 139113; PCT Patent Application WO 9306085; 3.98 g), triphenylphosphine (4.99 g) and THF (150 ml) which had been cooled to 4° C. The resultant mixture was stirred for 48 hours at ambient temperature. The solvent was evaporated and the residue was purified by column chromatography using a 9:1 mixture of methylene chloride and methanol as eluent. The resultant foam was crystallised from diethyl ether to give tert-butyl N-{3-[1-(4-pyridyl)piperidin-4-yloxy]phenyl}carbamate (4.65 g), m.p. 165–166° C.

A 2.2M solution of hydrogen chloride in methanol (45 ml) was added over 15 minutes to a stirred solution in methanol (25 ml) of a portion (2.53 g) of the carbamate so obtained. The mixture was stirred at ambient temperature for 24 hours. The solvent was evaporated and the residue was dissolved in water (50 ml). A 1M aqueous sodium hydroxide solution (25 ml) was added and the mixture was stirred for 1 hour. The precipitate was collected, washed with water and with diethyl ether and dried. There was thus obtained 3-[1-(4-pyridyl)piperidin4-yloxy]aniline (1.71 g), m.p. 184–186° C.;

NMR Spectrum 1.60 (m, 2H), 1.96 (m, 2H), 3.23 (m, 2H+H2O), 3.65 (m, 2H) 4.48 (m, 1H), 5.00 (s, 2H), 6.16 (m, 3H), 6.82 (d, 2H), 6.88 (t. 1H), 8.15 (d, 2H).

EXAMPLE 17

Diethyl azodicarboxylate (0.157 ml) was added over 15 minutes to a stirred mixture of 1-(4-pyridyl)piperidin-4-ol (0.178 g), 4-(4-chlorophenylsulphonyl)phenol (*J. Amer. Chem. Soc.*, 1956, 78, 3400; 0.269 g), triphenylphosphine (0.265 g) and THF (10 ml) which had been cooled to 4° C. The resultant mixture was stirred for 42 hours at ambient temperature. The solvent was evaporated and the the residue was purified by column chromatography using a 9:1 mixture of methylene chloride and methanol as eluent. The residue was triturated under diethyl ether to give 4-[4-chlorophenylsulphonyl)phenoxy]-1-(4-(pyridyl)piperidine (0.134 g), m.p. 151–152° C.;

NMR Spectrum 1.68 (m, 2H), 2.02 (m, 2H), 3.24 (m, 2H+H2O), 3.67 (m, 2H), 4.78 (m, 1H), 6.81 (d, 2H), 7.17 (d, 2H), 7.65 (d, 2H), 7.89 (m, 4H), 8.13 (d, 2H);

Mass Spectrum m/z 429/431 (M+H);

Elemental Analysis Found C, 60.6; H, 4.8; N, 6.6. C22H21ClN2O3S 0.5H2O requires C, 60.3; H, 5.1; N, 6.4%.

EXAMPLE 18

N-(4-Pyridyl)piperazine (0.163 g) was added, in one portion, to a stirred solution of 5-(6-bromonaphth-2-ylsulphonyl)phthalic anhydride (0.417 g.) in DMF (10 ml.) and the mixture was stirred at ambient temperature for 1 hour. Diethyl ether (40 ml.) was added and the mixture was stirred rapidly. The resultant white, amorphous precipitate was recovered by filtration. There was thus obtained a 1:1 mixture (0.474 g., 81%) of: 5-(6-bromonaphth-2-ylsulphonyl)-2-[4-(4-pyridyl)piperazin-1-ylcarbonyl] benzoic acid and 4-(6-bromonaphth-2-ylsulphonyl)-2-[4-(4-pyridyl)piperazin-1-ylcarbonyl]benzoic acid; the mixture giving the following characterising data;

NMR Spectrum 3.2–3.8 (m, 16H), 6.8 (m, 4H), 7.5 (d, 1H), 7.8–7.9 (m, 3H), 8.0 (m, 2H), 8.05 (s, 2H), 8.1–8.25 (m, 10H), 8.4 (d, 2H), 8.45 (d, 1H), 8.8 (s, 1H);

Mass Spectrum m/z 579 (M+H);

Elemental Analysis Found C, 52.9; H, 4.5; N, 6.8. C27H22BrN3O5S 2H2O requires C, 52.6; H, 4.3; N, 6.8%.

The 5-(6-bromonaphth-2-ylsulphonyl)phthalic anhydride used as a starting material was prepared as follows:

Triethylamine (3.1 ml) was added dropwise to a stirred mixture of 5-bromophthalic anhydride (5-bromo-1,3-dihydro-2-benzofuran-1,3-dione; 4.54 g), 6-bromo-2-naphthalenethiol (European Patent Application No. 0409413, Example 19; 5.25 g) and DMF (50 ml) and the mixture was stirred at ambient temperature for 10 minutes. The mixture was heated at 60° C. for 1 hour and then stirred at ambient temperature for 16 hours. The solvent was evaporated and the residue was suspended in methanol (60 ml). The mixture was basified by the addition of 2M aqueous sodium hydroxide solution and the mixture was heated to reflux for 1 hour. The mixture was cooled ambient temperature and partitioned between water (300 ml) and diethyl ether. The aqueous layer was acidified by the addition of concentrated hydrochloric acid and extracted with ethyl acetate (2×100 ml). The combined extracts were washed with water and with brine, dried (MgSO4) and evaporated. The residue was triturated under diethyl ether to give 4-(6-bromonaphth-2-ylthio)phthalic acid (6 g, 74%) as a pale yellow solid;

NMR Spectrum (CDCl3/DMSO) 7.02 (m, 1H), 7.18 (m, 1H), 7.2–7.55 (m, 5H), 7.65 (s, 1H), 7.72 (s, 1H).

A portion (4.5 g) of the material so obtained was suspended in glacial acetic acid (50 ml.) and sodium perborate tetrahydrate (5.13 g) was added in small portions. The reaction mixture was then stirred at ambient temperature for 16 hours. A further portion (1.72 g) of sodium perborate tetrahydrate was added and the mixture was stirred for a further 6 hours. The reaction mixture was poured into water (500 ml.) and extracted with ethyl acetate. The extracts were washed with water and with brine, dried (MgSO4) and evaporated to give 4-(6-bromonaphth-2-ylsulphonyl) phthalic acid as a white solid (5.31 g);

NMR Spectrum 7.85 (m, 2H), 8.0 (m, 1H), 8.1–8.3 (m, 4H), 8.35 (d, 1H), 8.8 (s, 1H).

A mixture of a portion (0.538 g) of the material so obtained was suspended in acetic anhydride (5 ml) and the mixture was heated to 100° C. until a clear solution was obtained. The mixture was cooled to ambient temperature. The resultant white solid was recovered by filtration, washed with diethyl ether and dried to give 5-(6-bromonaphth-2-ylsulphonyl)phthalic anhydride (0.362 g);

Mass Spectrum m/z 416 (M+H).

Elemental Analysis Found C, 52.0; H, 2.1. C18H9BrO5S requires C, 51.8; H, 2.17%.

EXAMPLE 19

To a solution of 4-((4-(4-pyridyl)piperazin-1-ylmethyl) benzoic acid chloride (510 mg) in dichloromethane (20 ml) was added triethylamine (1 ml), followed by a solution of 4-(4-chlorophenoxy)aniline (265 mg). The resulting mixture was stirred at room temperature for 18 hours. The mixture was partitioned between water and dichloromethane. The organic extracts were dried (MgSO$_4$) and evaporated to give a gum which was purified by column chromatography on silica eluting with increasing concentrations of methanol and dichloromethane to give 1-[4-(4-(4-chlorophenoxy) phenylaminocarbonyl)benzyl]-4-(4-pyridyl)piperazine as a glass (32 mg);

NMR Spectrum 8.15 (d, 2H), 7.95 (d, 2H), 7.8 (d, 2H)7.4–7.5 (m, 4H), 6.95–7.1 (m, 4H), 6.85 (d, 2H), 3.6 (s, 2H), 3.2–3.4 (m, 8H);

Mass Spectrum m/z 499 (M+H)$^+$;

Elemental Analysis Found C, 66.3; H, 5.4; N, 10.7. C$_{29}$H$_{27}$ClN$_4$O$_2$.1.5H$_2$O requires C, 66.2; H, 5.7; N, 10.65%.

The acid chloride used as a starting material was prepared as follows:

(a) To a suspension of 4-(4-pyridyl)piperazine (13.1 g) in ethyl acetate (200 ml) was added triethylamine (56 ml) followed dropwise, over 5 hours, by a solution of methyl 4-bromomethylbenzoate (18.41 g). The mixture was stirred at room temperature for 18 hours. The mixture was partitioned between water and ethyl acetate. The organic extracts were dried (MgSO$_4$) and evaporated to give a gum, which was purified by column chromatograhy on silica eluting with increasing concentrations of methanol/dichloromethane to give methyl 4-(4-(4-pyridyl)piperazin-1-ylmethyl)benzoate (13.1 g) as a solid;

NMR Spectrum 8.15 (d, 2H), 7.95 (d, 2H), 7.5 (d, 2H), 6.8 (d, 2H), 3.85 (s, 3H), 3.6 (s, 2H), 3.25–3.35 (m, 4H), 2.45–2.55 (m, 4H);

Mass Spectrum m/z 311 (M+H)$^+$;

Elemental Analysis Found C, 69.2; H, 6.6; N, 13.5. C$_{18}$H$_{21}$N$_3$O$_2$ requires C, 69.4; H, 6.8; N, 13.5%.

(b) To a solution of the product of step (a) (849 mg) in methanol (15 ml) was added 2N sodium hydroxide (6.8 ml) and the resulting mixture was stirred for 3 hours. The mixture was evaporated to dryness. The resulting gum was dissolved in water (7 ml) and acidified with acetic acid. The mixture was filtered to give 4-(4-(4-pyridyl)piperazin-1-ylmethyl)benzoic acid (429 mg);

NMR Spectrum (CD$_3$SOCD$_3$+CD$_3$COOD) 8.15 (d, 2H), 8.0 (d, 2H), 7.5 (d, 2H), 7.1 (d, 2H), 3.7–3.8 (m, 6H), 2.7–2.8 (m, 4H);

Mass Spectrum m/z 298 (M+H)$^+$;

Elemental Analysis Found C, 68.3; H, 6.4; N, 14.0. C$_{17}$H$_{19}$N$_3$O$_2$ requires: C, 68.7; H, 6.4; N, 14.1%.

(c) To a suspension of the product from step (b) (5.19 g) in dichloromethane (100 ml) was added thionyl chloride (7.3 ml). The resulting mixture was stirred for 3 hours and then evaporated to give the acid chloride as a solid (7.66 g) which was used without further purification.

EXAMPLE 20

To a solution of 2-[1-(4-pyridyl)piperidin-4-ylmethoxy] aniline (131 mg) in pyridine (5 ml) was added 6-bromonaphthyl-2-sulphonyl chloride (148 mg). The resulting mixture was heated to 120° C. for 18 hours. The mixture was concentrated to a gum, which was purified by column chromatography on silica eluting with increasing concentrations of methanol and dichloromethane to give 6-bromo-N-{2-[1-(4-pyridyl)piperidin-4-ylmethoxy] phenyl}-2-naphthalenesulphonamide (177 mg), m.p. 197–200° C.;

NMR Spectrum 8.15 (s, 2H), 8.0–8.1 (m, 4H), 7.8 (dd, 1H), 7.55 (dd, 1H), 7.3 (dd, 1H), 7.05–7.1 (m, 1H), 6.8–6.9 (m, 2H), 6.7 (d, 2H), 3.7 (d, 2H), 3.3–3.4 (m, 2H), 2.4–2.4 (m, 2H), 1.3–1.4 (m, 3H), 0.7–0.9 (m, 2H);

Mass Spectrum m/z=552/554 (M+H$^+$);

Elemental Analysis Found C, 56.5; H, 4.6; N, 7.5. C$_{27}$H$_{26}$BrN$_3$O$_3$S.H$_2$O requires C, 56.8; H, 4.9; N, 7.4%.

The 2-[1-(4-pyridyl)piperidin-4-ylmethoxy]aniline used as a starting material was prepared as follows:

(a) To a solution of 2-aminophenol (2.84 g) in dichloromethane (120 ml) was added di-tert-butyl dicarbonate (6.55 g). The mixture was stirred at room temperature for 18 hours. The mixture was partitioned between water and dichloromethane. The organic extracts were dried (MgSO$_4$) and evaporated to give a solid which was purified by column chromatography on silica eluting with a mixture of ethyl acetate and hexane (20:80) to give 2-tert-butyloxycarbonylaminophenol (1.80 g);

NMR Spectrum 9.7 (s, 1H), 7.7 (s, 1H), 7.6 (d, 1H), 6.7–6.9 (m, 3H), 1.45 (s, 9H);

Mass Spectrum m/z=210 (M+H)$^+$.

(b) To a solution of 1-(4-pyridyl)piperidin-4-ylmethanol (357 mg) and 2-tert-butyloxycarbonylaminophenol (328 mg) in tetrahydrofuran (15 ml) was added triphenylphosphine (447 mg) followed by diethyl azodicarboxylate (0.27 ml). The mixture was stirred at room temperature for 18 hours. The reaction mixture was concentrated to a gum which was purified by column chromatography on silica eluting with methanol/dichloromethane (10:90) to give the tert-butyloxycarbonyl protected derivative of 2-[1-(4-pyridyl)piperidin-4-ylmethoxy]aniline (1.05 g);

NMR Spectrum 8.2 (d, 2H), 7.5–7.7 (m, 2H), 6.95–7.05 (m, 2H), 6.8 (d, 2H), 3.85–4.1 (m, 4H), 2.8–2.95 (m, 2H), 1.8–1.9 (m, 1H), 1.45 (s, 9H), 1.15–1.25 (m, 5H);

Mass Spectrum m/z=384 (M+H)$^+$.

(c) To a solution of the product from step (b) (1.39 g) in methanol (50 ml) was added methanolic HCl (5 ml) and the resulting mixture was stirred for 4 days. The reaction mixture was partitioned between sodium bicarbonate solution and dichloromethane. The organic extracts were dried (MgSO$_4$) and evaporated to give 2-[1-(4-pyridyl)piperidin-4-ylmethoxy]aniline as a solid (971 mg) which was used without further purification;

NMR Spectrum 8.1–8.15 (m, 2H), 6.6–6.8 (m, 6H), 3.7–4.0 (m, 6H), 2.85–3.0 (m, 2H), 1.8–2.2 (m, 5H), 1.2–1.3 (m, 2H).

EXAMPLE 21

Using an analogous procedure to that described in Example 4 except that the reaction mixture was stirred at ambient temperature for 26 hours, 3-[1-(4-pyridyl)piperidin-4-yloxy]aniline was reacted with (E)-4-chlorostyrylsulphonyl chloride. The product was washed with methylene chloride and dried. There was thus obtained 4-chloro-N -{3-[1-(4-pyridyl)piperidin-4-yloxy]phenyl}-(E)-styrylsulphonamide, hydrochloride salt, in 73% yield, m.p. 147–150° C.;

NMR Spectrum 1.59 (m, 2H), 2.00 (m, 2H), 3.58 (m, 2H), 3.86 (m, 2H), 4.63 (m, 1H), 6.70 (d, 1H), 6.77 (m, 2H), 7.20 (m, 3H), 7.30 (d, 1H), 7.49 (m, 3H), 7.73 (d, 2H), 8.22 (d, 2H), 10.10 (bs, 1H);

Mass Spectrum m/z 470/472 (M+H);

Elemental Analysis Found C, 56.2; H, 5.1; N, 8.4. C$_{24}$H$_{24}$ClN$_3$O$_3$S 1HCl 0.25H$_2$O requires: C, 56.4; H, 5.0; N, 8.2%.

The 3-[1-(4-pyridyl)piperidin-4-yloxy]aniline used as starting material was prepared in Example 16.

EXAMPLE 22

Using an analogous procedure to that described in Example 17, 1-(4-pyridyl)piperidin-4-ol was reacted with 4-(6-bromonaphth-2-ylsulphonyl)phenol. There was thus obtained 4-[4-(6-bromonaphth-2-ylsulphonyl)phenoxy]-1-(4-pyridyl)piperidine in 62% yield, m.p. 180–183° C.;

NMR Spectrum 1.62 (m, 2H), 1.97 (m, 2H), 3.24 (m, 2H+H$_2$O), 3.65, (m, 2H), 4.77 (m, 1H), 6.80 (d, 2H), 7.19 (d, 2H), 7.80 (d, 1H), 7.91 (d, 3H), 8.05–8.19 (m, 4H), 8.34 (s, 1H), 8.70 (s, 1H);

Mass Spectrum m/z 523/525 (M+H);

Elemental Analysis Found C, 59.3; H, 4.4; N, 5.7. C$_{26}$H$_{23}$BrN$_2$O$_3$S requires: C, 59.7; H, 4.4; N, 5.4%.

The 4-(6-bromonaphth-2-ylsulphonyl)phenol used as a starting material was prepared as follows:

Aluminium chloride (3.33 g) was added portionwise over 30 minutes to a stirred mixture of 6-bromonaphth-2-ylsulphonyl chloride (6.11 g) and anisole (3.33 g) in dry methylene chloride (35 ml). The resultant mixture was stirred for 24 hours. Methylene chloride (75 ml) was added. the mixture cooled to 4° C. and water (100 ml) added cautiously. The mixture was acidified with 2M hydrochloric acid, separated and the aqueous phase extracted with methylene chloride (30 ml). The combined organic phases were washed with water, dried ($MgSO_4$) and evaporated. Recrystallisation of the residue from an ethyl acetate/ethanol mixture gave 4-(6-bromonaphth-2-ylsulphonyl)anisole (1.74 g), m.p. 180–181° C.;

NMR spectrum 3.80 (s, 3H), 7.12 (d, 2H), 7.80 (d, 1H), 7.92 (m, 3H), 8.08 (d, 1H), 8.16 (d, 1H), 8.32 (s, 1H), 8.69 (s, 1H);

Mass spectrum m/z 377/379 (M+H).

A 1M solution of boron tribromide in methylene chloride (9.65 ml) was slowly added to a stirred, cooled (−78° C.), methylene chloride (25 ml) solution of a portion (1.21 g) of the anisole derivative so obtained. The mixture was stirred for 20 hours at ambient temperature, then cooled to −10° C., diethyl ether (4 ml) slowly added, and stirring continued for 10 minutes. Water (25 ml) was added and the mixture extracted with ethyl acetate (2×25 ml). The combined organic extracts were washed with water, dried ($MgSO_4$) and evaporated. Trituration of the residue under ether gave 4-(6-bromonaphth-2-ylsulphonyl)phenol (1.03 g), m.p. 178–180° C.;

NMR Spectrum 6.92 (d, 2H), 7.77–7.91 (m, 4H), 8.06 (d, 1H), 8.14 (d, 1H), 8.32 (s, 1H), 8.68 (s, 1H), 10.62 (s, 1H);

Mass Spectrum m/z 361/363 (M−H);

Elemental Analysis Found C, 52.3; H, 3.2; S, 8.3. $C_{16}H_{11}BrO_3S$ 0.25$H_2O$ requires: C, 52.3; H, 3.15; S, 8.7%.

EXAMPLE 23

6-Bromo-2-naphthylenethiol (2.39 g) was slowly added to a stirred suspension of sodium hydride (60% w/w suspension in mineral oil, 404 mg) in DMF (10 ml) at 4° C. After 1 hour, a portion (569 mg) 4-(4-fluorobenzoyl)-1-(4-pyridyl)piperidine and further dimethylformamide (8 ml) were added The mixture was stirred at 50° for 24 hours and then 16 hours at ambient temperature. The mixture was added to water (50 ml) and extracted with methylene chloride (3×50 ml). The combined organic extracts were washed with water, dried (Mg $SO_4$) and evaporated. The residue was purified by column chromatography using increasingly polar mixtures of methanol and methylene chloride as eluent. There was thus obtained 4-[4-(6-bromonaphth-2-ylthio)benzoyl]-1-(4-pyridyl)piperidine (613 mg);

NMR Spectrum ($CDCl_3$) 1.70–2.02 (m, 4H+$H_2O$), 3.03 (td, 2H), 3.43 (m, 1H), 3.92, (dm, 2H), 6.68 (d, 2H), 7.25 (s, 2H), 7.51 (d, 1H), 7.60 (d, 1H), 7.67 (d, 1H), 7.77 (d, 1H), 7.84 (d, 2H), 8.01 (d, 2H), 8.25 (bs, 2H);

Mass Spectrum m/z 503/505 (M+H).

The 4-(4-fluorobenzoyl)-1-(4-pyridyl)piperidine used as a starting material was prepared as follows:

A stirred mixture of 4-(4-fluorobenzoyl)piperidine, hydrochloride salt (3.90 g), 4-chloropyridine, hydrochloride salt (2.85 g) and triethylamine (4.90 ml) in xylene (75 ml) was heated at 145° C. for 27 hours. The solvent was evaporated and the residue partitioned between methylene chloride (150 ml) and water (100 ml), the pH being adjusted to ~10 with 0.880 ammonia. The aqueous phase was extracted with a further methylene chloride (50 ml). The combined organic phases were washed with water, dried (Mg $SO_4$) and evaporated. The residue was purified by column chromatography using a 19:1 mixture of methylene chloride and methanol as eluent to give 4-(4-fluorobenzoyl)-1-(4-pyridyl)piperidine (1.89 g);

NMR Spectrum ($CDCl_3$) 1.80–2.06 (m, 4H+$H_2O$), 3.03 (t, 2H), 3.48 (m, 1H), 3.94, (d, 2H), 6.68 (d, 2H), 7.18 (t, 2H), 8.01 (m, 2H), 8.28 (d, 2H);

Mass Spectrum m/z 285 (M+H).

EXAMPLE 24

Sodium perborate tetrahydrate (614 mg) was added to a stirred solution of 4-[4-(6-bromonaphth-2-ylthio)benzoyl]-1-(4-pyridyl)piperidine (505 mg) in glacial acetic acid (25 ml). After 4 hours further sodium perborate tetrahydrate (614 mg) was added and stirring continued for 27 hours. The reaction mixture was poured into an ice/water mixture (50 ml) and extracted with methylene chloride (4×25 ml). The combined extracts were washed with water and with brine, dried (Mg $SO_4$) and evaporated. The residue was purified by column chromatography using a 19:1 methylene chloride and methanol mixture as eluent and the resultant foam triturated under iso-hexane. There was thus obtained 4-[4-(6-bromonaphth-2-ylsulphonyl)benzoyl]-1-(4-pyridyl)piperidine (21 mg);

NMR Spectrum ($CDCl_3$) 1.77–2.05 (m, 4H), 3.15 (td, 2H), 3.52 (m, 1H), 4.00, (m, 2H), 6.71 (d, 2H), 7.72 (dd, 1H), 7.85 (m, 3H), 8.08 (m, 5H), 8.24 (d, 2H), 8.57 (s, 1H);

Mass Spectrum m/z 535/537 (M+H).

EXAMPLE 25

A stirred mixture of 4-chloropyridine hydrochloride (78.3 mg), 1-[4-(6-bromonaphth-2-ylsulphonyl)phenylsulphonyl]piperazine hydrochloride (185 mg), triethylamine (0.145 ml) and xylene (3.0 ml) was heated at 140° C. for 16 hours. The solvent was evaporated and the residue purified by column chromatography on a C-18 60A preparative reversed-phase HPLC column using 0.1% trifluoroacetic acid in aqueous acetonitrile and a gradient of 30% to 70% acetonitrile. There was thus obtained 4-[4-(6-bromonaphth-2-ylsulphonyl)phenylsulphonyl]-1-(4-pyridyl)piperazine, trifluoroacetate salt (29.1 mg), m.p. 236–238° C.:

NMR Spectrum 3.10 (t, 4H), 3.74 (t, 4H), 7.10 (d, 2H), 7.82 (d, 1H), 7.98 (d, 3H), 8.08–8.29 (m, 6H), 8.36 (s, 1H), 8.78 (s, 1H).

Mass Spectrum m/z 572/574 (M+H).

The 1-[4-(6-bromonaphth-2-ylsulphonyl)phenylsulphonyl]piperazine used as a starting material was prepared as follows:

4-Fluorobenzenesulphonyl chloride (1.95 g) was added to a stirred solution of N-tert-butyloxycarbonylpiperazine (1.86 g) and triethylamine (6.9 ml) in methylene chloride (100 ml) at 4° C. and stirring continued at ambient temperature for 16 hours. The solvent was evaporated and the residue purified by column chromatography using methylene chloride and 1% methanol in methylene chloride as eluent. There was thus obtained 4-(4-fluorophenylsulphonyl)-1-(tert-butyloxycarbonyl)piperazine (3.09 g), m.p. 163–164° C.;

NMR Spectrum ($CDCl_3$) 1.42 (s, 9H), 2.98 (t, 4H), 3.51 (t, 4H), 7.23 (m, 2H), 7.77 (m, 2H);

Mass Spectrum m/z 362 (M+$NH_4$);

Elemental Analysis Found C, 52.1; H, 6.1; N, 8.0. $C_{15}H_{21}FN_2O_4S$ requires: C, 52.3; H, 6.15; N, 8.1%.

Sodium hydride (60% w/w suspension in mineral oil, 88 mg) was slowly added to a stirred solution of 6-bromo-2-naphthylenethiol (478 mg) in dry DMF (5 ml) at 4° C. and stirring continued for 30 minutes. A portion of the piperazine derivative (688 mg) prepared in the previous paragraph was added and stirring continued for 1 hour at 4° C. and for 64 hours at ambient temperature. The mixture was added to an ice/water mixture and the precipitated solid collected by filtration. Purification by column chromatography using initially a 10% then a 15% mixture of ethyl acetate and iso-hexane as eluent gave 4-[4-(6-bromonaphth-2-ylthio)phenylsulphonyl]-1-(tert-butyloxycarbonyl)piperazine (630 mg), m.p. 99–101° C.;

NMR Spectrum (CDCl$_3$) 1.42 (s, 9H), 2.97 (t, 4H), 3.49 (t, 4H), 7.25 (m, 2H), 7.5–7.8 (m, 6H) 8.06 (d, 2H);

Mass Spectrum m/z 507/509 (M+H−C$_4$H$_8$);

Elemental Analysis Found C, 53.6; H, 5.1; N, 5.0. C$_{25}$H$_{27}$BrN$_2$O$_4$S$_2$ requires: C, 53.3; H, 4.8; N, 5.0%.

Sodium perborate tetrahydrate (308 mg) was added to a stirred solution of a portion (282 mg) of the material prepared above in glacial acetic acid (2 ml). After stirring for 16 hours, further acetic acid (2 ml) and sodium perborate tetrahydrate (308 mg) were added, stirring continued for 16 hours when a final addition of acetic acid (10 ml) and sodium perborate tetrahydrate (308 mg) was made. After stirring for a further 16 hours the reaction mixture was poured into an ice/water mixture. The precipitated solid was isolated giving 4-[4-(6-bromonaphth-2-ylsulphonyl)phenylsulphonyl]-1-(tert-butyloxycarbonyl)piperazine (295 mg), m.p. 213–215° C., which was used without further purification.

A solution of the material so obtained (295 mg) in methylene chloride (10 ml) was treated with a 2.2M solution of hydrogen chloride in diethyl ether (1.2 ml). The mixture was stirred at ambient temperature for 48 hours. The precipitated solid was collected by filtration and washed with methylene chloride giving 1-[4-(6-bromonaphth-2-ylsulphonyl)phenylsulphonyl)piperazine hydrochloride salt, (205 mg), m.p. 250–260° C. (decomposition);

NMR Spectrum 3.12 (s, 8H), 7.83 (d, 1H), 8.01 (m, 3H), 8.15 (d, 1H), 8.20 (d, 1H), 8.28 (d, 2H), 8.36 (s, 1H), 8.81 (s, 1H), 8.98 (bs, 2H);

Mass Spectrum m/z 495/497 (M+H).

EXAMPLE 26

To a solution of 6-(bromo-2-(4-(2-aminoethylaminocarbonyl)phenyl sulphonyl)naphthalene (400 mg) in ethanol (15 ml) was added 4-chloropyrimidine hydrochloride (131 mg) and triethylamine (294 mg). The mixture was heated to reflux for 3 hours. Further portions of 4-chloropyrimidine (131 mg) and triethylamine (108 mg) were added and heating continued for a further 1 hour.

After cooling, the reaction mixture was diluted with ethyl acetate (100 ml.), washed with water (2×25 ml) and brine (25 ml), dried (MgSO4) and evaporated to give a solid. This was purified by chromatography on a Mega Bond Elut silica column, eluting with dichloromethane containing increasing proportions of methanol (0%–5%) to give 6-(bromo-2-(4-(2-pyrimidin-4-yl)aminoethylaminocarbonyl)phenylsulphonyl)naphthalene (140 mg);

NMR spectrum 3.3–3.5 (m, 4H); 6.45(m, 1H); 7.3–7.5(m, 1H); 7.8(dd, 1H); 7.9–8.05 (m, 4H); 8.05–8.2 (m, 3H); 8.25 (d, 1H); 8.4 (d, 2H); 8.8 (s, 2H);

Mass spectrum m/z 511 (m+H);

Elemental Analysis Found C, 50.2; H, 3.7; N, 10.0. C23H19BrN4O3S.0.6 CH2Cl2 requires C, 50.4; H, 3.6; N, 9.9.

The 6-(bromo-2-(4-(2-aminoethylaminocarbonyl)phenylsulphonyl)naphthalene used as starting material may be prepared as follows.

i) To a suspension of sodium hydride 48% dispersion (960 mg, 20 mmol) in dimethylformamide (50 ml), cooled to 5° C. and stirred under nitrogen, was added in small portions 6-bromonaphthalene-2-thiol (4.78 g, 20 mmol). The mixture was allowed to warm to ambient temperature over 1 hour. 4-Fluorobenzonitrile (2.66 g, 22 mmol) was then added, the mixture heated to 90° C. for a further 1 hour and then poured into water (600 ml). The resulting solid was purified by recrystallisation from methanol to give 6-(bromo-2-(4-cyanophenylthio)naphthalene (5.7 g);

NMR Spectrum 7.3(dd, 2H); 7.55(dd, 1H); 7.7–7.8(m, 3H); 7.9(d, 1H); 8.0(d, 1H); 8.2(s, 1H); 8.3(s, 1H).

(ii) A mixture of the product from i) above (5.7 g), potassium hydroxide (3 g), water (15 ml) and ethylene glycol (100 ml.) was heated to 160° C. for 7 hours. After cooling to ambient temperature the mixture was diluted with water (500 ml.), acidified with concentrated HCl (pH2) and extracted with ethyl acetate (2×200 ml). The combined extracts were washed with water (2×100 ml) and brine (100 ml), dried (MgSO4) and evaporated to give 4-(6-bromonaphth-2-ylthio)benzoic acid (5.3 g);

NMR Spectrum 7.2(dd,2H); 7.5(dd,1H); 7.7(dd,2H); 7.9 (dd,2H); 7.95(d,1H); 8.0(d,1H); 8.1(s,1H); 8.2(s,1H);

Mass Spectrum m/z 357 m−H.

(iii) The acid from ii) above (5.3 g) was suspended in glacial acetic acid (100 ml). Sodium perborate (9 g) was added and the mixture stirred at ambient temperature for 24 hours. A further portion of sodium perborate (9 g) was added and the mixture heated to 55° C. for 6 hours. After cooling to ambient temperature, water (200 ml) was added and the resulting white solid precipitate recovered by filtration to give 4-(6-bromonaphth-2-ylsulphonyl)benzoic acid (4.1 g);

NMR Spectrum 7.8–7.9 (m,2H); 7.95(d,1H); 8.05–8.15; (m,4H); 8.2(d,1H); 8.3 (s,1H); 8.8(s,1H);

iv) The acid from iii) above (7.16) was dissolved in dimethylformamide (100 ml.). N-hydroxysuccinamide (2.88 gm) was added and the mixture cooled to 5° C. EDAC (4.2 g) was added in one portion and the mixture stirred 16 hours at ambient temperature. Ethyl acetate (500 ml) was added and after washing with water (3×100 ml.) and brine (100 ml.) the reaction mixture was evaporated to give a white solid. This was further purified by flash column chromatography on silica gel, eluting with dichloromethane, to give the succinimide ester of the acid product of iii) (6.3 g), mp 287–290° C.;

NMR Spectrum (CDCl$_3$) 2.9(s, 4H); 7.7 (dd,1H); 7.8–7.9 (m, 3H); 8.1 (s, 1H); 8.15 (d,2H); 8.25 (d,2H); 8.6 (s,1H);

Mass Spectrum m/z 389 m−H.

v) The ester from iv) above (976 mg) was treated with N-BOC ethylenediamine (320 mg) in dimethylformamide (10 ml) and stirred at ambient temperature for 18 hours. After diluting with ethyl acetate (150 ml), washing with 2M sodium hydroxide (2×25 ml), 1M citric acid (25 ml), water (25 ml) and brine (25 ml), the reaction mixture was dried (MgSO4) and evaporated to give the tert-butoxycarbonyl derivative of the desired starting material as a white solid. This was dissolved in trifluroacetic acid (5 ml), stirred at ambient temperature for 2 hours and then evaporated to give an oil. Ether (50 ml) was added and the mixture stirred vigorously to give 6-(bromo-2-(4-(2-aminoethylaminocarbonyl)phenylsulphonyl)naphthalene as a white solid which was recovered by filtration (893 mg);

NMR spectrum 2.95(t, 2H); 3.4–3.5 (m,2H); 7.7–7.9 (m,4H); 7.95 (dd,1H); 8.1 (d,2H); 8.15–8.25 (m, 4H); 8.35 (s,1H); 8.75–8.85 (m,2H);

Mass spectrum m/z 433 m+H;

Elemental Analysis Found C, 45.6; H, 3.1; N, 5.2. C19H17BrN2O3S.1.1 TFA requires C, 45.6; H, 3.27; N, 5.01.

EXAMPLE 27

A mixture of the acid from part (ii) of Example 26 (358 mg), hydroxybenztriazole (202 mg), N-(4-pyridyl)piperazine (163 mg) and EDAC (210 mg) was dissolved in dimethylformamide (10 ml) and stirred at ambient temperature for 1 hour. Water (50 ml) and 2M sodium hydroxide (10 ml) was added and the mixture extracted with ethyl acetate (2×50 ml.). After washing the combined extracts with water (2×20 ml), drying (MgSO4) and evaporating 1-[4-(6-bromonaphth-2-ylthio)benzoyl]-4-(4-pyridyl)piperazine was obtained as a white solid. (345 mg), mp 210–213° C.;

NMR Spectrum CDCl3 3.2–3.4 (m,4H); 3.6–4.0(m,4H); 6.7(dd,2H); 7.3–7.4(m,4H);7.45(d,1H), 7.5–7.7(m,2H); 7.75(d,1H); 7.9(s,1H); 8.0(s,1H); 8.3(d,2H);

Mass Spectrum m/z 504 m+H;

Elemental Analysis Found C, 61.8; H, 4.6; N, 8.3. C26H22BrN3OS Requires C, 61.9; H, 4.4; N, 8.3.

EXAMPLE 28

A mixture of the acid from part (iii) of Example 26 (782 mg), hydroxybenztriazole (297 mg), N-(4-pyridyl)piperazine (326 mg) and EDAC (382 mg) was dissolved in dimethylformamide (15 ml) and stirred at ambient temperature for 4 hours. Ethyl acetate (100 ml) was added and after washing with water (2×25 ml) and brine (25 ml) the reaction mixture was evaporated to give a solid. Purification by column chromatography on silica gel (Mega Bond Elut ), eluting with dichloromethane containing an increasing proportion of methanol (0–5%), gave as a solid 1-[4-(6-bromonaphth-2-ylsulphonyl)benzoyl]4-(4-pyridyl)piperazine (120 mg);

NMR Spectrum CDCl3/TFA 3.5–4.0(b,8H); 6.9(d,2H); 7.6(d,2H); 7.7(dd,1H); 7.8–7.9 (m,3H); 8.0–8.1(m,3H); 8.15–8.25(m,2H); 8.55(s,1H);

Mass Spectrum m/z 536 m+H.

Elemental Analysis Found C, 57.2; H, 4.5; N, 7.4. C26H22BrN3O3S.0.5H2O Requires C, 57.3; H, 4.3; N, 7.7.

EXAMPLE 29

A mixture of the acid from part (iii) of Example 26 (391 mg), hydroxybenztriazole (202 mg), N-(4-pyrimidyl)piperazine (326 mg) and EDAC (202 mg) was dissolved in dimethylformamide (10 ml) and stirred at ambient temperature for 3 hours. Ethyl acetate (50 ml) was added and after washing with 2M sodium hydroxide (15 ml), water (2×15 ml) and brine (15 ml) the reaction mixture was evaporated and the residue triturated with methanol to give a solid 1-[4-(6-bromonaphth-2-ylsulphonyl)benzoyl]-4-(4-pyrimidinyl)piperazine (391 mg);

NMR Spectrum 3.2–3.9(m,8H); 6.8(d,1H); 7.7(d,2H); 7.85(dd,1H); 8.0(dd,1H); 8.1–8.25(m,5H); 8.4(s,1H); 8.5(s, 1H); 8.8(s,1H);

Mass Spectrum m/z 537 m+H;

Elemental Analysis Found C, 55.5; H, 4.0; N, 10.4. C25H21BrN4O3S Requires C, 55.9; H, 3.9; N, 10.4.

EXAMPLE 30

A mixture of N-(4-pyridazinyl)piperazine trifluroacetate (278 mg), triethylamine (303 mg), N-hydroxysuccinimide ester from part (iv) of Example 26 (1 mmol) and dimethylformamide (10 ml) was stirred at ambient temperature for 18 hours. The reaction mixture was evaporated and the residue dissolved in ethyl acetate, washed with 2M sodium hydroxide (2×25 ml), water (2×25 ml) and brine (25 ml). After drying (MgSO4), evaporation and trituration with methanol and ether, 1-[4-(6-bromonaphth-2-ylsulphonyl)benzoyl]-4-(4-pyridazinyl)piperazine was obtained as a white solid 420 mg);

NMR Spectrum 3.3–3.8(m,8H); 6.9(dd, 1H); 7.7(d,2H); 7.85(dd, 1H); 8.0(dd, 1H); 8.1(d,2H); 8.15(d,1H); 8.2(d, 1H); 8.4(s,1H); 8.6(d,1H); 8.8(s,1H); 8.9(d,1H);

Mass Spectrum m/z 537 m+H;

Elemental Analysis Found C, 55.1; H, 3.8; N, 10.0. C25H21BrN4O3S.0.5 H2O Requires C, 55.0; H, 4.06; N, 10.3.

EXAMPLE 31

To 4-(6-bromonaphth-2-ylsulphonyl)-2-trifluoromethylbenzoic acid (1.02 g) was added thionyl chloride (10 ml) and dimethylformamide (1 drop). The mixture was heated on a steam bath for 30 minutes and then evaporated to give a yellow solid which was redissolved in dichloromethane (10 ml) and added to an ice cooled solution of N-(4-pyridyl)piperazine (363 mg) and triethylamine (1.16 g) in dichloromethane (10 ml). The mixture was allowed to warm to ambient temperature and stirred for 3 hours. Water (100 ml) was added and the mixture extracted with ethyl acetate (3×50 ml). The combined extracts were washed with water (3×25 ml) and brine (25 ml), dried (MgSO4) and evaporated to give a solid which was further purified by flash column chromatography on silica gel, eluting with dichloromethane containing increasing proportions of methanol (0–5%) to give a solid. Recrystallisation from methanol gave 1-[4-(6-bromonaphth-2-ylsulphonyl-2-trifluoromethylbenzoyl]-4-(4-pyridyl)piperazine (649 mg), mp 221–223° C.;

NMR Spectrum 3.0–3.5(m,6H); 3.6–3.8(m,2H); 6.75(d, 2H); 7.8(dd,2H);8.0–8.2(m,5H);8.3–8.4(m,3H); 8.85(s,1H);

Mass Spectrum m/z 604 m+H;

Elemental Analysis Found C, 53.5; H, 3.5; N, 7.0. C27H21BrF3N3O3S Requires C, 53.7; H, 3.5; N, 6.95.

4-(6-Bromonaphth-2-ylsulphonyl-2-trifluoromethylbenzoic acid used as starting material may be prepared as follows.

i) A mixture of 6-bromonaphthalene-2-thiol (956 mg) and 4-fluoro-2-trifluoromethyl benzonitrile (756 mg) in dimethylformamide (15 ml), at ambient temperature, was treated dropwise with triethylamine (504 mg). After stirring at ambient temperature for 3 hours the reaction mixture was diluted with ethyl acetate (100 ml), washed with water (3×25 ml) and brine (25 ml), dried (MgSO4) and evaporated to give a yellow oil. Crystallisation from methanol (20 ml) gave 4-(6-bromonaphth-2-ylthio)-2-trifluoromethylbenzonitrile (1.176 g, mp 114–116° C.;

NMR Spectrum 7.4(d,1H); 7.6(d,1H); 7.75(m,2H); 7.9–8.1(m,3H); 8.3(s,2H);

Mass Spectrum m/z 407 m+;

Elemental Analysis Found C, 53.1; H, 2.2; N, 3.4. C18H9BrF3NS Requires C, 53.0; H, 2.2; N, 3.4.

ii) A mixture of nitrile from (i) above (1.0 g), potassium hydroxide (0.6 g), water (3 ml) and ethylene glycol (20 ml) was heated at 155° C. for 24 hours. The mixture was cooled to ambient temperature, diluted with water (100 ml), washed with ether (2×50 ml) and acidified to pH2 with 2M HCl and extracted with ethyl acetate (3×50 ml). The combined extracts were washed with water (2×50 ml) and brine (50 ml), dried (MgSO4) and evaporated to give 4-(6-bromonaphth-2-ylthio)-2-trifluoromethylbenzoic acid as a solid (576 mg);

Mass Spectrum m\z 425 m−H.

The acid from (ii) above (1 g) was suspended in glacial acetic acid (20 ml). Sodium perborate (1.43 g) was added and the mixture stirred at ambient temperature for 24 hours. After cooling to ambient temperature, water (100 ml) was added and the product extracted with ethyl acetate (2×50 ml). The combined extracts were washed with water (3×20 ml) and brine (20 ml), dried (MgSO4) and evaporated togive 4-(6-bromonaphth-2-ylsulphonyl-2-trifluoromethylbenzoic acid (1.0 g);

NMR Spectrum 7.8(dd,1H); 7.9–8.1(m,2H); 8.1–8.2(m, 2H); 8.3–8.4(m,3H); 8.55(s,1H);

Mass Spectrum m/z 457 m−H.

EXAMPLE 32

To the acid from part (ii) of Example 31 (519 mg) in dimethylformamide (10 ml) was added carbonyl diimidazole (196 mg). After stirring at ambient temperature for 30 minutes N-(4-pyridyl)piperazine (198 mg) was added and stirring continued for 24 hours. The reaction mixture was diluted with ethyl acetate (100 ml), washed with water (2×50 ml) and brine (25 ml), dried (MgSO4) and evaporated to give an oil which was further purified by chromatography on silica gel (Mega Bond Elut column, eluted with dichloromethane containing increasing proportions of methanol, 0–4%) to give 1-[4-(6-bromonaphth-2-ylthio)-2-trifluoromethylbenzoyl]-4-(4-pyridyl)piperazine (128 mg);

NMR Spectrum 3.2(m,4H); 3.4(m,4H); 3.7(m,2H); 6.8 (md,2H); 7.4–7.8(m,5H); 7.95(d,1H); 8.0(d,1H); 8.1–8.2(m, 3H); 8.3(s,1H);

Mass Spectrum m\z 572 m+H;

Elemental Analysis Found C, 56.7; H, 3.9; N, 7.2. C27H21BrF3N3OS Requires C, 56.7; H, 3.7; N, 7.3.

EXAMPLE 33

4-(6-Bromonaphth-2-ylthio)-2-carboxybenzoic acid (200 mg) was suspended in acetic anhydride (5 ml) and heated to 120° C. for 1 hour. The precipitate of the anhydride that was obtained on cooling was recovered by filtration, washed with hexane and suspended in dimethylformamide (2 ml). N-(4-Pyridyl)piperazine (76 mg) was added and the mixture stirred at ambient temperature for 3 hours. Ether (20 ml) was added with vigourous stirring and the resulting white solid precipitate was recovered by filtration, washed with ether and dried in vacuo to give 1-[4-(6-bromonaphth-2-ylthio)-2-carboxybenzoyl]-4-(4-pyridyl)piperazine and 1-[5-(6-bromonaphth-2-ylthio)-2-carboxybenzoyl]-4-(4-pyridyl)piperazine (80 mg) as a mixture of two isomers;

NMR Spectrum 3.1–4.0 (m,16H); 6.7–6.9 (m,4H); 7.1 (s,1H); 7.25(d,1H); 7.3(d,1H); 7.4–7.6 (m,3H); 7.7(d,2H); 7.75(s,1H); 7.8–8.0(m,6H); 8.05–8.2 (m,5H); 8.3(s,2H);

Mass Spectrum m\z 548 m+H.

EXAMPLE 34

5-(6-Bromonaphth-2-ylsulphonyl)-2-methoxycarbonylbenzoic acid(97 mg) was dissolved in dichloromethane (1 ml.). Oxalyl chloride (126 mg) was added and the mixture stirred at ambient temperature for 1 hour. The mixture was evaporated to give a solid which was redissolved in dichloromethane (1 ml) and added to a solution of N-(4-pyridyl)piperazine (34 mg) and triethylamine (108 mg) in dichloromethane (2 ml). After stirring for 2 hours at ambient temperature the mixture was diluted with ethyl acetate (100 ml), washed with water (2×25 ml), dried (MgSO4) and evaporated to give an oil, which was further purified by chromatography (Mega Bond Elut column, eluted with dichloromethane containing an increasing proportion of methanol, 0–5%) to give 1-[5-(6-bromonaphth-2-ylsulphonyl)-2-methoxycarbonylbenzoyl]-4-(4-pyridyl)piperazine (55 mg);

NMR Spectrum 3.1–3.2(m,4H); 3.4–3.5(m,2H); 3.7–3.75 (m,2H); 3.8(s,3H); 6.8(d,2H); 7.8(dd,1H); 8.0(dd,1H); 8.05 (s,1H); 8.1–8.2(m,6H); 8.4(s,1H); 8.8(s,1H);

Mass Spectrum m\z 594 m+H;

Elemental Analysis Found C, 55.7; H, 4.3; N, 6.8. C228H24BrN3O5S.0.5H2O Requires C, 55.7; H, 4.18; N, 6.96.

The benzoic acid used as starting material was prepared as follows.

5-(6-Bromonaphth-2-ylsulphonyl)phthalic anhydride [Example 18] (208 mg) was suspended in methanol (10 ml) and heated to reflux for 2 hours. The reaction mixture was evaporated and dried under vacuum to give a mixture of two isomeric esters 4-(6-bromonaphth-2-ylsulphonyl)-2-methoxycarbonylbenzoic acid and 5-(6-bromonaphth-2-ylsulphonyl-2-methoxycarbonylbenzoic acid (210 mg). Flash column chromatography on silica gel, eluting with a mixture of ethyl acetate/methanol/acetic acid 94/5/1, gave a sample of the single isomer used above (97 mg);

NMR Spectrum 3.8(s,3H), 7.8–7.9(m,2H); 8.0(dd,1H); 8.15(d,1H); 8.2(d,1H); 8.3(dd,1H); 8.35(s,1H); 8.4(s,1H); 8.8(s,1H);

Mass Spectrum m\z 449 m+H.

EXAMPLE 35

A mixture of the two isomeric esters, from the part of Example 34 relating to the preparation of starting material, (449 mg) was dissolved in dichloromethane (10 ml). Oxalyl chloride (0.4 ml) was added and the mixture stirred at ambient temperature for 1 hour. The mixture was evaporated to give a solid which was redissolved in dichloromethane (5 ml.) and added dropwise to a solution of N-(4-pyridyl)piperazine (163 mg) and triethylamine (504 mg) in dichloromethane (10 ml). After stirring for 24 hours at ambient temperature the mixture was diluted with ethyl acetate (10 ml), washed with water (3×25 ml) and brine (25 ml), dried (MgSO4) and evaporated to give a solid, which was further purified by chromatography (Mega Bond Elut column, eluted with dichloromethane containing an increasing proportion of methanol, 0–5%) to give a mixture of 1-[4-(6-bromonaphth-2-ylsulphonyl)-2-methoxycarbonylbenzoyl]-4-(4-pyridyl)piperazine and 1-[5-(6-bromonaphth-2-ylsulphonyl)-2-methoxycarbonylbenzoyl]-4-(4-pyridyl)piperazine (461 mg);

NMR Spectrum CDCl3 300 MHz 3.2–3.49(m,8H); 3.4–3.6(m,4H); 3.8–4.0(m, 10H); 6.6–6.7(m,2H); 6.6–6.7 (m,2H); 7.45(d,1H); 7.7–7.45(m,2H); 7.8–8.0(m,7H); 8.05–8.2(m,5H); 8.3–8.4(m,4H); 8.5–8.6(m,2H); 8.7(s,1H);

Mass Spectrum m\z 594 m+H;

Elemental Analysis Found C, 52.9; H, 4.1; N, 6.8. C28H24BrN3O5S.0.5CH2Cl2 Requires C, 52.7; H, 3.9; N, 6.4.

EXAMPLE 36

To the isomeric mixture of acids produced in Example 18 (578 mg) was added, dimethylformamide (10 ml), hydroxybenztriazole (162 mg), 2-(ethylthio)ethylamine (210 mg) and EDAC (382 mg). The mixture was stirred at ambient temperature for 18 hours, diluted with ethyl acetate (100 ml), washed with water (3×25 ml) and brine (25 ml), dried and evaporated. The residue was purified by chromatography (Mega Bond Elut column, eluted with dichloromethane containing an increasing proportion of methanol, 0–5%) to give as a mixture (420 mg) of isomers, 1-[4-(6-bromonaphth-2-ylsulphonyl)-2-(2-(ethylthio)-ethylaminocarbonyl)benzoyl]-4-(4-pyridyl)piperazine and 1-[5-(6-bromonaphth-2-ylsulphonyl)-2-(2-ethylthio) ethylaminocarbonyl)benzoyl]-4-(4-pyridyl)piperazine;

NMR Spectrum 1.1–1.2(m,3H); 2.5–2.6(m,4H); 3.1–3.5 (m,8H); 3.6–3.75(m,2H); 6.7–6.8(m,2H); 7.6–8.4(m,9H); 8.7–9.0(m,2H);

Mass Spectrum m\z 667 m+H;

Elemental Analysis Found C, 54.0; H, 4.6; N, 8.1. $C_{31}H_{31}BrN_4O_4S_2.H_2O$ Requires C, 54.3; H, 4.8; N, 8.2.

A sample of the mixed isomers (100 mg.) was separated by HPLC, C18 ODS column eluted with an acetonitrile/water mixture, to give the 5-naphthylsulphonyl isomer (29 mg).

NMR Spectrum 500 MHz $CH_3CN/D_2O$ 1.08(t,3H); 2.4–2.5(m,2H); 2.6–2.7(m,2H); 3.25–3.3(m,2H); 3.35–3.4 (m,2H); 3.45–3.5(m,2H); 3.7–3.72(m,4H); 6.8–6.9(m,2H); 7.72(dd,1,H);7.78(d,1H);7.85(dd,1H); 7.91(s,1H); 7.95–8.0 (m,4H); 8.07(d,1H); 8.18(s,1H); 8.6(s,1H);

Mass Spectrum m\z 667 m+H.

EXAMPLE 37

A solution of the isomeric mixture of acids produced in Example 18 (prepared in situ, from the phthalic anhydride (208 mg) and N-(4-pyridyl)piperazine (81.5 mg)) in dimethylformamide (5 ml.) was treated with carbonyl diimidazole (97.0 mg) and stirred at ambient temperature for 30 minutes. Piperidine (63 mg) was then added. The mixture was stirred at ambient temperature for 18 hours, diluted with ethyl acetate (100 ml), washed with water (3×20 ml) and brine (20 ml), dried and evaporated. The residue was purified by chromatography (Mega Bond Elut column, eluted with dichloromethane containing an increasing proportion of methanol, 0–5%) to give as a mixture (210 mg) of isomers, 1-[4-(6-bromonaphth-2-ylsulphonyl)-2-(piperidin-1-ylcarbonyl]-4-(4-pyridyl)piperazine and 1-[5-(6-bromonaphth-2-ylsulphonyl)-2-(piperidin-1-ylcarbonyl]-4-(4-pyridyl)piperazine (210 mg);

NMR Spectrum 1.3–1.6(m,6H); 3.0–3.6(m,12H); 6.7(d, 2H); 7.6–7.7(m1H); 7.8(dd,1H); 8.0–8.2 (m,7H); 8.4(s,1H); 8.8(s,1H);

Mass Spectrum m\z 647 m+H

Elemental Analysis Found C, 58.3; H, 5.0; N, 8.8. $C_{32}H_{31}BrN_4O_4S.0.5H_2O$ Requires C, 58.5; H, 4.9; N, 8.5.

EXAMPLE 38

4-(Chlorosulphonyl)benzoic acid (0.75 g) was added to a solution of 1-(3-chlorophenyl)piperazine dihydrochloride (0.90 g) in triethylamine (2.4 ml) and dichloromethane (50 ml). The reaction mixture was stirred overnight at room temperature then concentrated in vacuo. The resulting solid was suspended in N,N-dimethylformamide (50 ml) and carbonyl diimidazole (0.55 g) was added. The reaction mixture was stirred for one hour at room temperature then 1-(4-pyridyl)piperazine (0.55 g, 3.4 mmol) was added. The reaction mixture was stirred for three hours, then concentrated in vacuo. The resulting solid was separated between ethyl acetate (100 ml) and water (100 ml). The ethyl acetate layer was washed with aqueous saturated sodium bicarbonate solution (100 ml) then dried over magnesium sulphate, filtered and concentrated in vacuo. The resulting yellow oil was subjected to chromatography ($SiO_2$: 10%–12% MeOH/EtOAc) to yield 1-[4-(4-(3-chlorophenyl)piperazin-1-ylsulphonyl)benzoyl]-4-(4-pyridyl)piperazine as a white solid (300.1 mg);

NMR Spectrum 3.08 (m, 4H), 3.42 (m, 10H) 3.75ppm (s, 2H, 6.81 (m, 3H), 6.8 (dd, 1H chlorophenyl 4H), 6.94 (t, 1H) 7.21 (t, 1H, 7.72 & 7.86(dd, 4H, phenyl 8.18 (d, 2H);

Mass Spectrum 528 (M+H)$^+$;

Elemental Analysis Found Carbon 57.8%, hydrogen 5.5%, nitrogen 12.3% (Calc. for $C_{26}H_{28}ClN_5O_3S.0.2EtOAc.0.8H_2O$ Carbon 57.7%, hydrogen 5.63%, nitrogen 12.5%).

EXAMPLE 39

4-(-Chlorosulphonyl)benzoic acid (733.0 mg) was added to a solution of 6-chloro-1,2,3,4-tetrahydroisoquinoline (558.1 mg) in triethylamine (0.46 ml) and tetrahydrofuran (20 ml). The reaction mixture was stirred for two days at room temperature then concentrated in vacuo to yield 4-[6-chloro-1,2,3,4-tetrahydroisoquinolin-2-ylsulphonyl]benzoic acid as an off white solid. This was suspended in dichloromethane (30 ml) and carbonyl diimidazole (539 mg) was added. The reaction mixture was stirred for one hour at room temperature then 1-(4-pyridyl)piperazine (541 mg) was added. The reaction mixture was stirred overnight, then concentrated in vacuo. The resulting solid was separated between ethyl acetate (50 ml) and water (2×100 ml). The ethyl acetate layer was dried over magnesium sulphate, filtered and concentrated in vacuo. The resulting solid was subjected to chromatography ($SiO_2$: 1–5% Methanol/ethyl acetate) to yield 1-[4-(6-chloro-1,2,3,4-tetrahydroisoquinolin-2-ylsulphonylbenzoyl]-4-(4-pyridyl) piperazine a white solid (984.7 mg);

NMR Spectrum ($CDCl_3$, 300 MHz) 2.66 (t, 2H), 3.22 to 3.58 (s, 6H), 3.41 (t, 2H), 3.93 (s, 2H), 4.28 (s, 2H), 6.68 (m. 2H, 6.98 (d, 1H), 7.09 (s, 1H), (dd, 1H, quinoline 6-H), 7.58 and 7.90 (dd, 4H, phenyl Ar H's), 8.33 (d, 2H, pyridyl 2-H & 6-H);

Mass Spectrum 497 (M+H)$^+$;

Elemental Analysis Found Carbon 58.1%, hydrogen 4.8%, nitrogen 10.6% (Calc. for $C_{25}H_{25}ClN_4O_3S.0.25CH_2Cl_2$ Carbon 58.5%, hydrogen 4.96%, nitrogen 10.8%).

The 6-Chloro-1,2,3,4-tetrahydroisoquinoline may be prepared as follows:

i) 2-(m-Chlorophenyl)ethylamine (21.92 g) was dissolved in pyridine (250 ml) and cooled to 0° C. Tosyl chloride (40.28 g) was added portionwise as a solid over one hour keeping the temperature below 5° C. The reaction mixture was stirred for two hours at room temperature then concentrated in vacuo. The resulting oil was dissolved in dichloromethane (500 ml) and washed twice with 2N aqueous hydrochloric acid (2×400 ml). The dichloromethane layer was dried over magnesium sulphate, filtered and concentrated in vacuo. The resulting oil was subjected to chromatography ($SiO_2$: 100% $CH_2Cl_2$) to yield the toluenesulphonyl derivative of the amine as a white solid (7.59 g);

NMR Spectrum ($CDCl_3$) 2.42 (s, 3H), 2.73 (t, 2H, 3.21 (q, 2H), 4.38 (t, 1H), 6.98 (t, 1H), 7.01 (s, 1H), 7.20 (d, 2H, 4-H and 6-H), 7.30 and 7.69 (dd, 4H);

Mass Spectrum 310 (M+H)$^+$;

Elemental Analysis Found Carbon 57.4%, hydrogen 5.29%, nitrogen 4.40% (Calc. for $C_{15}H_{16}ClNO_2 \cdot 0.25H_2O$ Carbon 57.3%, hydrogen 5.20%, nitrogen 4.46%).

ii) To a solution of the tosylated amine from i) above (5.0 g) in chloroform (50 ml) was added formaldehyde 37 wt. % solution in water (2.62 ml) followed by phosphoryl trichloride (40 ml). The reaction mixture was stirred under reflux for three hours. The reaction mixture was cooled to room temperature then poured into a stirred mixture of dichloromethane (150 ml) and aqueous saturated sodium bicarbonate solution (150 ml). Solid sodium bicarbonate was added portionwise with caution until the aqueous layer became basic. The dichloromethane layer was separated, washed with water (200 ml) then dried over magnesium sulphate, filtered and concentrated in vacuo. The crude product was subjected to chromatography ($SiO_2$: 10–15% Ethyl acetate/iso-hexane) to yield 4-(6-chloro-1,2,3,4-tetrahydroisoquinolin-2-ylsulphonyl)toluene as a white crystalline solid which was recrystallised from ethyl acetate/iso-hexane (2.26 g);

NMR Spectrum ($CDCl_3$, 250 MHz) 2.38 (s, 3H), 2.89 (t, 2H), 3.31 (t, 2H), 4.17 (s, 2H), 6.95 (d, 1H), 7.06 (s, 1H), 7.12 (d, 1H), 7.31 and 7.71 (dd, 4H);

Mass Spectrum 322 (M+H)$^+$;

Elemental Analysis Found Carbon 60.0%, hydrogen 5.00%, nitrogen 4.30% (Calc. for $C_{16}H_{16}ClNO_2S$ Carbon 59.7%, hydrogen 5.01%, nitrogen 4.35%).

iii) Part of the product from ii) above (2.20 g, 6.8 mmol) was heated at 75° C. with phenol (2.25 g) and 45% w/w hydrobromic acid in glacial acetic acid (30 ml) for three hours. The reaction mixture was cooled to room temperature then poured onto a mixture of ice and dichloromethane. The aqueous layer was adjusted to pH 14 with 6N sodium hydroxide solution and extracted with dichloromethane (4×100 ml). The dichloromethane layers were combined then dried over magnesium sulphate, filtered and concentrated in vacuo. The crude product was subjected to chromatography ($SiO_2$: 1–10% methanol/dichloromethane) to yield 6-chloro-1,2,3,4-tetrahydroisoquinoline as a colourless oil (558.1 mg);

NMR Spectrum 2.66 (t, 2H), 2.88 (q, 2H), 3.78 (s, 2H), 6.98 to 7.13 (m, 3H, Ar H's);

Mass Spectrum 168 (M+H)$^+$.

EXAMPLE 40

To a solution of 5-methoxyindole-2-carboxylic acid (168 mg, 0.88 mmol) in DMF (4 ml) was added 1-(3-dimethylaminopropyl)-3-ethylcarbodiimide hydrochloride (168 mg, 0.88 mmol), 1-hydroxybenzotriazole (118 mg, 0.88 mmol) and $Et_3N$ (0.12 ml, 0.88 mmol) followed by 1-(4-pyridyl)-3-(5-amino-2-pyridyloxy)pyrrolidine (150 mg, 0.58 mmol) and the resulting suspension stirred at room temperature for 7 days. The mixture was poured into saturated aqueous $NaHCO_3$ solution and the solid precipitate collected by filtration and washed with water then dried (over $P_2O_5$) to give 1-(4-pyridyl)-(5-(6-methoxyindol-2-ylcarbonylamino)pyrid-2-yloxy)pyrrolidine as an off white solid (195 mg);

NMR Spectrum ($CDCl_3$) 2.20 (m, 2H), 3.50 (m, 4H), 3.80 (s, 3H), 5.70 (m, 1H), 6.60 (m, 2H), 6.90 (m, 2H), 7.15 (s, 1H), 7.30 (m, 2H), 8.10 (m, 3H), 8.60 (s, 1H).

MS (ESP+): m/e 430 (M+H)$^+$.

The 1-(4-pyridyl)-3-(5-amino-2-pyridyloxy)pyrrolidine starting material may be prepared as follows:

(a) Sodium hydride (60% dispersion in paraffin oil, 146 mg) 1.2 equivalent) was added to an oven-dried round-bottomed flask and washed under an argon atmosphere with pentane. DMF (5 ml) was then added, followed by 1-(4-pyridyl)-3-hydroxypyrrolidine (1.0 equivalent, 3.05 mmol) and tetra-n-butylammonium bromide (59 mg, 0.18 mmol). The mixture was added as a slurry to 2-bromo-5-nitropyridine (1.5 equivalent) in a second dry flask under argon, with stirring. After the reaction was complete the solvent was evaporated under vacuum. The residue was purified by chromatography on silica, eluting from 1%MeOH/1%NH$_4$OH/CH$_2$Cl$_2$ to 10%MeOH/1%NH$_4$OH/CH$_2$Cl$_2$ (in 1% increments). The crude product was recrystallised from EtOAc to give 1-(4-pyridyl)-3-(5-nitro-2-pyridyloxy)pyrrolidine as a pale brown solid (460 mg);

NMR Spectrum ($CDCl_3$): 2.4 (m, 2H), 3.58 (m, 3H), 3.8 (dd, 1H), 5.85 (m, 1H), 6.4 (d, 2H), 6.82 (d, 1H), 8.22 (m, 2H), 8.38 (dd, 1H), 9.08 (s 1H).

MS (ESP+): m/e 287 (M+H)$^+$.

(b) A solution of 1-(4-pyridyl)-3-(5-nitro-2-pyridyloxy)pyrrolidine (15.29 g, 53.46 mmol) in methanol (500 ml) was hydrogenated over 10% Pd/C at 5 bar for 18 h. The catalyst was removed by filtration and the solvent evaporated to give the product as a pale yellow solid (12.68 g).

NMR Spectrum ($CDCl_3$): 2.30 (m, 2H), 3.40 (m, 5H), 3.70 (dd, 1H), 5.60 (m, 1H), 6.40 (d, 2H), 6.60 (d, 1H), 7.00 (m, 1H), 7.60 (s, 1H), 8.10 (d, 2H).

MS (ESP+): m/e 257 (M+H)$^+$.

EXAMPLE 41

A mixture of 1-(2-methylpyrid-4-yl)piperazine dihydrochloride (145 mg), triethylamine (0.16 ml), N-hydroxysuccinimide ester from part (iv) of Example 26 (244 mg) and DMF (10 ml) was stirred for 16 hours. The solvent was evaporated and the residue dissolved in methylene chloride and washed with water. The aqueous washings were extracted with further methylene chloride and the combined organic extracts dried ($MgSO_4$) and evaporated. The residue was further purified by column chromatography using a 9:1 mixture of methylene chloride and methanol as eluant and the resulting solid triturated under diethyl ether. There was thus obtained 1-[4-(6-bromonaphth-2-ylsulphonyl)benzoyl]-4-(2-methylpyrid-4-yl)piperazine (115 mg);

NMR Spectrum (DMSO-d$^6$+D$_2$O) 2.28 (s, 3H), 3.20–3.48 (m, 6H), 3.66 (bs, 2H), 6.61 (d, 1H), 6.67 (s, 1H), 7.63 (d, 2H), 7.80 (d, 1H), 7.97 (t, 2H), 8.06–8.17 (m, 4H), 8.32 (s, 1H), 8.72 (s, 1H);

Mass Spectrum m/z 550/552 (M+H);

Elemental Analysis Found C, 57.7; H, 4.2; N, 7.7; S, 5.8. $C_{27}H_{24}BrN_3O_3S \cdot 0.5H_2O$ requires: C, 58.0; H, 4.5; N, 7.5; S, 5.7%.

EXAMPLE 42

The ester from Example 26 (iv) above (488 mg) was treated with 1-(4-pyridyl)hexahydro-1,4-diazepine (195 mg) in dimethylformamide (10 ml) and stirred at ambient temperature for 18 hours. After removal of the solvent in vacuo and addition of ethyl acetate (30 ml), washing with saturated sodium bicarbonate solution (30 ml), water (2×30 ml) and brine (30 ml), the reaction mixture was dried (MgSO4) and evaporated to a white solid. Purification by column chromatography on silica gel, eluting with dichloromethane containing an increasing proportion of methanol (2–5%) and a small amount of conc. aqueous ammonia, followed by recrystallisation from ethyl acatate gave as a solid 1-[4-(6-bromonaphth-2-ylsulphonyl)benzoyl]-4-(4-pyridyl) hexahydro-1,4-diazepine (290 mg).

NMR Spectrum (CDCl$_3$) 2.0–2.2 (m, 2H); 3.3 (m, 1H); 3.4–3.5 (m, 1H); 3.6–3.8(bm,5H); 4.0 (m,1H); 6.7(d,2H); 7.05(m,1H); 7.4(dd,1H); 7.7 (m,1H); 7.9 (m,3H); 8.0 (m,2H); 8.1 (m,1H); 8.15–8.5(m,2H); 8.55(s,1H).

Mass Spectrum m/z 550/552 m+H.

Elemental Analysis Found C, 58.8; H, 4.6; N, 7.1; S: 5.2%. C27H24BrN3O3S Requires C, 58.6; H, 4.7; N, 7.1; S, 5.4%.

The 1-(4-pyridyl)hexahydro-1,4-diazepine used as starting material may be prepared as follows:

A suspension of 4-chloropyridine hydrochloride (7.5 g) in 3-methyl-1-butanol (100 ml) was added dropwise to a refluxing solution of hexahydro-1,4-diazepine (10.0 g) and triethylamine (16.8 ml) in 3-methyl-1-butanol (300 ml). After addition the solution was refluxed for 18 hours. The solvent was removed in vacuo to give an oil. Purification by sinter-column chromatography on silica gel, eluting with dichloromethane containing an increasing proportion of methanol (2–5%) and a small amount of conc. aqueous ammonia, gave 1-(4-pyridyl)hexahydro-1,4-diazepine as a colourless oil which slowly crystallised on standing.

NMR Spectrum (CDCl$_3$) 1.8–2.1 (m, 2H); 2.8 (m, 2H); 3.0 (m, 2H); 3.4–3.7 (m,5H); 6.5(d,2H); 8.2 (d,2H).

Mass Spectrum m/z 178 m+H.

EXAMPLE 43

The following illustrate representative pharmaceutical dosage forms containing the compound of formula I, or a pharmaceutically-acceptable salt thereof (hereafter compound X), for therapeutic or prophylactic use in humans:

|  | mg/tablet |
|---|---|
| (a) Tablet I | |
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

|  | mg/capsule |
|---|---|
| (d) Capsule | |
| Compound X | 10 |
| Lactose Ph.Eur | 488.5 |
| Magnesium stearate | 1.5 |

|  | (50 mg/ml) |
|---|---|
| (e) Injection I | |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |

|  | (10 mg/ml) |
|---|---|
| (f) Injection II | |
| Compound X | 1.0% w/v |
| Sodium phosphate BP | 3.6% w/v |
| 0.1M Sodium hydroxide solution | 15.0% v/v |
| Water for injection to 100% | |

|  | (1 mg/ml, buffered to pH 6) |
|---|---|
| (g) Injection III | |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means, for example to provide a coating of cellulose acetate phthalate.

What is claimed is:

1. An aminoheterocyclic compound of the formula I

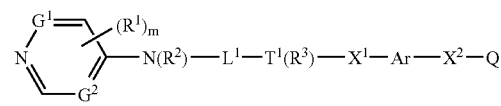

wherein
G$^1$ is CH;
G$^2$ is CH;
m is 1 or 2;
R$^1$ is hydrogen, halogeno, trifluoromethyl, trifluoromethoxy, cyano, amino, hydroxy, nitro, (1–4C)alkyl, (1–4C)alkoxy, (1–4C)alkylamino or di-(1–4C)alkylamino;
L$^1$ is (1–4C)alkylene or (3–6C)cycloalkane-1,2-diyl,
T$^1$ is CH or N, and
R$^2$ and R$^3$ together form a (1–4C)alkylene or methylenecarbonyl group,
and wherein 1 or 2 methylene groups within L$^1$ or the ring formed when R$^2$ and R$^3$ are linked optionally bear 1 or 2 substituents selected from carboxy, carbamoyl, (1–4C)alkyl, (1–4C)alkoxycarbonyl, N-(1–4C)alkylcarbamoyl, N,N-di-(1–4C)alkylcarbamoyl, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl and N,N-di-(1–4C)alkylcarbamoyl-(1–4C)alkyl,
provided that, when T$^1$ is N, L$^1$ is not optionally substituted methylene and R$^2$ and R$^3$ together do not form an optionally substituted methylene group;
X$^1$ is a group of the formula SO, SO$_2$, C(R$^4$)$_2$, CO, C(R$^4$)$_2$O, C(R$^4$)$_2$S, C(R$^4$)$_2$SO, C(R$^4$)$_2$SO$_2$, COC(R$^4$)$_2$, SOC(R$^4$)$_2$ or SO$_2$C(R$^4$)$_2$ when T$^1$ is CH or N, or, in addition, X$^1$ is a group of the formula O, S, OC(R$^4$)$_2$ or SC(R$^4$)$_2$ when T$^1$ is CH, and wherein each R$^4$ is independently hydrogen or (1–4C)alkyl;

Ar is a 1,3-phenylene or 1,4-phenylene, wherein said phenylene ring is optionally substituted with 1 or 2 substituents selected
  from halogeno, trifluoromethyl, trifluoromethoxy, cyano, nitro, (1–4C)alkyl, (2–4C)alkenyl and (2–4C)alkynyl,
  from the substituent $Y^1$ which is selected from hydroxy, amino, (1–4C)alkoxy, (2–4C)alkenyloxy, (2–4C)alkynyloxy, (1–4C)alkylamino, di-(1–4C)alkylamino, (1–4C)alkylthio, (1–4C)alkylsulphinyl, (1–4C)alkylsulphonyl, (2–4C)alkanoylamino, benzamido, (1–4C)alkanesulphonamido and benzenesulphonamido,
  from the substituent $Y^2$ which is selected from carboxy, carbamoyl, (1–4C)alkoxycarbonyl, N-(1–4C)alkylcarbamoyl, N,N-di-(1–4C)alkylcarbamoyl, (1–4C)alkanesulphonamidocarbonyl, benzenesulphonamidocarbonyl and benzylsulphonamidocarbonyl,
  from a substituent of the formula —$L^2$—$Y^1$ wherein $L^2$ is (1–4C)alkylene and $Y^1$ has any of the meanings defined immediately hereinbefore,
  from a substituent of the formula —$L^2$—$Y^2$ wherein $L^2$ is (1–4C)alkylene and $Y^2$ has any of the meanings defined immediately hereinbefore,
  from a substituent of the formula —$X^3$—$L^2$—$Y^2$ wherein $X^3$ is a group of the formula CON($R^5$), CON($L^2$—$Y^2$), C($R^5$)$_2$O, O, N($R^5$) or N($L^2$—$Y^2$), $L^2$ is (1–4C)alkylene, $Y^2$ has any of the meanings defined immediately hereinbefore and each $R^5$ is independently hydrogen or (1–4C)alkyl, and
  from a substituent of the formula —$X^3$—$L^3$—$Y^1$ wherein $X^3$ is a group of the formula CON($R^5$), CON($L^3$—$Y^1$), C($R^5$)$_2$O, O, N($R^5$) or N($L^3$—$Y^1$), $L^3$ is (2–4C)alkylene, $Y^1$ has any of the meanings defined immediately hereinbefore and each $R^5$ is independently hydrogen or (1–4C)alkyl,
  and wherein any phenyl group in said substituent optionally bears 1 or 2 substituents selected from halogeno, trifluoromethyl, cyano, (1–4C)alkyl, (2–4C)alkenyl, (2–4C)alkynyl, (1–4C)alkoxy, (2–4C)alkenyloxy and (2–4C)alkynyloxy;

$X^2$ is a group of the formula S, SO, SO$_2$, C($R^6$)$_2$, CO, N($R^7$)SO$_2$, N($R^7$)CO, C($R^6$)$_2$S, C($R^6$)$_2$SO, C($R^6$)$_2$SO$_2$, C($R^6$)$_2$—C($R^6$)$_2$ or C($R^6$)$_2$CO, or, in addition, $X^2$ is a group of the formula O, SO$_2$N($R^7$), CON($R^7$) or C($R^6$)$_2$O when Q is other than phenyl-(2–4C)alkenyl or phenyl-(2–4C)alkynyl and wherein each $R^6$ is independently hydrogen or (1–4C)alkyl and $R^7$ is hydrogen, (1–4C)alkyl or a group of the formula —$X^4$—Q wherein $X^4$ is SO$_2$ or CO and Q has any of the meanings defined immediately hereinafter; and Q is phenyl, naphthyl, phenyl-(1–4C)alkyl, phenyl-(2–4C)alkenyl or phenyl-(2–4C)alkynyl, and Q optionally bears 1, 2 or 3 substituents selected from halogeno, trifluoromethyl, trifluoromethoxy, cyano, hydroxy, amino, nitro, trifluoromethanesulphonyl, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, phenyl, phenoxy, phenylthio, phenylsulphinyl, phenylsulphonyl, benzyl and benzoyl, and wherein said phenyl, phenoxy, phenylthio, phenylsulphinyl, phenylsulphonyl, benzyl or benzoyl substituent optionally bears 1, 2 or 3 substituents selected from halogeno, trifluoromethyl, cyano, hydroxy, amino, nitro, carboxy, carbamoyl, (1–4C)alkyl, (1–4C)alkoxy, (1–4C)alkylamino, di-(1–4C)alkylamino, (1–4C)alkoxycarbonyl, N-(1–4C)alkylcarbamoyl, N,N-di-(1–4C)alkylcarbamoyl and (2–4C)alkanoylamino;

or a pharmaceutically-acceptable salt thereof;

provided that when $X^1$ is CO and Ar is phenylene which optionally bears 1 or 2 substituents selected from halogeno, trifluoromethyl, (1–4C)alkyl and (1–4C)alkoxy then $X^2$ is not N($R^7$)SO$_2$, N($R^7$)CO, C($R^6$)$_2$S, C($R^6$)$_2$SO, C($R^6$)$_2$SO$_2$, C($R^6$)$_2$—C($R^6$)$_2$, C($R^6$)$_2$CO or C($R^6$)$_2$O.

2. The compound according to claim 1 wherein:
  each of $G^1$ and $G^2$ is CH;
  m is 1; and
  $R^1$ is hydrogen;
  $L^1$ is (1–4C)alkylene,
  $T^1$ is CH or N, and
  $R^2$ and $R^3$ together form a (1–4C)alkylene group,
  and wherein 1 or 2 methylene groups within $L^1$ and the ring formed when $R^2$ and $R^3$ are linked optionally bears 1 or 2 (1–4C)alkyl substituents,
    provided that, when $T^1$ is N, $L^1$ is not optionally substituted methylene and $R^2$ and $R^3$ together do not form an optionally substituted methylene group;
  when $T^1$ is CH or N, $X^1$ is a group of the formula SO$_2$, CH$_2$, CO, CH$_2$O, CH$_2$S, CH$_2$SO$_2$, COCH$_2$ or SO$_2$CH$_2$, or, when $T^1$ is CH, $X^1$ is, in addition, a group of the formula O, S, OCH$_2$ or SCH$_2$;
  Ar is 1,3-phenylene or 1,4-phenylene which is optionally substituted with 1 or 2 substituents selected from halogeno, trifluoromethyl, cyano, (1–4C)alkyl, hydroxy, amino, (1–4C)alkoxy, (1–4C)alkylamino, di-(1–4C)alkylamino, (1–4C)alkylthio, (1–4C)alkylsulphinyl, (1–4C)alkylsulphonyl, (2–4C)alkanoylamino, carboxy, carbamoyl, (1–4C)alkoxycarbonyl, N-(1–4C)alkylcarbamoyl and N,N-di-(1–4C)alkylcarbamoyl; or
  Ar is 1,3-phenylene or 1,4-phenylene which is optionally substituted with a substituent of the formula —$L^2$—$Y^1$ or of the formula —$L^2$—$Y^2$ wherein $L^2$ is (1–4C)alkylene, $Y^1$ is selected from hydroxy, amino, (1–4C)alkoxy, (1–4C)alkylamino, di-(1–4C)alkylamino, (1–4C)alkylthio, (1–4C)alkylsulphinyl, (1–4C)alkylsulphonyl and (2–4C)alkanoylamino, and $Y^2$ is selected from carboxy, carbamoyl, (1–4C)alkoxycarbonyl, N-(1–4C)alkylcarbamoyl and N,N-di-(1–4C)alkylcarbamoyl; or
  Ar is 1,3-phenylene or 1,4-phenylene which is optionally substituted with a substituent of the formula —$X^3$—$L^2$—$Y^2$ wherein $X^3$ is a group of the formula CONH, CON(Me), CH$_2$O or O, $L^2$ is methylene, ethylene or trimethylene and $Y^2$ is selected from carboxy, carbamoyl, (1–4C)alkoxycarbonyl, N-(1–4C)alkylcarbamoyl and N,N-di-(1–4C)alkylcarbamoyl; or
  Ar is 1,3-phenylene or 1,4-phenylene which is optionally substituted with a substituent of the formula —$X^3$—$L^3$—$Y^1$ wherein $X^3$ is a group of the formula CONH, CH$_2$O, O or NH, $L^3$ is ethylene or trimethylene and $Y^1$ is hydroxy, amino, (1–4C)alkoxy, (1–4C)alkylamino, di-(1–4C)alkylamino, (1–4C)alkylthio, (1–4C) alkylsulphinyl, (1–4C)alkylsulphonyl and (2–4C) alkanoylamino;

$X^2$ is a group of the formula $SO_2$, $CH_2$, CO, $NHSO_2$, $N(R^7)SO_2$, NHCO, $N(R^7)CO$, $CH_2SO_2$, $CH_2CH_2$ or $CH_2CO$ wherein $R^7$ is (1–4C)alkyl or a group of the formula —$X^4$—Q wherein $X^4$ is $SO_2$ and Q has any of the meanings defined hereinafter; or $X^2$ is a group of the formula S;

Q is phenyl, naphthyl or phenyl-(1–4C)alkyl which optionally bears 1, 2 or 3 substituents selected from hydroxy, halogeno, cyano, trifluoromethyl, (1–4C)alkyl, (1–4C)alkoxy, phenyl, phenoxy, phenylthio, phenylsulphinyl, phenylsulphonyl, benzyl and benzoyl, and wherein the phenyl substituent or the phenyl group in a phenyl-containing substituent optionally bears 1 or 2 substituents selected from halogeno, (1–4C)alkyl and (1–4C)alkoxy; or Q is phenyl-(2–4C)alkenyl or phenyl-(2–4C)alkynyl which optionally bears 1,2 or 3 substituents selected from halogeno, cyano, trifluoromethyl, (1–4C)alkyl and (1–4C)alkoxy;

or a pharmaceutically-acceptable salt thereof;

provided that when $X^1$ is CO and Ar is phenylene which optionally bears 1 or 2 substituents selected from halogeno, trifluoromethyl, (1–4C)alkyl and (1–4C)alkoxy then $X^2$ is not $N(R^7)SO_2$, $N(R^7)CO$, $C(R^6)_2S$, $C(R^6)_2SO$, $C(R^6)_2SO_2$, $C(R^6)_2$—$C(R^6)_2$, $C(R^6)_2CO$ or $C(R^6)_2O$.

3. An aminoheterocyclic compound of the formula I

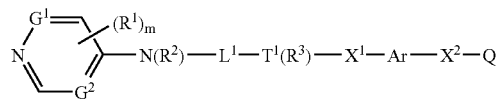

wherein
each of $G^1$ and $G^2$ is CH;
m is 1; and
$R^1$ is hydrogen;
$L^1$ is ethylene,
$T^1$ is CH or N, and
$R^2$ and $R^3$ together form an ethylene group;
when $T^1$ is CH or N, $X^1$ is a group of the formula $CH_2$, CO, $CH_2O$ or $SO_2$, or, when $T^1$ is CH, $X^1$ is, in addition, a group of the formula O;
Ar is 1,3-phenylene or 1,4-phenylene which is optionally substituted with 1 or 2 substituents selected from fluoro, chloro, bromo, trifluoromethyl, cyano, methyl, hydroxy, amino, methoxy, methylamino, dimethylamino, methylthio, methylsulphinyl, methylsulphonyl, acetamido, carboxy, carbamoyl, methoxycarbonyl, ethoxycarbonyl, N-methylcarbamoyl, N,N-dimethylcarbamoyl and 2-(ethylthio)ethylaminocarbonyl;
$X^2$ is a group of the formula S, $SO_2$, CONH, $NHSO_2$ or $N(R^7)SO_2$ wherein $R^7$ is methyl or a group of the formula —$SO_2Q$ wherein Q has any of the meanings defined immediately hereinafter; and
Q is phenyl, styryl, 4-biphenylyl or 2-naphthyl which optionally bears 1 or 2 substituents selected from fluoro, chloro, bromo, trifluoromethyl, 4-chlorophenoxy, methyl and methoxy;
or a pharmaceutically-acceptable salt thereof;
provided that when $X^1$ is CO and Ar is 1,3- or 1,4-phenylene which optionally bears 1 or 2 substituents selected from fluoro, chloro, bromo, trifluoromethyl, methyl and methoxy then $X^2$ is not $NHSO_2$ or $N(R^7)SO_2$ wherein $R^7$ is methyl or a group of the formula —$SO_2$—Q wherein Q has any of the meanings defined immediately hereinbefore.

4. The compound according to claim 1 or 2 wherein
each of $G^1$ and $G^2$ is CH;
m is 1; and
$R^1$ is hydrogen;
$L^1$ is ethylene,
$T^1$ is CH or N, and
$R^2$ and $R^3$ together form an ethylene group;
when $T^1$ is CH or N, $X^1$ is a group of the formula $CH_2$, CO or $CH_2O$, or, when $T^1$ is CH, $X^1$ is, in addition, a group of the formula O;
Ar is 1,3-phenylene or 1,4-phenylene which is optionally substituted with 1 or 2 substituents selected from fluoro, chloro, bromo, trifluoromethyl, cyano, methyl, hydroxy, amino, methoxy, methylamino, dimethylamino, methylthio, methylsulphinyl, methylsulphonyl, acetamido, carboxy, carbamoyl, methoxycarbonyl, ethoxycarbonyl, N-methylcarbamoyl and N,N-dimethylcarbamoyl;
$X^2$ is a group of the formula $SO_2$, $NHSO_2$ or $N(R^7)SO_2$ wherein $R^7$ is methyl or a group of the formula —$SO_2Q$ wherein Q has any of the meanings defined immediately hereinafter; and
Q is phenyl, styryl, 4-biphenylyl or 2-naphthyl which optionally bears 1 or 2 substituents selected from fluoro, chloro, bromo, trifluoromethyl, methyl and methoxy;
or a pharmaceutically-acceptable salt thereof;
provided that when $X^1$ is CO and Ar is 1,3- or 1,4-phenylene which bears 1 or 2 substituents selected from fluoro, chloro, bromo, trifluoromethyl, methyl and methoxy then $X^2$ is not $NHSO_2$ or $N(R^7)SO_2$ wherein $R^7$ is methyl or a group of the formula $SO_2$—Q wherein Q has any of the meanings defined immediately hereinbefore.

5. The compound according to claim 1 or 2 wherein
each of $G^1$ and $G^2$ is CH;
m is 1; and
$R^1$ is hydrogen;
$L^1$ is ethylene,
$T^1$ is N, and
$R^2$ and $R^3$ together form an ethylene group;
$X^1$ is a group of the formula CO;
Ar is 1,4-phenylene or 2-carboxy-1,4-phenylene;
$X^2$ is a group of the formula $SO_2$; and
Q is 2-naphthyl, styryl or 4-biphenylyl which optionally bears 1 or 2 substituents selected from fluoro, chloro and bromo;
or a pharmaceutically-acceptable salt thereof.

6. A compound according to claim 1 or 2 wherein
each of $G^1$ and $G^2$ is CH;
m is 1; and
$R^1$ is hydrogen;
$L^1$ is ethylene,
$T^1$ is N, and
$R^2$ and $R^3$ together form an ethylene group;
$X^1$ is a group of the formula CO;
Ar is 1,4-phenylene or 2-carboxy-1,4-phenylene;
$X^2$ is a group of the formula $SO_2$; and
Q is 2-naphthyl, styryl or 4-biphenylyl which optionally bears 1 or 2 substituents selected from fluoro, chloro and bromo;
or a pharmaceutically-acceptable salt thereof.

7. A method of producing an antithrombotic or anticoagulant effect in a warm-blooded animal in need thereof, which comprises administering to said animal an effective amount of an aminoheterocyclic compound of formula I:

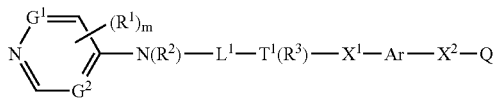

wherein
  G¹ is CH;
  G² is CH;
  m is 1 or 2;
  R¹ is hydrogen, halogeno, trifluoromethyl, trifluoromethoxy, cyano, amino, hydroxy, nitro, (1–4C)alkyl, (1–4C)alkoxy, (1–4C)alkylamino or di-(1–4C)alkylamino;
  L¹ is (1–4C)alkylene, (3–6C)cycloalkane-1,2-diyl or (1–3C)alkylene-carbonyl,
  T¹ is CH or N, and
  R² and R³ together form a (1–4C)alkylene or methylenecarbonyl group,
    and wherein 1 or 2 methylene groups within L¹ or the ring formed when R² and R³ are linked optionally bear 1 or 2 substituents selected from carboxy, carbamoyl, (1–4C)alkyl, (1–4C)alkoxycarbonyl, N-(1–4C)alkylcarbamoyl, N,N-di-(1–4C)alkylcarbamoyl, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl and N,N-di-(1–4C)akylcarbamoyl-(1–4C)alkyl,
  provided that, when T¹ is N, L¹ is not optionally substituted methylene and R² and R³ together do not form an optionally substituted methylene group;
  X¹ is a group of the formula SO, SO₂, C(R⁴)₂, CO, C(R⁴)₂O, C(R⁴)₂S, C(R⁴)₂SO, C(R⁴)₂SO₂, COC(R⁴)₂, SOC(R⁴)₂ or SO₂C(R⁴)₂ when T¹ is CH or N, or, in addition, X¹ is a group of the formula O, S, OC(R⁴)₂ or SC(R⁴)₂ when T¹ is CH, and wherein each R⁴ is independently hydrogen or (1–4C)alkyl;
  Ar is a 1,3-phenylene or 1,4-phenylene, wherein said phenylene ring is optionally substituted with 1 or 2 substituents selected
    from halogeno, trifluoromethyl, trifluoromethoxy, cyano, nitro, (1–4C)alkyl, (2–4C)alkenyl and (2–4C)alkynyl,
    from the substituent Y¹ which is selected from hydroxy, amino, (1–4C)alkoxy, (2–4C)alkenyloxy, (2–4C)alkynyloxy, (1–4C)alkylamino, di-(1–4C)alkylamino, (1–4C)alkylthio, (1–4C)alkylsulphinyl, (1–4C)alkylsulphonyl, (2–4C)alkanoylamino, benzamido, (1–4C)alkanesulphonamido and benzenesulphonamido,
    from the substituent Y² which is selected from carboxy, carbamoyl, (1–4C)alkoxycarbonyl, N-(1–4C)alkylcarbamoyl, N,N-di-(1–4C)alkylcarbamoyl, (1–4C)alkanesulphonamidocarbonyl, benzenesulphonamidocarbonyl and benzylsulphonamidocarbonyl,
    from a substituent of the formula —L²—Y¹ wherein L² is (1–4C)alkylene and Y¹ has any of the meanings defined immediately hereinbefore,
    from a substituent of the formula —L²—Y² wherein L² is (1–4C)alkylene and Y² has any of the meanings defined immediately hereinbefore,
    from a substituent of the formula —X³—L²—Y² wherein X³ is a group of the formula CON(R⁵), CON(L²—Y²), C(R⁵)₂O, O, N(R⁵) or N(L²—Y²), L² is (1–4C)alkylene, Y² has any of the meanings defined immediately hereinbefore and each R⁵ is independently hydrogen or (1–4C)alkyl, and
    from a substituent of the formula —X³—L³—Y¹ wherein X³ is a group of the formula CON(R⁵), CON(L³—Y ), C(R⁵)₂O, O, N(R⁵) or N(L³—Y¹), L³ is (2–4C)alkylene, Y¹ has any of the meanings defined immediately hereinbefore and each R⁵ is independently hydrogen or (1–4C)alkyl,
    and wherein any phenyl group in said substituent optionally bears 1 or 2 substituents selected from halogeno, trifluoromethyl, cyano, (1–4C)alkyl, (2–4C)alkenyl, (2–4C)alkynyl, (1–4C)alkoxy, (2–4C)alkenyloxy and (2–4C)alkynyloxy;
  X² is a group of the formula S, SO, SO₂, C(R⁶)₂, CO, N(R⁷)SO₂, N(R⁷)CO, C(R⁶)₂S, C(R⁶)₂SO, C(R⁶)₂SO₂, C(R⁶)₂—C(R⁶)₂ or C(R⁶)₂CO, or, in addition, X² is a group of the formula O, SO₂N(R⁷), CON(R⁷) or C(R⁶)₂O when Q is other than phenyl-(2–4C)alkenyl or phenyl-(2–4C)alkynyl and wherein each R⁶ is independently hydrogen or (1–4C)alkyl and R⁷ is hydrogen, (1–4C)alkyl or a group of the formula —X⁴—Q wherein X⁴ is SO₂ or CO and Q has any of the meanings defined immediately hereinafter; and
  Q is phenyl, naphthyl, phenyl-(1–4C)alkyl, phenyl-(2–4C)alkenyl or phenyl-(2–4C)alkynyl, and Q optionally bears 1, 2 or 3 substituents selected from halogeno, trifluoromethyl, trifluoromethoxy, cyano, hydroxy, amino, nitro, trifluoromethanesulphonyl, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, phenyl, phenoxy, phenylthio, phenylsulphinyl, phenylsulphonyl, benzyl and benzoyl, and wherein said phenyl, phenoxy, phenylthio, phenylsulphinyl, phenylsulphonyl, benzyl or benzoyl substituent optionally bears 1, 2 or 3 substituents selected from halogeno, trifluoromethyl, cyano, hydroxy, amino, nitro, carboxy, carbamoyl, (1–4C)alkyl, (1–4C)alkoxy, (1–4C)alkylamino, di-(1–4C)alkylamino, (1–4C)alkoxycarbonyl, N-(1–4C)alkylcarbamoyl, N,N-di-(1–4C)alkylcarbamoyl and (2–4C)alkanoylamino;
or a pharmaceutically-acceptable salt thereof;
provided that when X¹ is CO and Ar is phenylene which optionally bears 1 or 2 substituents selected from halogeno, trifluoromethyl, (1–4C)alkyl and (1–4C)alkoxy then X² is not N(R⁷)SO₂, N(R⁷)CO, C(R⁶)₂S, C(R⁶)₂SO, C(R⁶)₂SO₂, C(R⁶)₂—C(R⁶)₂, C(R⁶)₂CO or C(R⁶)₂O.

8. A compound which is:

1-[4-(6-chloronaphth-2-ylsulphonyl)benzoyl]-4-(4-pyridyl)piperazine,
1-[4-(6-bromonaphth-2-ylsulphonyl)benzyl]-4-(4-pyridyl)piperazine, 1-[4-(2-naphthylsulphonyl)benzoyl]-4-(4-pyridyl)piperazine,
1-{4-[(E)-4-chlorostyrylsulphonyl]benzoyl}-4-(4-pyridyl)piperazine,
1-[4-(4'-bromo-4-biphenylylsulphonyl)benzoyl]-4-(4-pyridyl)piperazine,
1-[4-(4'-chloro-4-biphenylylsulphonyl)benzoyl]-4-(4-pyridyl)piperazine,
1-[4-(4-biphenylylsulphonyl)benzoyl]-4-(4-pyridyl)piperazine,
5-(6-chloronaphth-2-ylsulphonyl)-2-[4-(4-pyridyl)piperazin-1-ylcarbonyl]benzoic acid,
5-(2-naphthylsulphonyl)-2-[4-(4-pyridyl)piperazin-1-ylcarbonyl]benzoic acid,
5-(4'-bromo-4-biphenylylsulphonyl)-2-[4-(4-pyridyl)piperazin-1-ylcarbonyl]benzoic acid,
5-[(E)-4-chlorostyrylsulphonyl]-2-[4-(4-pyridyl)piperazin-1-ylcarbonyl]benzoic acid,
4'-bromo-N-{4-[1-(4-pyridyl)piperidin-4-yloxy]phenyl}-4-biphenylylsulphonamide,
4-chloro-N-{4-[1-(4-pyridyl)piperidin-4-yloxy]phenyl}-(E)-styrylsulphonamide,
6-bromo-N-{4-[1-(4-pyridyl)piperidin-4-yloxy]phenyl}-2-naphthalenesulphonamide,
N-{4-[1-(4-pyridyl)piperidin-4-yloxy]phenyl}-4-toluenesulphonamide,
N-{4-[1-(4-pyridyl)piperidin-4-yloxy]phenyl}-N-(4-tolylsulphonyl)-4-toluenesulphonamide,
4-chloro-N-methyl-N-{4-[1-(4-pyridyl)piperidin-4-yloxy]phenyl}-(E)-styrylsulphonamide,
4'-bromo-N-methyl-N-{4-[1-(4-pyridyl)piperidin-4-yloxy]phenyl}-4-biphenylylsulphonamide,
4'-bromo-N-{4-[1-(4-pyridyl)piperidin-4-ylmethoxy]phenyl}-4-biphenylylsulphonamide,
6-bromo-N-{4-[1-(4-pyridyl)piperidin-4-ylmethoxy]phenyl}-2-naphthalenesulphonamide,
4-chloro-N-{4-[1-(4-pyridyl)piperidin-4-ylmethoxy]phenyl}-(E)-styrylsulphonamide,
4'-bromo-N-(4'-bromo-4-biphenylylsulphonyl)-N-{4-[1-(4-pyridyl)piperidin-4-ylmethoxy]phenyl}-4-biphenylylsulphonamide,
6-bromo-N-(6-bromonaphth-2-ylsulphonyl)-N-{4-[1-(4-pyridyl)piperidin-4-ylmethoxy]phenyl}-2-naphthalenesulphonamide,
6-bromo-N-{3-[1-(4-pyridyl)piperidin-4-yloxy]phenyl}-2-naphthalenesulphonamide,
4-[4-chlorophenyl)phenoxy]-1-(4-(pyridyl)piperidine,
5-(6-bromonaphth-2-ylsulphonyl)-2-[4-(4-pyridyl)piperazin-1-ylcarbonyl]benzoic acid,
4-(6-bromonaphth-2-ylsulphonyl)-2-[4-(4-pyridyl)piperazin-1-ylcarbonyl]benzoic acid,
1-[4-(4-(4-chlorophenoxy)phenylaminocarbonyl)benzyl]-4-(4-pyridyl)piperazine,
6-bromo-N-{2-[1-(4-pyridyl)piperidin-4-ylmethoxy]phenyl}-2-naphthalenesulphonamide,
4-chloro-N-{3-[1-(4-pyridyl)piperidin-4-yloxy]phenyl}-(E)-styrylsulphonamide,
4-[4-(6-bromonaphth-2-ylsulphonyl)phenoxy]-1-(4-pyridyl)piperidine,
4-[4-(6-bromonaphth-2-ylsulphonyl)benzoyl]-1-(4-pyridyl)piperidine,
4-[4-(6-bromonaphth-2-ylthio)benzoyl]-1-(4-pyridyl)piperidine,
4-[4-(6-bromonaphth-2-ylsulphonyl)phenylsulphonyl]-1-(4-pyridyl)piperazine,
1-[4-(6-bromonaphth-2-ylthio)benzoyl]-4-(4-pyridyl)piperazine,
1-[4-(6-bromonaphth-2-ylsulphonyl)benzoyl]-4-(4-pyridyl)piperazine,
1-[4-(6-bromonaphth-2-ylsulphonyl-2-trifluoromethylbenzoyl]-4-(4-pyridyl)piperazine,
1-[4-(6-bromonaphth-2-ylthio)-2-trifluoromethylbenzoyl]-4-(4-pyridyl)piperazine,
1-[4-(6-bromonaphth-2-ylthio)-2-carboxybenzoyl]-4-(4-pyridyl)piperazine
1-[5-(6-bromonaphth-2-ylthio)-2-carboxybenzoyl]-4-(4-pyridyl)piperazine,
1-[5-(6-bromonaphth-2-ylsulphonyl)-2-methoxycarbonylbenzoyl]-4-(4-pyridyl)piperazine,
1-[4-(6-bromonaphth-2-ylsulphonyl)-2-methoxycarbonylbenzoyl]-4-(4-pyridyl)piperazine,
1-[4-(6-bromonaphth-2-ylsulphonyl)-2-(2-(ethylthio)-ethylaminocarbonyl)benzoyl]-4-(4-pyridyl)piperazine,
1-[5-(6-bromonaphth-2-ylsulphonyl)-2-(2-ethylthio)ethylaminocarbonyl)benzoyl]-4-(4-pyridyl)piperazine,
1-[4-(6-bromonaphth-2-ylsulphonyl)benzoyl]-4-(2-methylpyrid-4-yl)piperazine,
1-[4-(6-bromonaphth-2-ylsulphonyl)benzoyl]-4-(4-pyridyl)hexahydro-1,4-diazepine, or a pharmaceutically-acceptable salt thereof.

9. A method of producing an antithrombotic or anticoagulant effect in a warm-blooded animal in need thereof, which comprises administering to said animal an effective amount of a compound as claimed in any one of claims 8, 1 and 2.

10. A method of treating coronary artery or cerebrovascular disease in a warm-blooded animal in need thereof, which comprises administering to said animal an effective amount of an aminoheterocyclic compound of formula I:

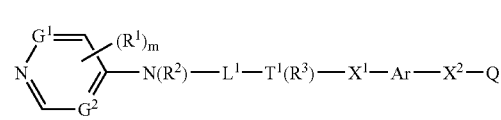

wherein
$G^1$ is CH;
$G^2$ is CH;
m is 1 or 2;
$R^1$ is hydrogen, halogeno, trifluoromethyl, trifluoromethoxy, cyano, amino, hydroxy, nitro, (1–4C)alkyl, (1–4C)alkoxy, (1–4C)alkylamino or di-(1–4C)alkylamino;
$L^1$ is (1–4C)alkylene, (3–6C)cycloalkane-1,2-diyl or (1–3C)alkylene-carbonyl,
$T^1$ is CH or N, and
$R^2$ and $R^3$ together form a (1–4C)alkylene or methylenecarbonyl group, and wherein 1 or 2 methylene groups within $L^1$ or the ring formed when $R^2$ and $R^3$ are linked optionally bear 1 or 2 substituents selected from carboxy, carbamoyl, (1–4C)alkyl, (1–4C)alkoxycarbonyl, N-(1–4C)alkylcarbamoyl, N,N-di-(1–4C)alkylcarbamoyl, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl and N,N-di-(1–4C)alkylcarbamoyl-(1–4C)alkyl,
provided that, when $T^1$ is N, $L^1$ is not optionally substituted methylene and $R^2$ and $R^3$ together do not form an optionally substituted methylene group;
$X^1$ is a group of the formula SO, $SO_2$, $C(R^4)_2$, CO, $C(R^4)_2O$, $C(R^4)_2S$, $C(R^4)_2SO$, $C(R^4)_2SO_2$, $COC(R^4)_2$, SOC($R^4$)$_2$ or SO$_2$C($R^4$)$_2$ when $T^1$ is CH or N, or, in addition, $X^1$ is a group of the formula O, S, OC($R^4$)$_2$ or SC($R^4$)$_2$ when $T^1$ is CH, and wherein each $R^4$ is independently hydrogen or (1–4C)alkyl;

Ar is a 1,3-phenylene or 1,4-phenylene, wherein said phenylene ring is optionally substituted with 1 or 2 substituents selected from halogeno, trifluoromethyl, trifluoromethoxy, cyano, nitro, (1–4C)alkyl, (2–4C)alkenyl and (2–4C)alkynyl, from the substituent $Y^1$ which is selected from hydroxy, amino, (1–4C)alkoxy, (2–4C)alkenyloxy, (2–4C)alkynyloxy, (1–4C)alkylamino, di-(1–4C)alkylamino, (1–4C)alkylthio, (1–4C)alkylsulphinyl, (1–4C)alkylsulphonyl, (2–4C)alkanoylamino, benzamido, (1–4C)alkanesulphonamido and benzenesulphonamido, from the substituent $Y^2$ which is selected from carboxy, carbamoyl, (1–4C)alkoxycarbonyl, N-(1–4C)alkylcarbamoyl, N,N-di-(1–4C)alkylcarbamoyl, (1–4C)alkanesulphonamidocarbonyl, benzenesulphonamidocarbonyl and benzylsulphonamidocarbonyl, from a substituent of the formula —$L^2$—$Y^1$ wherein $L^2$ is (1–4C)alkylene and $Y^1$ has any of the meanings defined immediately hereinbefore, from a substituent of the formula —$L^2$—$Y^2$ wherein $L^2$ is (1–4C)alkylene and $Y^2$ has any of the meanings defined immediately hereinbefore, from a substituent of the formula —$X^3$—$L^2$—$Y^2$ wherein $X^3$ is a group of the formula CON($R^5$), CON($L^2$—$Y^2$), C($R^5$)$_2$O, O, N($R^5$) or N($L^2$—$Y^2$), $L^2$ is (1–4C)alkylene, $Y^2$ has any of the meanings defined immediately hereinbefore and each $R^5$ is independently hydrogen or (1–4C)alkyl, and from a substituent of the formula —$X^3$—$L^3$—$Y^1$ wherein $X^3$ is a group of the formula CON($R^5$), CON($L^3$—$Y^1$), C($R^5$)$_2$O, O, N($R^5$) or N($L^3$—$Y^1$), $L^3$ is (2–4C)alkylene, $Y^1$ has any of the meanings defined immediately hereinbefore and each $R^5$ is independently hydrogen or (1–4C)alkyl, and wherein any phenyl group in said substituent optionally bears 1 or 2 substituents selected from halogeno, trifluoromethyl, cyano, (1–4C)alkyl, (2–4C)alkenyl, (2–4C)alkynyl, (1–4C)alkoxy, (2–4C)alkenyloxy and (2–4C)alkynyloxy;

$X^2$ is a group of the formula S, SO, SO$_2$, C($R^6$)$_2$, CO, N($R^7$)SO$_2$, N($R^7$)CO, C($R^6$)$_2$S, C($R^6$)$_2$SO, C($R^6$)$_2$SO$_2$, C($R^6$)$_2$—C($R^6$)$_2$ or C($R^6$)$_2$CO, or, in addition, $X^2$ is a group of the formula O, SO$_2$N($R^7$), CON($R^7$) or C($R^6$)$_2$O when Q is other than phenyl-(2–4C)alkenyl or phenyl-(2–4C)alkynyl and wherein each $R^6$ is independently hydrogen or (1–4C)alkyl and $R^7$ is hydrogen, (1–4C)alkyl or a group of the formula —$X^4$—Q wherein $X^4$ is SO$_2$ or CO and Q has any of the meanings defined immediately hereinafter; and Q is phenyl, naphthyl, phenyl-(1–4C)alkyl, phenyl-(2–4C)alkenyl or phenyl-(2–4C)alkynyl, and Q optionally bears 1, 2 or 3 substituents selected from halogeno, trifluoromethyl, trifluoromethoxy, cyano, hydroxy, amino, nitro, trifluoromethanesulphonyl, carboxy, carbamoyl, (1–4C)alkyl, (2–4C)alkenyl, (2–4C)alkynyl, (1–4C)alkoxy, (2–4C)alkenyloxy, (2–4C)alkynyloxy, (1–4C)alkylthio, (1–4C)alkylsulphinyl, (1–4C)alkylsulphonyl, (1–4C)alkylamino, di-(1–4C)alkylamino, (1–4C)alkoxycarbonyl, N-(1–4C)alkylcarbamoyl, N,N-di-(1–4C)alkylcarbamoyl, (2–4C)alkanoyl, (2–4C)alkanoylamino, hydroxy-(1–4C)alkyl, (1–4C)alkoxy-(1–4C)alkyl, carboxy-(1–4C)alkyl, (1–4C)alkoxycarbonyl-(1–4C)alkyl, carbamoyl-(1–4C)alkyl, N-(1–4C)alkylcarbamoyl-(1–4C)alkyl, N,N-di-(1–4C)alkylcarbamoyl-(1–4C)alkyl, phenyl, phenoxy, phenylthio, phenylsulphinyl, phenylsulphonyl, benzyl and benzoyl, and wherein said phenyl, heteroaryl, phenoxy, phenylthio, phenylsulphinyl, phenylsulphonyl, benzyl or benzoyl substituent optionally bears 1, 2 or 3 substituents selected from halogeno, trifluoromethyl, cyano, hydroxy, amino, nitro, carboxy, carbamoyl, (1–4C)alkyl, (1–4C)alkoxy, (1–4C)alkylamino, di-(1–4C)alkylamino, (1–4C)alkoxycarbonyl, N-(1–4C)alkylcarbamoyl, N,N-di-(1–4C)alkylcarbamoyl and (2–4C)alkanoylamino;

or a pharmaceutically-acceptable salt thereof;

provided that when $X^1$ is CO and Ar is phenylene which optionally bears 1 or 2 substituents selected from halogeno, trifluoromethyl, (1–4C)alkyl and (1–4C)alkoxy then $X^2$ is not N($R^7$)SO$_2$, N($R^7$)CO, C($R^6$)$_2$S, C($R^6$)$_2$SO, C($R^6$)$_2$SO$_2$, C($R^6$)$_2$—C($R^6$)$_2$CO or C($R^6$)$_2$O.

11. A method of treating coronary artery or cerebrovascular disease in a warm-blooded animal in need thereof, which comprises administering to said animal an effective amount of a compound as claimed in claims 8, 1 and 2.

12. A pharmaceutical composition which comprises a compound or a pharmaceutically acceptable salt thereof as claimed in claim 8, and a pharmaceutically acceptable carrier.

13. A method of producing an antithrombatic or anticoagulant effect comprising administering an aminoheterocyclic derivative of the formula I or a pharmaceutically acceptable salt thereof as claimed in claim 1 or 2, and a pharmaceutically acceptable carrier.

14. A process for the preparation of an aminoheterocyclic compound of the formula I or a pharmaceutically acceptable salt thereof as claimed as claim 1 which comprises:

a) for the production of those compounds of the formula I wherein $T^1$ is N and $X^1$ is CO, the reaction, conveniently in the presence of a suitable base, of an amine of the formula II

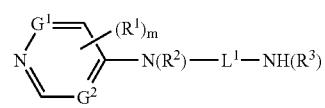

II with an acid of the formula III

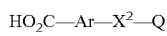

III or a reactive derivative thereof;

(aa) for the preparation of those compounds of the formula I wherein $T^1$ is N and $X^1$ is a group of the formula COC($R^4$)$_2$, the reaction, conveniently in the presence of a suitable base, of an amine of the formula II with an acid of the formula:

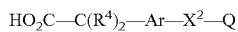

or a reactive derivative thereof;

(b) for the production of those compounds of the formula I wherein $T^1$ is CH and $X^1$ is O or C($R^4$)$_2$O, the reaction, conveniently in the presence of a suitable coupling agent, of a compound of the formula IV

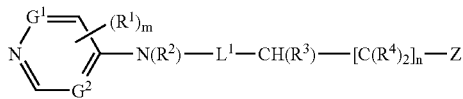

IV wherein n is 0 or 1 and Z is a displaceable group, with a phenolic compound of the formula V

HO—Ar—X²—Q    V (bb) for the preparation of those compounds of the formula I wherein T¹ is CH and X¹ is a group of the formula S or $C(R^4)_2S$, the reaction, conveniently in the presence of a suitable coupling agent, of a compound of the formula IV with a compound of the formula:

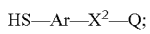

HS—Ar—X²—Q;

(c) for the production of those compounds of the formula I wherein T¹ is N and X¹ is $CH(R^4)$, the reductive amination of a keto compound of the formula VI

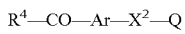

R⁴—CO—Ar—X²—Q    VI with an amine of the formula VII

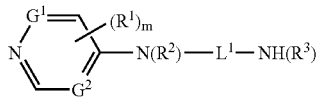

VII (d) for the production of those compounds of the formula I wherein X² is a group of the formula $N(R^7)SO_2$, the reaction, conveniently in the presence of a suitable base, of an amine of the formula VIII

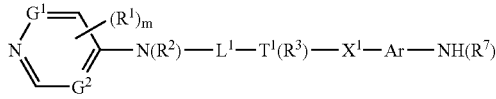

VIII with a compound of the formula IX

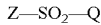

Z—SO₂—Q    IX wherein Z is a displaceable group;

(dd) for the production of those compounds of the formula I wherein X² is a group of the formula $N(R^7)CO$, the reaction, conveniently in the presence of a suitable base, of an amine of the formula VIII with a compound of the formula: Z—CO—Q;

(e) for the production of those compounds of the formula I wherein X² is a group of the formula $N(R^7)SO_2$, the reaction, conveniently in the presence of a suitable base, of a sulphonamide of the formula X

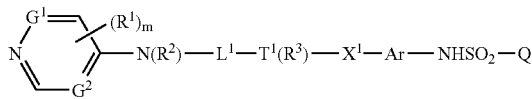

X with a compound of the formula XI

R⁷—Z    XI wherein Z is a displaceable group;

(ee) for the production of those compounds of the formula I wherein X² is a group of the formula $N(R^7)CO$, the reaction conveniently in the presence of a suitable base, of a compound of the formula I wherein $N(R^7)CO$ is NHCO with a compound of the formula XI;

(f) for the production of those compounds of the formula I wherein X² is a group of the formula $SO_2N(R^7)$ the reaction, conveniently in the presence of a suitable base of a compound of the formula XII

XII

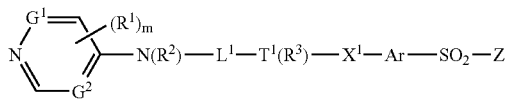

wherein Z is a displaceable group as defined hereinbefore, with an amine of the formula XIII (R⁷)NH—Q    XIII (ff) for the preparation of those compounds of the formula I wherein X² is a group of the formula $CON(R^7)$, the reaction, conveniently in the presence of a suitable base, of a compound of the formula XIII with a carbonyl compound corresponding to the sulphonyl compound of the formula XII;

(g) for the production of those compounds of the formula I wherein T¹ is CH and X¹ is a group of the formula $OC(R^4)_2$, the reaction conveniently in the presence of a suitable coupling agent of an alcohol of the formula XIV

XIV

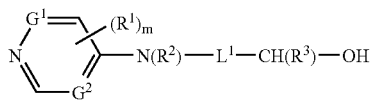

with a compound of the formula XV

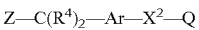

Z—C(R⁴)₂—Ar—X²—Q    XV wherein Z is a displaceable group;

(gg) for the preparation of those compounds of the formula I wherein T¹ is CH and X¹ is a group of the formula $SC(R^4)_2$, the reaction conveniently in the presence of a suitable coupling agent of the thiol equivalent of formula XIV with a compound of the formula XV;

(h) for the production of those compounds of the formula I wherein X² is a group of the formula $C(R^6)_2S$, the reaction, conveniently in the presence of a suitable base, of a compound of the formula XVI

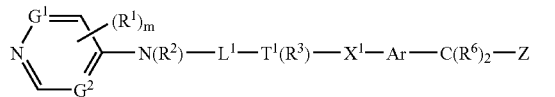

XVI wherein Z is a displaceable group with a thiol of the formula XVII

HS—Q    XVII (i) for the production of those compounds of the formula I wherein $L^1$, $R^2$, $R^3$, Ar or Q bears a carboxy or carboxy-containing group, the hydrolysis of a compound of the formula I wherein $L^1$, $R^2$, $R^3$, Ar or Q bears a (1–4C)alkoxycarbonyl group;

(j) for the production of those compounds of the formula I wherein $L^1$, $R^2$, $R^3$, Ar or Q bears a carbamoyl, N-alkylcarbamoyl or N,N-dialkylcarbamoyl group, the reaction of a compound of the formula I wherein $L^1$, $R^2$, $R^3$, Ar or Q bears a carboxy group, or a reactive derivative thereof as defined hereinbefore, with ammonia or an appropriate alkylamine or dialkylamine;

(k) for the production of those compounds of the formula I wherein $X^1$ is a group of the formula SO, $SO_2$, $C(R^4)_2SO$, $C(R^4)_2SO_2$, $SOC(R^4)_2$ or $SO_2C(R^4)_2$, wherein Ar bears a (1–4C)alkylsulphinyl or (1–4C)alkylsulphonyl, or a substituent which contains a (1–4C)alkylsulphinyl or (1–4C)alkylsulphonyl, wherein $X^2$ is a group of the formula SO, $SO_2$, $C(R^6)_2SO$ or $C(R^6)_2SO_2$, or wherein Q bears a (1–4C)alkylsulphinyl, (1–4C)alkylsulphonyl, phenylsulphinyl or phenylsulphonyl, the oxidation of the corresponding compound of the formula I which contains a thio group;

l) the reaction of an activated derivative of a compound of the formula XVIII:

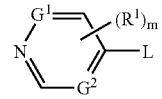

XVIII wherein L is a displaceable group as hereinbefore with a compound of the formula XIX:

NH($R^2$)—$L^1$—$T^1$($R^3$)—$X^1$—Ar—Q    XIX and, if necessary, forming a pharmaceutically associated salt.

* * * * *